United States Patent
Khan et al.

(10) Patent No.: US 9,334,235 B2
(45) Date of Patent: May 10, 2016

(54) PLASMALOGEN COMPOUNDS, PHARMACEUTICAL COMPOSITIONS CONTAINING THE SAME AND METHODS FOR TREATING DISEASES OF THE AGING

(75) Inventors: M. Amin Khan, Morgan Hill, CA (US); Paul L. Wood, Harrogate, TN (US); Dayan Goodenowe, Saskatoon (CA); Rishikesh Mankidy, Saskatoon (CA); Pearson Ahiahonu, Saskatoon (CA)

(73) Assignee: Phenomenome Discoveries Inc., Saskatoon, Saskatchewan (CA)

( * ) Notice: Subject to any disclaimer, the term of this patent is extended or adjusted under 35 U.S.C. 154(b) by 1248 days.

(21) Appl. No.: 13/141,035

(22) PCT Filed: Dec. 18, 2009

(86) PCT No.: PCT/CA2009/001853
§ 371 (c)(1),
(2), (4) Date: Oct. 27, 2011

(87) PCT Pub. No.: WO2010/071988
PCT Pub. Date: Jul. 1, 2010

(65) Prior Publication Data
US 2012/0035250 A1    Feb. 9, 2012
US 2013/0116312 A2    May 9, 2013

Related U.S. Application Data

(60) Provisional application No. 61/139,695, filed on Dec. 22, 2008.

(51) Int. Cl.
C07C 229/22    (2006.01)
C07C 323/59    (2006.01)
(Continued)

(52) U.S. Cl.
CPC ............. C07C 323/59 (2013.01); C07C 229/22 (2013.01); C07C 279/14 (2013.01); C07D 339/04 (2013.01); C07F 9/106 (2013.01)

(58) Field of Classification Search
CPC .. C07C 229/22; C07C 279/14; C07C 323/59; C07D 339/04
See application file for complete search history.

(56) References Cited

U.S. PATENT DOCUMENTS 4,827,011 A    5/1989    Wissner et al.
5,759,585 A    6/1998    Forgeot
(Continued)

FOREIGN PATENT DOCUMENTS

EP    2123281    * 11/2009    ........... A61K 31/661
JP    2004-26803 A    1/2004
(Continued)

OTHER PUBLICATIONS
Slotboom, A.J. et al., on the synthesis of plasmalogens, 1967, Chem. ys. Lipids, vol. 1, No. 3, pp. 192-208.*
(Continued)

*Primary Examiner* — Yate K Cutliff
(74) *Attorney, Agent, or Firm* — LeClairRyan, a Professional Corporation

(57) ABSTRACT

Described herein are routes of synthesis and therapeutic uses of 1-alkyl, 2-acyl glycerol derivatives of formula I: which when administered to mammalian biological systems result in increased cellular concentrations of specific sn-2 substituted ethanolamine plasmalogens independent of the ether lipid synthesis capacity of the system. Elevating levels of the specific sn-2 substituted species in this way can cause lowering of membrane cholesterol levels and the lowering of amyloid secretion. These compounds can be used for the treatment or prevention of diseases of aging associated with increased membrane cholesterol, increased amyloid, and decreased plasmalogen levels, such as neurodegeneration (including Alzheimer's disease, Parkinson's disease and age-related macular degeneration), cognitive impairment, dementia, cancer (e.g. prostate, lung, breast, ovarian, and kidney cancers), osteoporosis, bipolar disorder and vascular diseases (such as atherosclerosis, hypercholesterolemia).

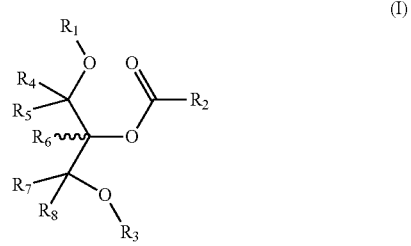

(I)

6 Claims, 14 Drawing Sheets

Scheme 1.

(51) Int. Cl.
C07C 279/14 (2006.01)
C07D 339/04 (2006.01)
C07F 9/10 (2006.01)

(56) References Cited

U.S. PATENT DOCUMENTS 6,835,750 B1  12/2004  Henderson
2008/0020472 A1  1/2008  Shan et al.
2008/0021000 A1  1/2008  Chen et al.

FOREIGN PATENT DOCUMENTS

WO  2004/106486 A2  12/2004
WO  2007/098585 A1   7/2007
WO  2008/093709 A1   7/2008
WO  2008/095275 A1   8/2008
WO  2008/124916 A1  10/2008

OTHER PUBLICATIONS

Ravandi et al., "Glucosylated Glycerophosphoethanolamines are the Major LDL Glycation Products and Increase LDL Susceptibility to Oxidation," Arterioscler. Thromb. Vasc. Biol. 20:467-477 (2000).
Peters et al., "Platelet Activating Factor Synthetic Studies," Tetrahedron 43(16):3803-3816 (1987).
Goodenowe et al., "Peripheral Ethanolamine Plasmalogen Deficiency: A Logical Causative Factor in Alzheimer's Disease and Dementia," J. Lipid Res. 48:2485-2498 (2007).
Maczurek et al., "Lipoic Acid as an Anti-Inflammatory and Neuroprotective Treatment for Alzheimer's Disease," Adv. Drug Del. Rev. 60:1463-1470 (2008).
Han, "Lipid Alterations in the Earliest Clinically Recognizable Stage of Alzheimer's Disease: Implication of the Role of Lipids in the Pathogenesis of Alzheimer's Disease," Curr. Alzheimer Res. 2:65-77 (2005).
Kaburagi et al., "An Operationally Simple and Efficient Work-Up Procedure for TBAF—Mediated Desilylation; Application to Halichondrin Synthesis," Org. Lett. 9(4):723-726 (2007).
Stamatov et al. "Regioselective and Stereospecific Acylation Across Oxirane- and Silyloxy Systems as a Novel Strategy to the Synthesis of Enantiomerically Pure Mono-, di- and Triglycerides," Organic and Biomolecular Chemistry 5:3787-3800 (2007).
Thompson et al. "Synthesis of Chiral Diether and Tetraether Phospholipids: Regiospecific Ring Opening of Epoxy Alcohol Intermediates Derived from Asymmetric Expoxidation," Journal of Organic Chemistry 59:2945-2955 (1994).
Xia et al. "The Chemical Synthesis of Ether Phospholipids from D-mannitol and their Properties," Tetrahedron: Asymmetry 8(18):3131-3142 (1997).
International Search Report and Written Opinion for PCT/CA2009/001853, mailed Mar. 12, 2010.
Hager et al., "The Role of Cholesterol in Prostate Cancer," Curr. Opin. Clin. Nutr. Metab. Care 9:379-85 (2006).
Distl et al., "Tangle-Bearing Neurons Contain More Free Cholesterol than Adjacent Tangle-Free Neurons," Acta Neuropathol. 101:547-554 (2001).
Hashimoto et al., "Effects of Aging on the Relation of Adenyl Purine Release with Plasma Membrane Fluidity of Arterial Endothelial Cells," Prostagland. Leukotri. Ess. Fatty Acids 73:475-483 (2005).

Xiu et al., "Influence of Cholesterol and Lovastatin on Alpha-Form of Secreted Amyloid Precursor Protein and Expression of Alpha7 Nicotinic Receptor on Astrocytes," Neurochem. Internat. 49:459-465 (2006).
Corrigan et al., "Abnormal Content of n-6 and n-3 Long-Chain Unsaturated Fatty Acids in the Phosphoglycerides and Cholesterol Esters of Parahippocampal Cortex from Alzheimer's Disease Patients and its Relationship to Acetyl CoA Content," Internat. J. Biochem. Cell Biol. 30:197-207 (1998).
Sigle et al., "High Potassium-Induced Activation of Choline-Acetyltransferase in Human Neocortex: Implications and Species Differences," Brain Res. Bulletin 60:255-262 (2003).
Beel et al., "Structural Studies of the Transmembrane C-Terminal Domain of the Amyloid Precursor Protein (APP): Does APP Function as a Cholesterol Sensor?" Biochemistry 47:9428-9446 (2008).
Li et al., "Distribution and Composition of Esterified and Unesterified Cholesterol in Extra-Macular Drusen," Experiment. Eye Res. 85:192-201 (2007).
Campbell et al., "Mitochondria! Membrane Cholesterol, the Voltage Dependent Anion Channel (VDAC), and the Warburg Effect," J. Bioenerg. Biomembr. 40:193-197 (2008).
Lewin et al., "Lipid Changes with Aging in Cardiac Mitochodrial Membranes," Mechanisms Aging Develop. 24:343-351 (1984).
Wu et al., "Comparison of Aging and Hypercholesterolemic Effects on the Sodium Inward Currents in Cardiac Myocytes," Life Sciences 61(16):1539-1551 (1997).
Calderini et al., "Biochemical Changes of Rat Brain Membranes with Aging," Neurochem. Res. 8(4):483-492 (1983).
Hashimoto et al., "Effect of Aging on Plasma Membrane Fluidity of Rat Aortic Endothelial Cells," Exp. Gerontol. 4 34:687-698 (1999).
Guo et al., "Effects of Cholesterol Levels on the Excitability of Rat Hippocampal Neurons," Mol. Memb. Biol. 25 (3):216-223 (2008).
Kessler et al., "Changes in the Cholesterol Leve, Cholesterol-to-Phospholipid Mole Ratio, and Membrane Lipid Microviscosity in Rat Brain Induced by Age and Plant Oil Mixture," Biochem. Pharmocol. 24(7):1120-1121 (1985)
Modi et al., "Ageing-Induced Alterations in Lipid/Phospholipid Profiles of Rat Brain and Liver Mitochondria: Implications for Mitochondrial Energy-Linked Functions," J. Memb. Biol. 221:51-60 (2008).
Santiago et al., "Probing the Effects of Membrane Cholesterol in the Torpedo Californica Acetylcholine Receptor and the Novel Lipid-Exposed Mutation AlphaC418W in Xenopus Oocytes," J. Biol. Chem. 276(49):46523-46532 (2001).
Miersch et al., "Plasma Membrane Cholesterol Content Affects Nitric Oxide Diffusion Dynamics and Signaling," J. Biol. Chem. 283(27):18513-18521 (2008)
Cutler et al., "Involvement of Oxidative Stress-Induced Abnormalities in Ceramide and Cholesterol Metabolism in Brain Aging and Alzheimer's Disease," Proc. Nat. Acad. Sci. U.S.A. 101(7):2070-2075 (2004).
Grimm et al., "Independent Inhibition of Alzheimer Disease Beta- and Gamma-Secretase Cleavage by Lowered Cholesterol Levels," J. Biol. Chem. 283(17):11302-11311 (2008).
Simons et al., "Cholesterol Depletion Inhibits the Generation of Beta-Amyloid in Hippocampal Neurons," Proc. Nat. Acad. Sci. U.S. A. 95:6460-6464 (1998).
Vejux et al., "Side Effects of Oxysterols: Cytotoxicity, Oxidation, Inflammation, and Phospholipidosis," Brazilian J. Med. Biol. Res. 41:545-556 (2008).
Wolozin et al., "Simvastatin is Associated with a Reduced Incidence of Dementia and Parkinson's Disease," BMC Med. 5:20, pp. 1-11, (2007).

* cited by examiner

Scheme 1.

PLASMALOGEN COMPOUNDS, PHARMACEUTICAL COMPOSITIONS CONTAINING THE SAME AND METHODS FOR TREATING DISEASES OF THE AGING

This application is a national stage application under 35 U.S.C. §371 from PCT Application No. PCT/CA2009/001853, filed Dec. 18, 2009, which claims the priority benefit of U.S. Provisional Application No. 61/139,695, filed Dec. 22, 2008.

FIELD OF INVENTION

The present invention relates to the synthesis and utility of novel chemical entities with useful biochemical, physiochemical, and clinical properties. More specifically, a series of 1-alkyl, 2-acyl glycerol derivatives are provided which can be used for the treatment or prevention of disease. The invention also relates to pharmaceutical compositions and kits incorporating such compounds.

BACKGROUND OF THE INVENTION

It is well known that many diverse human diseases such as cancer, dementia, or decreased cognitive functioning increase in incidence with age. From an epidemiological and statistical perspective, these diseases often look very similar. However, from a clinical perspective, each of the cancers, dementias, and decreased cognitive functioning are very different. Currently, the largest risk factor for these disorders is the subject's age. Furthermore, it is well established that most cancers, dementias, and decreased cognitive functioning have a long prodromal phase (5-15 years) in which the disease is present but at a sub-clinical manifestation. Age-associated increases in membrane cholesterol[1-3] and increased mitochondrial membrane cholesterol[4-6] have been reported. These increases in membrane cholesterol result in decreased membrane fluidity[2], decreased ion channel function[6-8], decreased activities of some membrane-bound enzymes like 5'-nucleotidase[9] and α-secretase[10], and altered diffusion properties for signaling molecules like nitric oxide[11].

Subjects suffering from increased membrane cholesterol demonstrate an increased prevalence of neurodegenerative diseases (e.g. Alzheimer's, Parkinson's, multiple sclerosis and age-related macular degeneration), cognitive impairment, dementia, cancers (e.g. prostate, lung, breast, ovarian, and kidney), osteoporosis, bipolar disorder and vascular diseases (atherosclerosis, hypercholesterolemia).

With respect to specific diseases, cholesterol accumulates in the brain membranes of Alzheimer's patients in a severity-dependent manner[12-14]. In this regard, lowering membrane cholesterol has been shown to decrease the activities of beta- and gamma-secretases, blocking the pathogenic processing of beta-amyloid[15-16]. At the molecular level, cholesterol binds to the transmembrane domain of amyloid precursor protein (APP), activating the trafficking of APP to cholesterol-rich membrane domains rich in beta- and gamma-secretases, resulting in amyloid-beta production[17]. Synaptic membrane changes resulting from increased cholesterol may also be an important factor in the utilization of membrane phospholipids to support cholinergic neurotransmission (autocannibalism concept)[18]. Early utilization of statins have also been suggested to reduce the incidence or delay the onset of Alzheimer's and Parkinson's diseases[19]. Cholesterol accumulation also occurs in the drusen associated with age-related macular degeneration[20]. Membrane cholesterol is also increased in cancer[21] and increases in mitochondrial membrane cholesterol have been hypothesized to be the defect that leads to the Warburg effect that is associated with most cancer cells[22]. The Warburg effect is a defining feature of cancer cells in that, unlike normal cells, which rely almost entirely upon respiration for energy, cancer cells can utilize both respiration and glycolysis for energy.

In addition to complex negative membrane effects of cholesterol accumulation, there is also increased oxysterol production[23]. These oxysterols are cytotoxic (apoptosis and necrosis), pro-inflammatory, deplete GSH and induce phospholipidosis[23-26]. Diseases in which these toxic oxysterols might be involved include neurodegeneration (both neuronal and demyelinating), osteoporosis, age-related macular degeneration and cardiovascular diseases, particularly atherosclerosis[23].

Current clinical therapies to reduce cholesterol consist mainly of inhibiting cholesterol synthesis with statins or blocking cholesterol absorption from the gastrointestinal tract with ezetimibe. To the inventors' knowledge, there are currently no drugs to mobilize cholesterol trafficking out of membranes.

SUMMARY OF THE INVENTION

The present invention relates to compounds and methods for treating diseases of aging associated with abnormal membrane cholesterol levels. The described compounds include novel plasmalogen precursors which decrease membrane free cholesterol levels and augment cholesterol esterification for transport from cell membranes. These compounds therefore are useful for reducing membrane cholesterol levels in subjects suffering from elevated membrane cholesterol levels. The compounds can also be used to treat or prevent diseases associated with increased membrane cholesterol such as neurodegenerative diseases (including but not limited to Alzheimer's disease, Parkinson's disease, multiple sclerosis and age-related macular degeneration), cognitive impairment, dementia, cancers (including but not limited to prostate, lung, breast, ovarian, and kidney cancer), osteoporosis, bipolar disorder and vascular diseases (including but not limited to atherosclerosis and hypercholesterolemia). Furthermore, these compounds are useful in the treatment of disorders resulting from abnormal genetic expression of cholesterol transport proteins, such as apolipoprotein E.

These plasmalogen precursors contain a glycerol backbone with an alkyl or alkenyl lipid substitution at sn-1 and an acyl lipid substitution at sn-2. A polar substituent is provided at sn-3 to improve pharmaceutical properties (such as to improve stability and/or bioavailability, or for formulation as a salt).

Without wishing to be bound by theory, it is believed that in certain embodiments the sn-3 substituent is cleaved by lipases and the resulting 1-alkyl, 2-acyl glycerol or 1-alkenyl, 2-acyl glycerol is then converted to plasmalogens in the endoplasmic reticulum, thereby bypassing the peroxisomal compartment which can demonstrate decreased function with ageing.

Accordingly, with respect to composition, there are provided compounds of formula I:

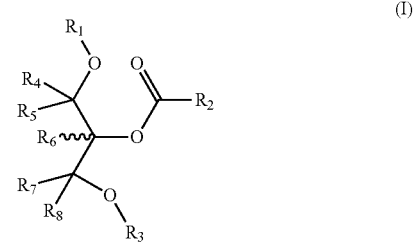

wherein:
R$_1$ and R$_2$ can be the same or different; and are an alkyl or alkenyl hydrocarbon chain selected from Table 1 or 2;

TABLE 1

Alkyl and alkenyl hydrocarbon groups

| No. | Chemical Structure | Abbr. |
|---|---|---|
| 1 | CH3(CH2)3— | C4:0 |
| 2 | CH3(CH2)5— | C6:0 |
| 3 | CH3(CH2)7— | C8:0 |
| 4 | CH3(CH2)9— | C10:0 |
| 5 | CH3(CH2)11— | C12:0 |
| 6 | CH3(CH2)13— | C14:0 |
| 7 | CH3(CH2)15— | C16:0 |
| 8 | CH3(CH2)17— | C18:0 |
| 9 | CH3(CH2)19— | C20:0 |
| 10 | CH3(CH2)21— | C22:0 |
| 11 | CH3(CH2)23— | C24:0 |
| 12 | CH3(CH2)3CH═CH(CH2)7— | C14:1 |
| 13 | CH3(CH2)5CH═CH(CH2)7— | C16:1 |
| 14 | CH3(CH2)7CH═CH(CH2)7— | C18:1 |
| 15 | CH3(CH2)4CH═CHCH2CH═CH(CH2)7— | C18:2 |
| 16 | CH3CH2CH═CHCH2CH═CHCH2CH═CH(CH2)7— | C18:3 |
| 17 | CH3CH2(CH═CH)— | C4:1 |
| 18 | CH3(CH2)3(CH═CH)— | C6:1 |
| 19 | CH3(CH2)5(CH═CH)— | C8:1 |
| 20 | CH3(CH2)7(CH═CH)— | C10:1 |
| 21 | CH3(CH2)9(CH═CH)— | C12:1 |
| 22 | CH3(CH2)11(CH═CH)— | C14:1 |
| 23 | CH3(CH2)13(CH═CH)— | C16:1 |
| 24 | CH3(CH2)15(CH═CH)— | C18:1 |
| 25 | CH3(CH2)17(CH═CH)— | C20:1 |
| 26 | CH3(CH2)19(CH═CH)— | C22:1 |
| 27 | CH3(CH2)21(CH═CH)— | C24:1 |
| 28 | CH3(CH2)3CH═CH(CH2)5(CH═CH)— | C14:2 |
| 29 | CH3(CH2)5CH═CH(CH2)5(CH═CH)— | C16:2 |
| 30 | CH3(CH2)7CH═CH(CH2)5(CH═CH)— | C18:2 |
| 31 | CH3(CH2)4CH═CHCH2CH═CH(CH2)5(CH═CH)— | C18:3 |
| 32 | CH3CH2CH═CHCH2CH═CHCH2CH═CH(CH2)5(CH═CH)— | C18:4 |

TABLE 2

Unsaturated cis fatty acid side chains

| No. | Name of acid | Chemical Structure |
|---|---|---|
| 1 | Myristoleic (14:1) | CH$_3$(CH$_2$)$_3$CH═CH(CH$_2$)$_7$— |
| 2 | Palmitoleic (16:1) | CH$_3$(CH$_2$)$_5$CH═CH(CH$_2$)$_7$— |
| 3 | Oleic (18:1) | CH$_3$(CH$_2$)$_7$CH═CH(CH$_2$)$_7$— |
| 4 | Linoleic (18:2) | CH$_3$(CH$_2$)$_4$(CH═CHCH$_2$)$_2$(CH$_2$)$_6$— |
| 5 | Linolenic (18:3) | CH$_3$CH$_2$(CH═CHCH$_2$)$_3$(CH$_2$)$_6$— |
| 6 | Arachidonic (20:4) | CH$_3$(CH$_2$)$_4$(CH═CHCH$_2$)$_4$(CH$_2$)$_2$— |
| 7 | Eicosapentaenoic (20:5) | CH$_3$CH$_2$(CH═CHCH$_2$)$_5$(CH$_2$)$_2$— |
| 8 | Erucic (22:1) | CH$_3$(CH$_2$)$_7$CH═CH(CH$_2$)$_{11}$— |
| 9 | Docosahexaenoic (22:6) | CH$_3$CH$_2$(CH═CHCH$_2$)$_6$CH$_2$— |

R$_3$ is a group selected from fatty acids, carnitine, acetyl-D/L-carnitine, thiocarnitine, acetyl-D/L-thiocarnitine, creatine, norcarnitine, phosphocholine, lipoic acid, dihydrolipoic acid, phosphoethanolamine, phosphoserine, N-acetylcysteine, substituted or unsubstituted amino acids and groups of the structures shown below in Table 3.

TABLE 3

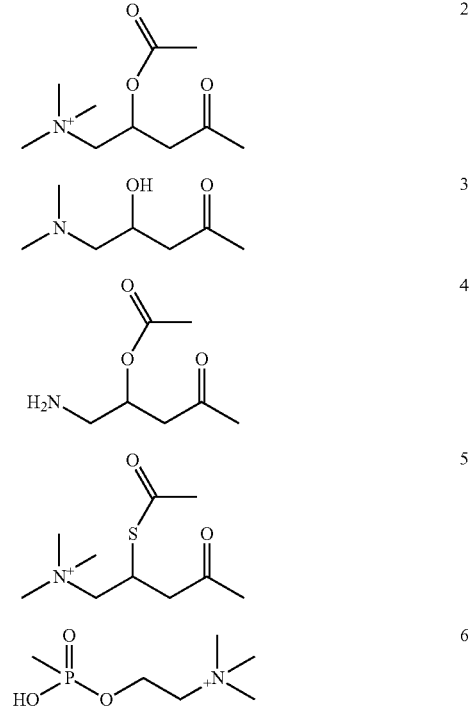

$R_4$ and $R_5$ are either the same or different and may be hydrogen or lower alkyl, for example methyl or ethyl;

$R_6$ is hydrogen or lower alkyl, for example methyl or ethyl; and $R_7$ and $R_8$ are either the same or different and may be hydrogen or lower alkyl, for example methyl and ethyl, and also including racemates or isolated stereoisomers and pharmaceutically acceptable salts or esters thereof.

Another aspect of this invention is directed to pharmaceutical compositions comprising a pharmaceutically acceptable carrier and a compound as described above.

In one embodiment of the present invention $R_2$ may be a docosahexaenoic acid (DHA) side chain, or $CH_3CH_2(CH=CHCH_2)_6CH_2$—.

In another embodiment, the compound can be 2-acetoxy-4-(2-((4Z,7Z,10Z,13Z,16Z,19Z)-docosa-4,7,10,13,16,19-hexaenoyloxy)-3-(hexadecyloxy)propoxy)-N,N,N-trimethyl-4-oxobutan-1-aminium.

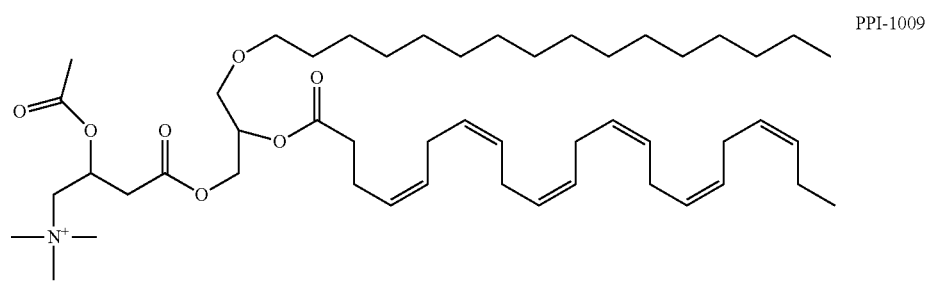 [SMILES: CC/C=C\C/C=C\C/C=C\C/C=C\C/C=C\C/C=C\CCC(=O)OC(COCCCCCCCCCCCCCCCC)COC(=O)CC(C[N+](C)(C)C)OC(C)=O]

PPI-1009

In other embodiments the compound may be (4Z,7Z,10Z,13Z,16Z,19Z)-1-(5-((R)-1,2-dithiolan-3-yl)pentanoyloxy)-3-(hexadecyloxy)propan-2-yl docosa-4,7,10,13,16,19-hexaenoate:

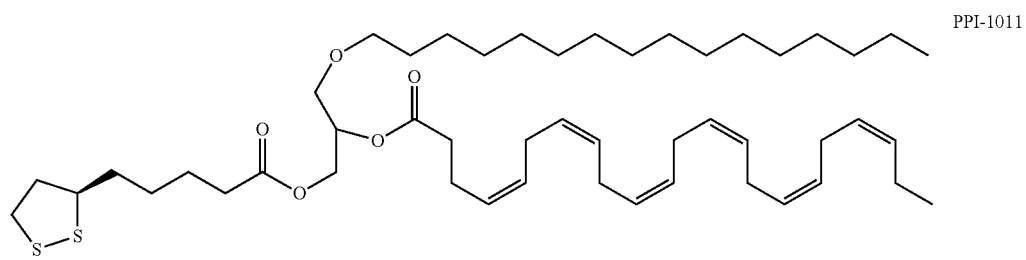 [SMILES: CC/C=C\C/C=C\C/C=C\C/C=C\C/C=C\C/C=C\CCC(=O)OC(COCCCCCCCCCCCCCCCC)COC(=O)CCCC[C@@H]1CCSS1]

PPI-1011 or (4Z,7Z,10Z,13Z,16Z,19Z)-1-(2-acetamido-3-mercaptopropanoyloxy)-3-(hexadecyloxy)propan-2-yl docosa-4,7,10,13,16,19-hexaenoate:

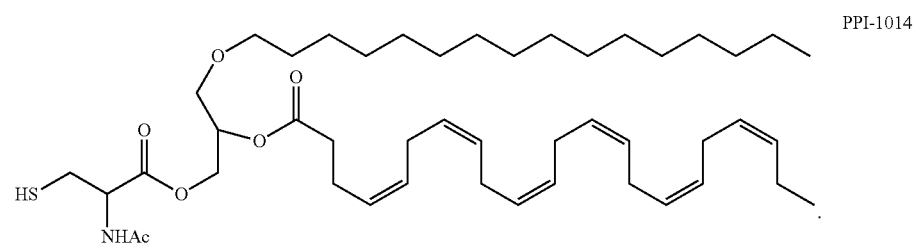 [SMILES: CC/C=C\C/C=C\C/C=C\C/C=C\C/C=C\C/C=C\CCC(=O)OC(COCCCCCCCCCCCCCCCC)COC(=O)C(CS)NC(C)=O]

PPI-1014

The invention also includes pharmaceutical compositions comprising PPI-1009, PPI-1011, PPI-1014, or combinations thereof.

Without wishing to be bound by theory, certain embodiments of the compounds described herein are believed to increase plasmalogen levels and the hydrolysis of acetyl-L-carnitine from sn-3 position, and may participate in potential molecular mechanisms that include: (i) acetylation of —NH$_2$ and —OH functional groups in amino acids and N-terminal amino acids in peptides and proteins resulting in modification of their structure, dynamic, function and turnover; and/or (ii) acting as a molecular chaperone to larger molecules resulting in a change in the structure, molecular dynamics, and function of the larger molecule.

Carnitine is important in the beta oxidation of fatty acids and the acetyl moiety can be used to maintain acetyl-CoA levels. Acetyl-L-carnitine (ALCAR) actions include modulation of: (i) brain energy and phospholipid metabolism; (iii) cellular macromolecules, including neurotrophic factors and hormones; (iii) synaptic morphology; and (iv) synaptic transmission of multiple neurotransmitters.

According to a further aspect of the present invention there is provided a method of treating or preventing diseases of aging mediated by plasmalogen deficiency, comprising administering to a patient in need thereof an effective amount of a compound or composition as described above.

In a further aspect of the present invention there is provided a method of treating diseases of aging associated with increased membrane cholesterol, increased amyloid and decreased plasmalogen levels comprising administering to a patient in need thereof, an effective amount of a compound or composition as described above.

The invention also relates to a process for preparing a compound according to the structure of formula II:

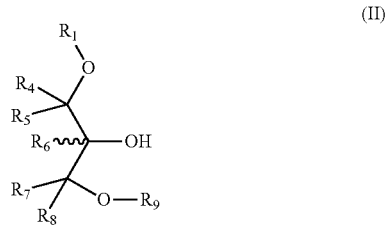

(II)

wherein $R_1$ and $R_4$ to $R_8$ are as described above and $R_9$ is a blocking group, and including racemates or isolated stereoisomers and pharmaceutically acceptable salts or esters thereof. The process involves reacting a compound of formula III:

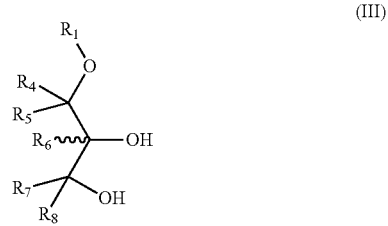

(III)

in a suitable solvent with a nucleophilic catalyst, a base and a blocking agent under conditions to form said compound of formula II, and optionally purifying the resulting compound.

In certain non-limiting embodiments the blocking agent may be a silane blocking agent, for instance a tert-butyldimethylsilyl halide which then gives rise to $R_9$ being a tert-butyldimethylsilyl group.

In other non-limiting embodiments the nucleophilic catalyst may be DMAP, the base may be triethylamine, and the solvent may comprise dimethylformamide (DMF) and $CH_2Cl_2$.

Without wishing to be limiting, it may in certain embodiments be preferred to prepare a solution including the compound of formula III, the nucleophilic catalyst, and the base in the appropriate solvent at from 0 to 5° C. prior to addition of the blocking agent, followed by addition of the blocking agent and then carrying out the reaction at a temperature of from about 15 to about 25° C., for example at about 20° C. The reaction will then preferably be allowed to proceed to completion, which may be up to 20 hours.

Also provided is an intermediate compound according to the structure of formula II:

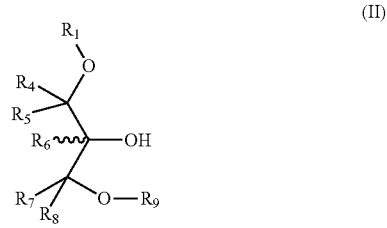

(II)

wherein $R_1$ and $R_4$ to $R_9$ are as described above, including racemates or isolated stereoisomers and pharmaceutically acceptable salts or esters thereof.

BRIEF DESCRIPTION OF THE DRAWINGS

These and other features of the invention will become more apparent from the following description in which reference is made to the appended drawings wherein.

Note that cholesterol levels are significantly elevated (p<0.05) in NRel cells relative to CHO cells and that at 20 μM (PLM-05) decreases membrane free cholesterol and increases membrane cholesterol esters (p<0.05).

Figure 6:
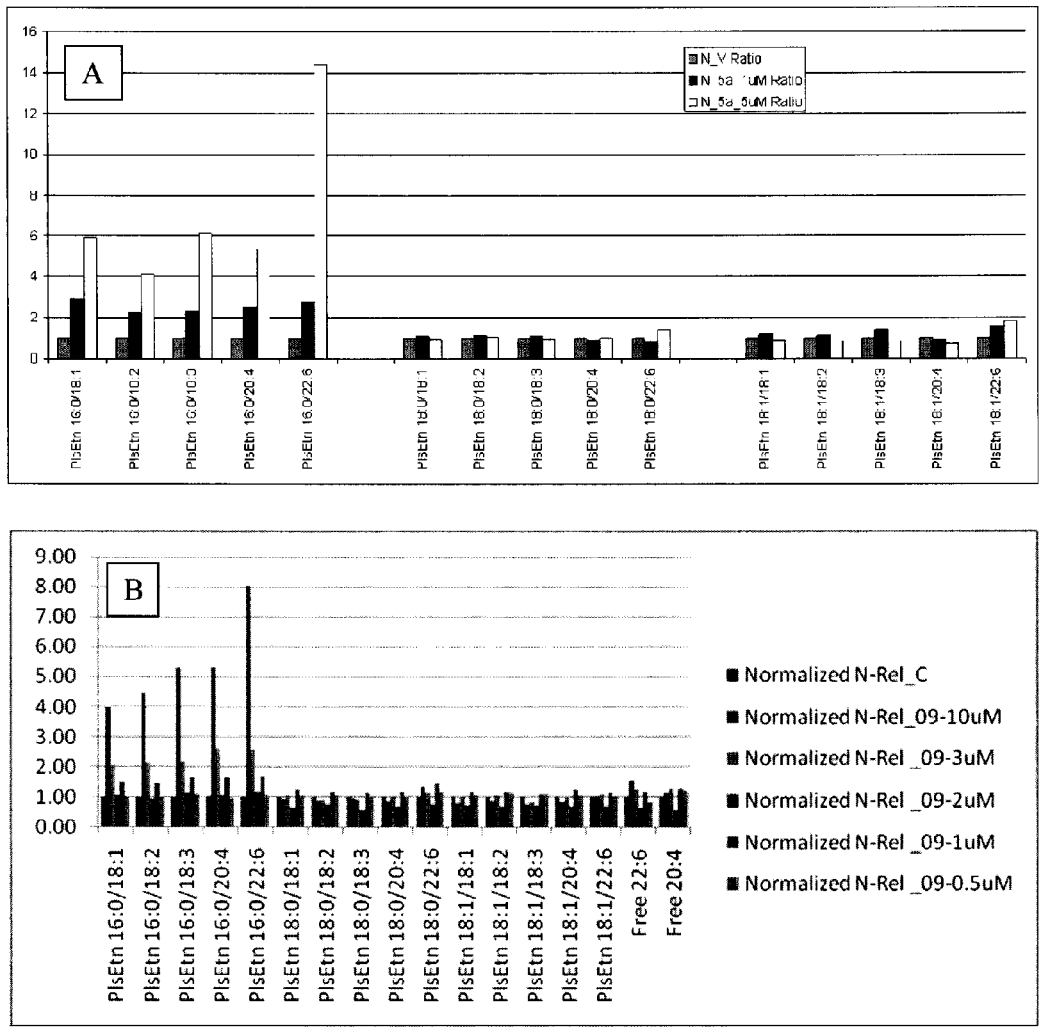

FIG. 6 shows structure-specific and concentration-dependent incorporation (72 hr) into the associated plasmalogen ($R_1$=16:0, $R_2$=22:6, $R_3$=phosphoethanolamine) of N-Rel cells with PPI-1005 (A; 1 and 5 μM) and PPI-1009 (B; 0.5, 1, 2, 3 & 10 μM). The fatty acid substitutions at sn-2 also underwent deacylation and reacylation to form the associated plasmalogens with 20:4, 18:3, 18:2 and 18:1 at sn-2. Cellular plasmalogens were quantitated by LC-MS/MS and normalized relative to N-Rel cells treated with vehicle.

Figure 7:
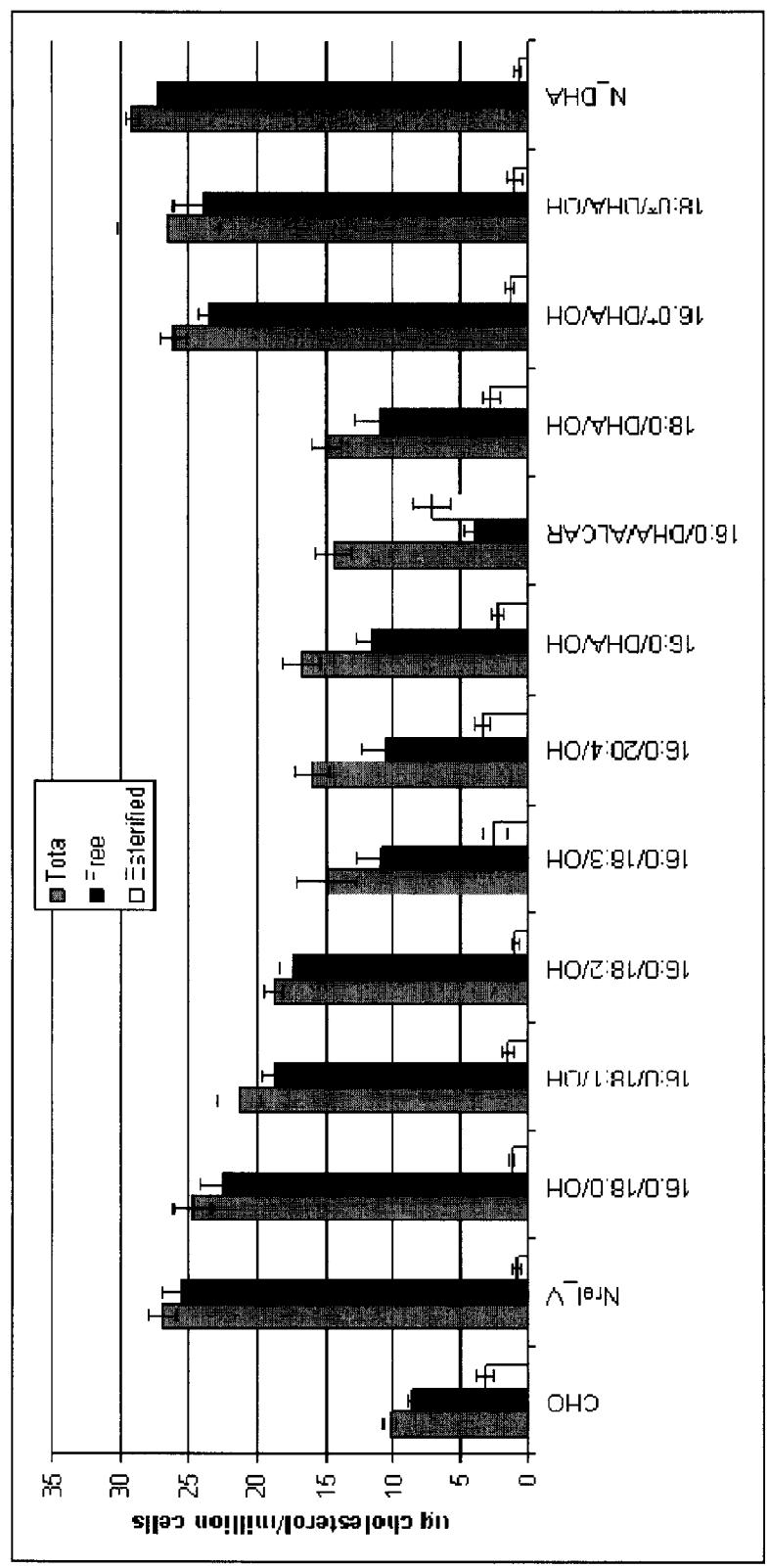

FIG. 7 shows that membrane cholesterol is increased in mutant N-Rel cells relative to control CHO cells. Membrane cholesterol in N-Rel cells is decreased (p<0.05) after a 48 hr incubation (20 μM) with plasmalogen precursors possessing either palmitic (16:0) or stearic (18:0) acid at sn-1 in combination with unsaturated fatty acids, particularly DHA, at sn-2. At 20 μM, free DHA was ineffective in altering membrane free cholesterol levels. In contrast to the activity of analogs with an alkyl linkage at sn-1, the diacyl analog (16:0*:DHA glycerol) was inactive. PPI-1009 (16:0/DHA/ALCAR) produced the most robust decreases in free cholesterol and augmentation of esterified cholesterol. V, vehicle.

Figure 8:
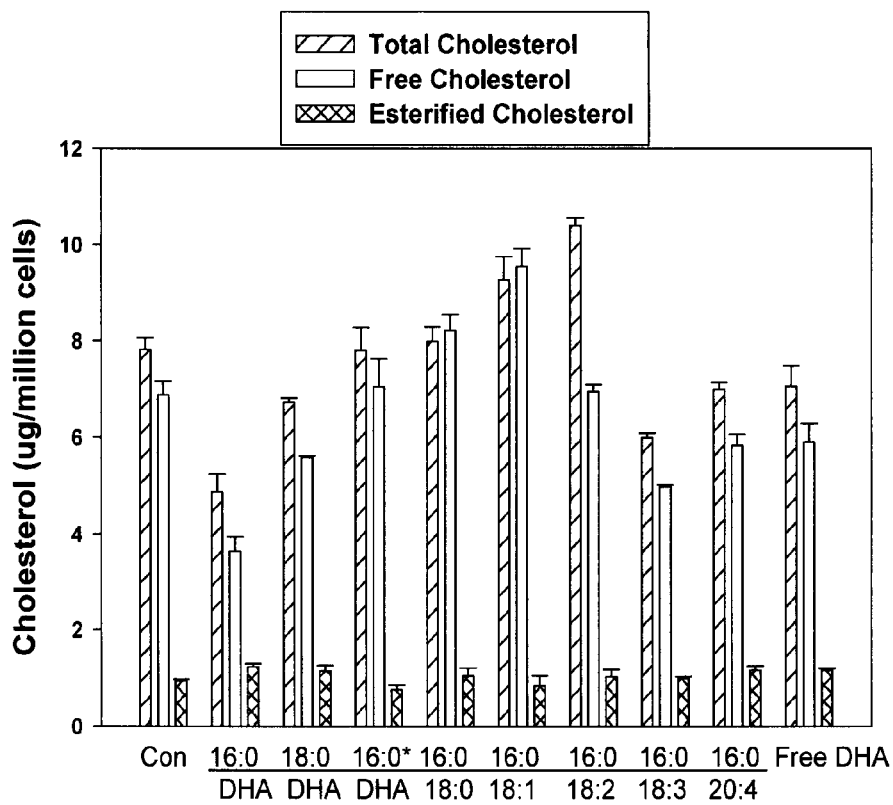

FIG. 8 shows the decrease (p<0.04) in membrane cholesterol in HEK293 cells after a 48 hr incubation with 20 μM 16:0(sn-1 alkyl)/DHA(sn-2 acyl) glycerol, 18:0/DHA glycerol, or 16:0/18:3 glycerol. At 20 μM, 16:0/18:1 glycerol, 16:0/18:2 glycerol, 16:0/20:4 glycerol and free DHA were ineffective in altering membrane free cholesterol levels. In contrast to the activity of analogs with an alkyl linkage at sn-1, the diacyl analog (16:0*:DHA glycerol) was inactive.

Figure 9:
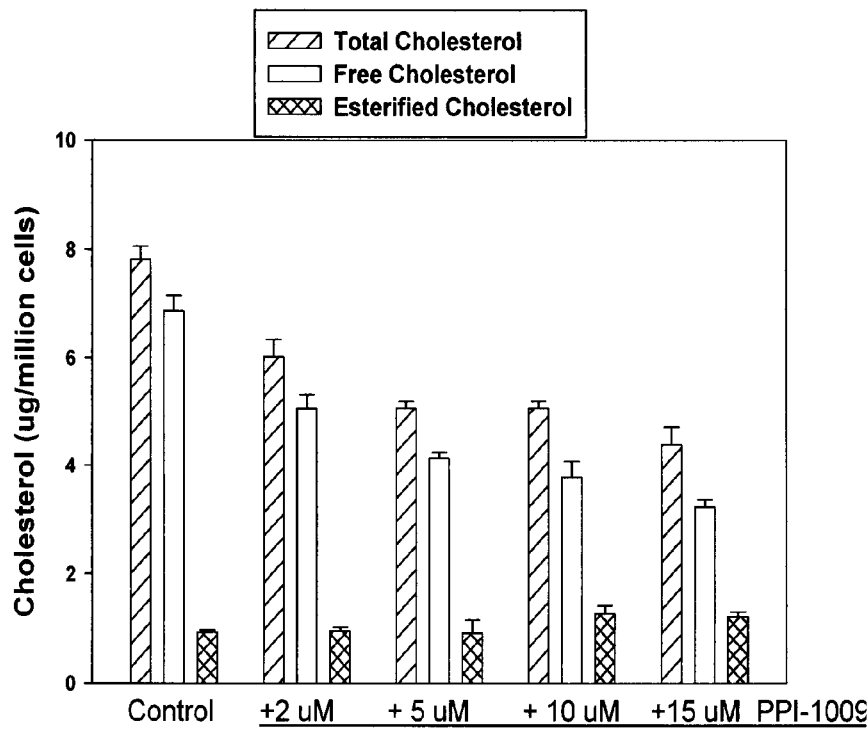

FIG. 9 shows the concentration response for the decrease in membrane cholesterol in HEK293 cells after a 48 hr incubation with 16:0(sn-1 alkyl)/DHA(sn-2 acyl)/acetyl-L-carnitine (sn-3 acyl) glycerol (PPI-1009).

Figure 10:
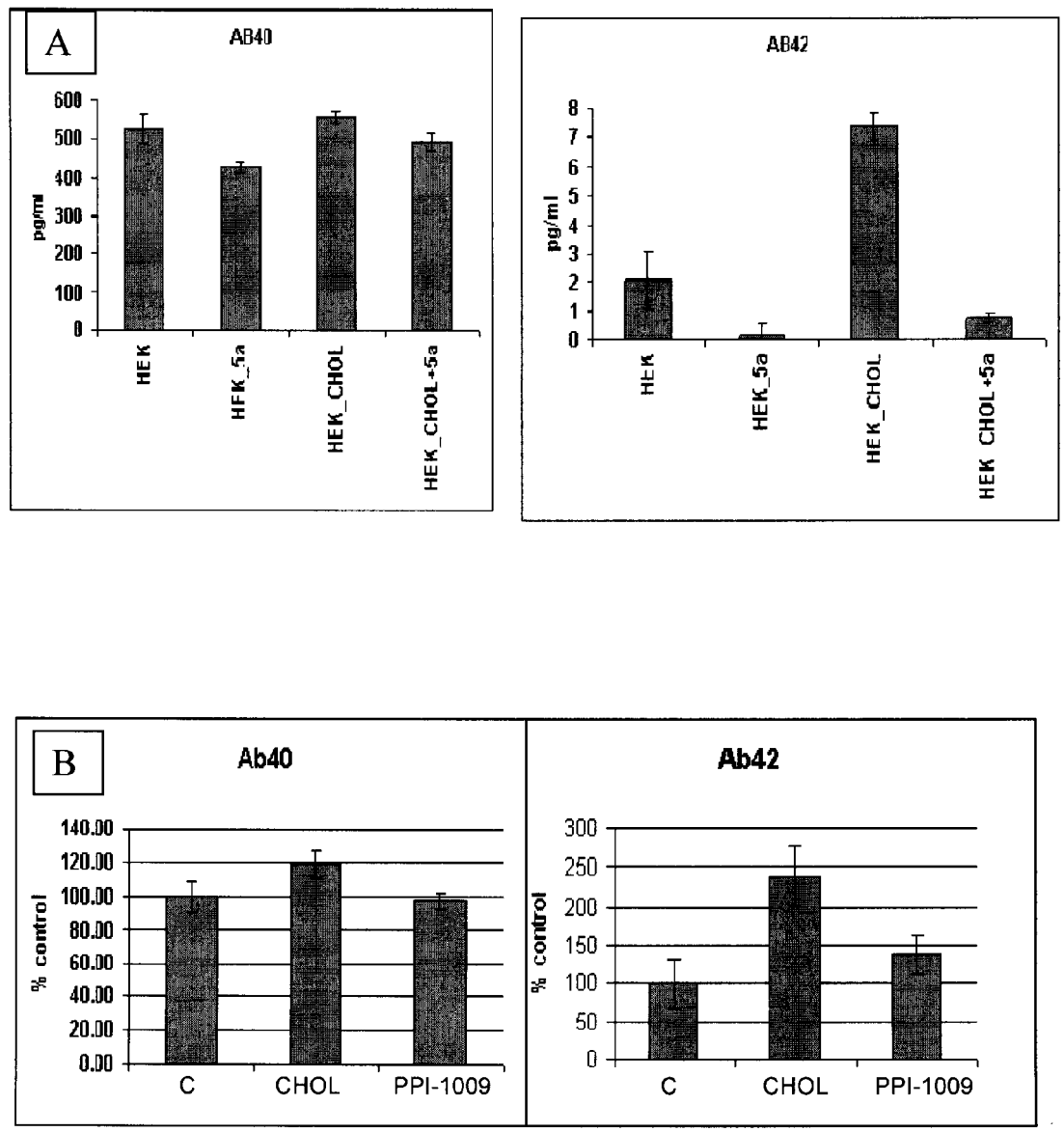

FIG. 10 shows PPI-1005 (5a, 20 μM) decreases basal and cholesterol (25.8 μM)-stimulated Aβ42 secretion by HEK293 cells (A). PPI-1009 (PLM09, 10 μM) acted in a similar manner (B).

Figure 11:
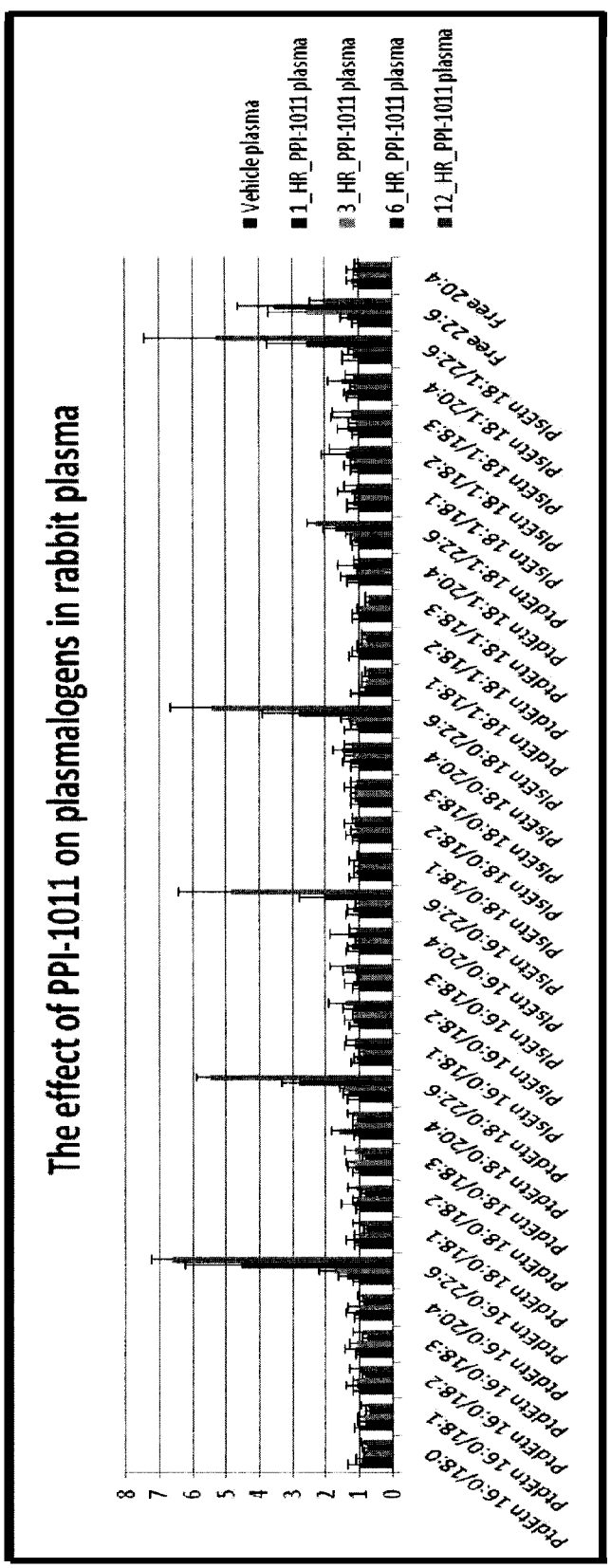

FIG. 11 illustrates the effect of PPI-1011 on plasmalogens in rabbit plasma. PPI-1011 was incorporated into plasma ethanolamine plasmalogens (PlsEtn) and phosphatidylethanolamines (PtdEtn) 1, 3, 6, and 12 hours after a 200 mg/kg dose orally in a gelatin capsule. The release of DHA (free 22:6) from sn-2, via deacylases, was also monitored. Groups consisted of 3 to 5 rabbits.

Figure 12:
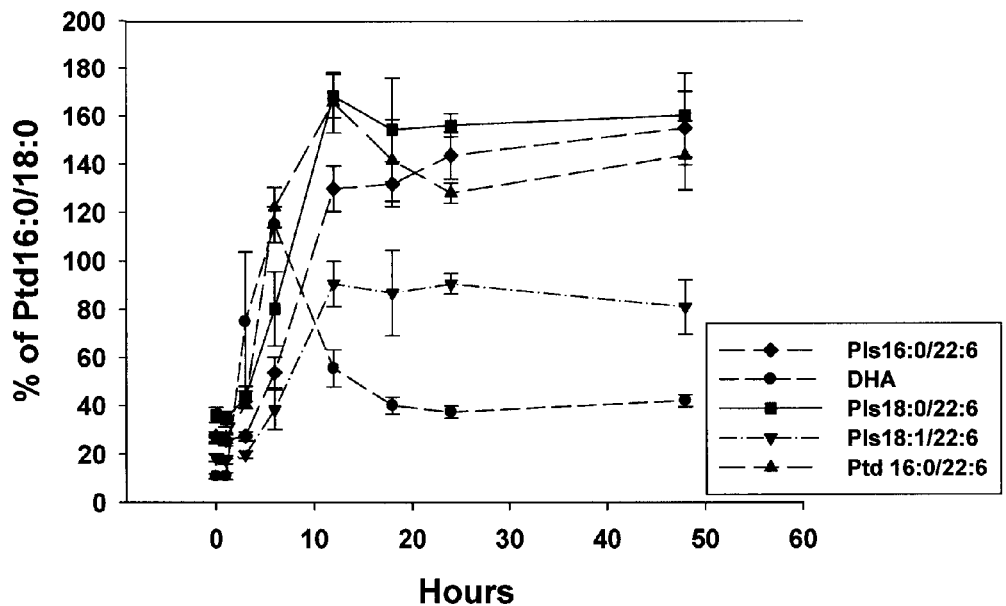

FIG. 12 shows a plot of the timecourse of incorporation of pasmalogen precursor PPI-1011 into circulating Pls 16:0/22:6, DHA, Pls 18:0/22:6, Pls 18:1/22:6 and Ptd 16:0/22:6. Incorporation of PPI-1011 in plasma ethanolamine plasmalogens (Pls) and phosphatidylethanolamines (Ptd) was measured 1, 3, 6, 12, 18, 24 and 48 hours after a 200 to mg/kg dose orally in a gelatin capsule. The release of DHA from sn-2, via deacylases, was also monitored. Groups consisted of 3 to 5 rabbits except the 12 hour timepoint which includes 7 rabbits from 2 separate experiments.

Figure 13:
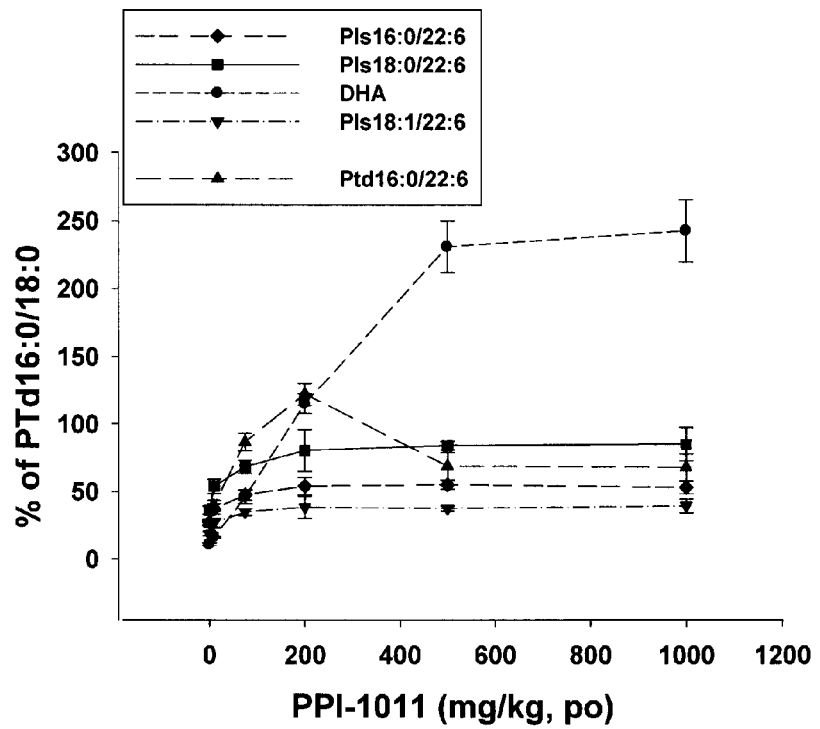

FIG. 13 illustrates the dose-dependent incorporation of PPI-1011 into plasma plasmalogens and phosphatidylethanolamines. Incorporation of PPI-1011 in plasma ethanolamine plasmalogens (Pls) and phosphatidylethanolamines (Ptd) was measured 6 hours after doses of 10, 75, 200, 500, and 1000 mg/kg orally in a gelatin capsule. The release of DHA from sn-2, via deacylases, was also monitored. Groups consisted of 3 to 5 rabbits.

Figure 14:
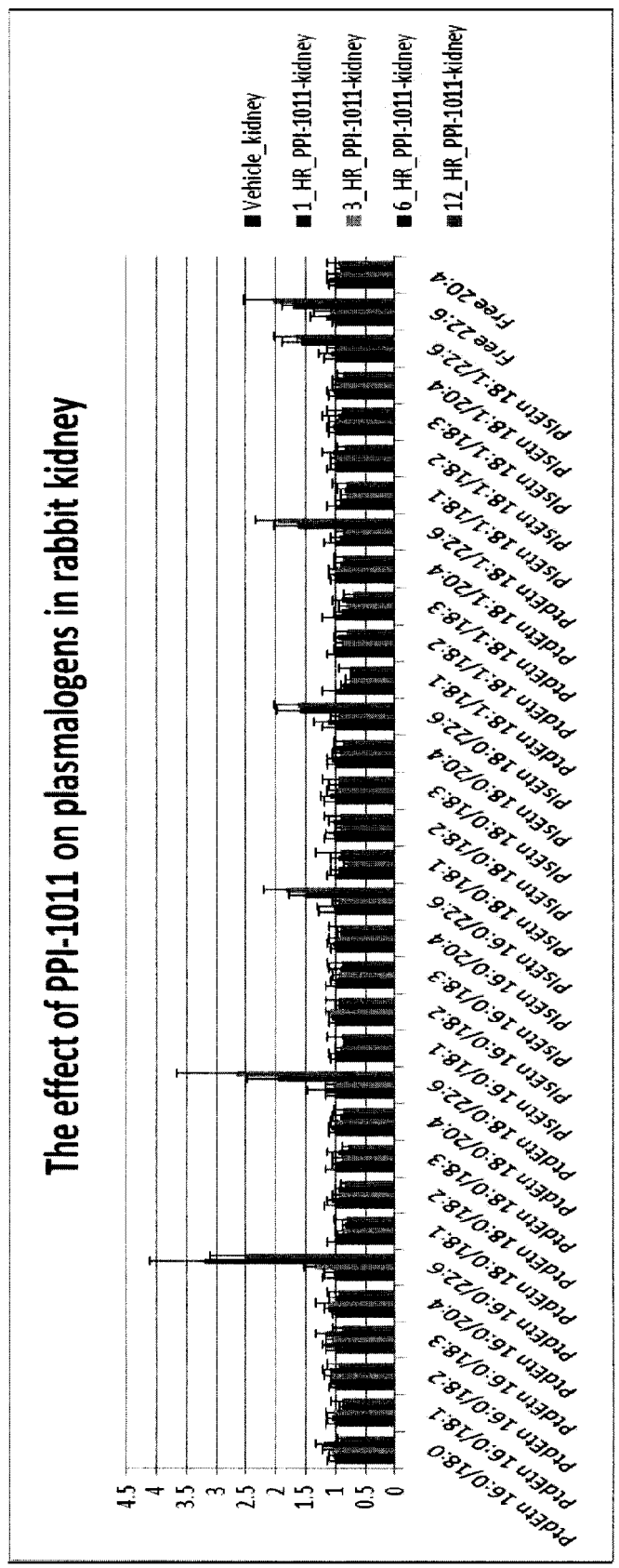

FIG. 14 shows augmentation of tissue plasmalogens and DHA by PPI-1011 in rabbit kidney. Incorporation of PPI-1011 in kidney ethanolamine plasmalogens (P1sEtn) and phosphatidylethanolamines (PtdEtn) was measured 1, 3, 6, and 12 hours after a 200 mg/kg dose orally in a gelatin capsule. The release of DHA (free 22:6) from sn-2, via deacylases, was also monitored. Groups consisted of 3 to 5 rabbits.

Figure 15:
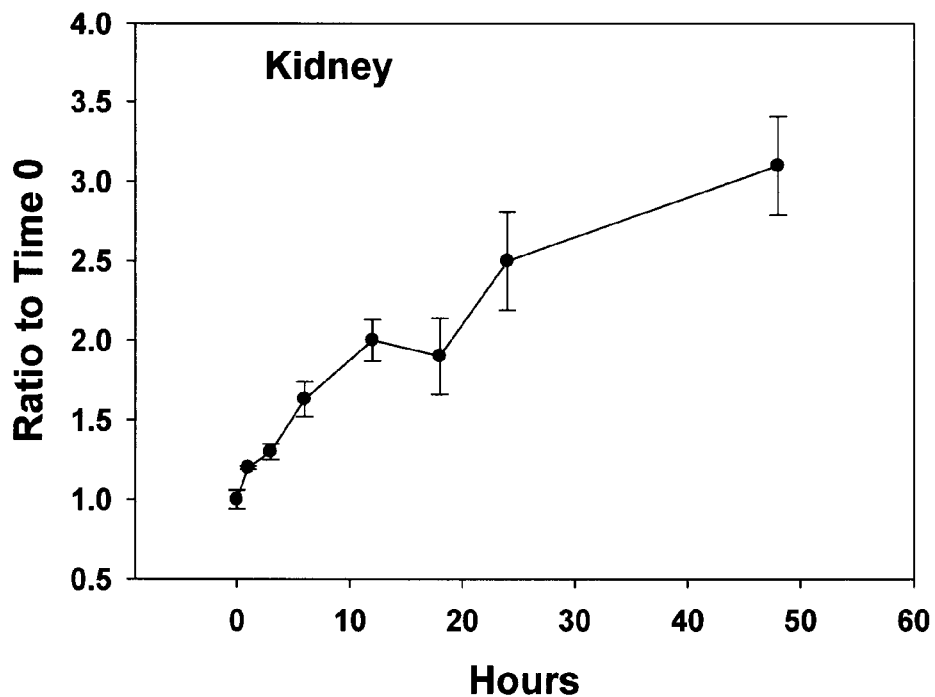

FIG. 15 shows a timecourse of the tissue plasmalogens and DHA augmentation by PPI-1011 in rabbit kidney. Incorporation of PPI-1011 in kidney ethanolamine plasmalogen (16:0/22:6) was measured 1, 3, 6, 12, 18, 24 and 48 hours after a 200 mg/kg dose orally in a gelatin capsule. Groups consisted of 3 to 5 rabbits.

Figure 16:
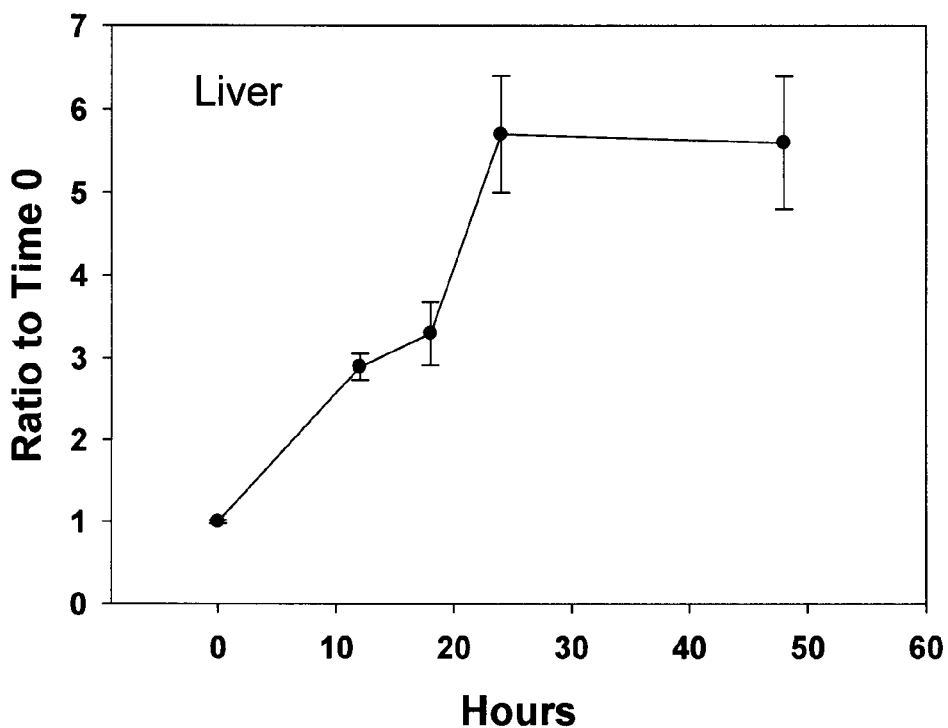

FIG. 16 shows a timecourse of the tissue plasmalogens and DHA augmentation by PPI-1011 in rabbit liver. Incorporation of PPI-1011 in liver ethanolamine plasmalogen (16:0/22:6) was measured 12, 18, 24 and 48 hours after a 200 mg/kg dose orally in a gelatin capsule. Groups consisted of 3 to 5 rabbits.

Figure 17:
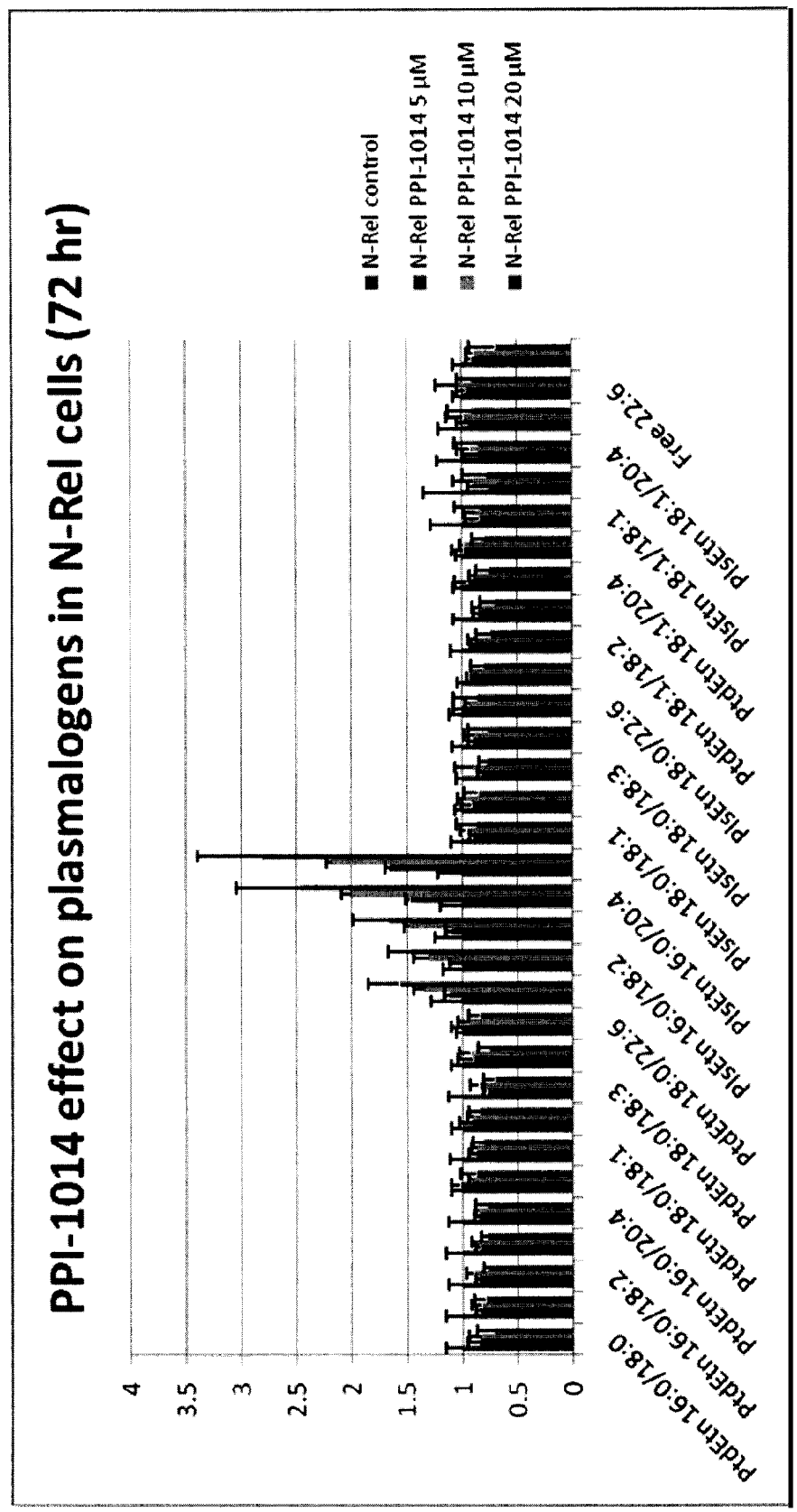

FIG. 17 shows structure-specific and concentration-dependent incorporation of PPI-1014 in N-Rel ethanolamine plasmalogens (P1sEtn) and phosphatidylethanolamines (PtdEtn) after 72 hours (5, 10 and 20 μM). Cellular plasmalogens were quantitated by LC-MS/MS and normalized relative to N-Rel cells treated with vehicle. Groups consisted of three 10 cm² plates.

Figure 18:
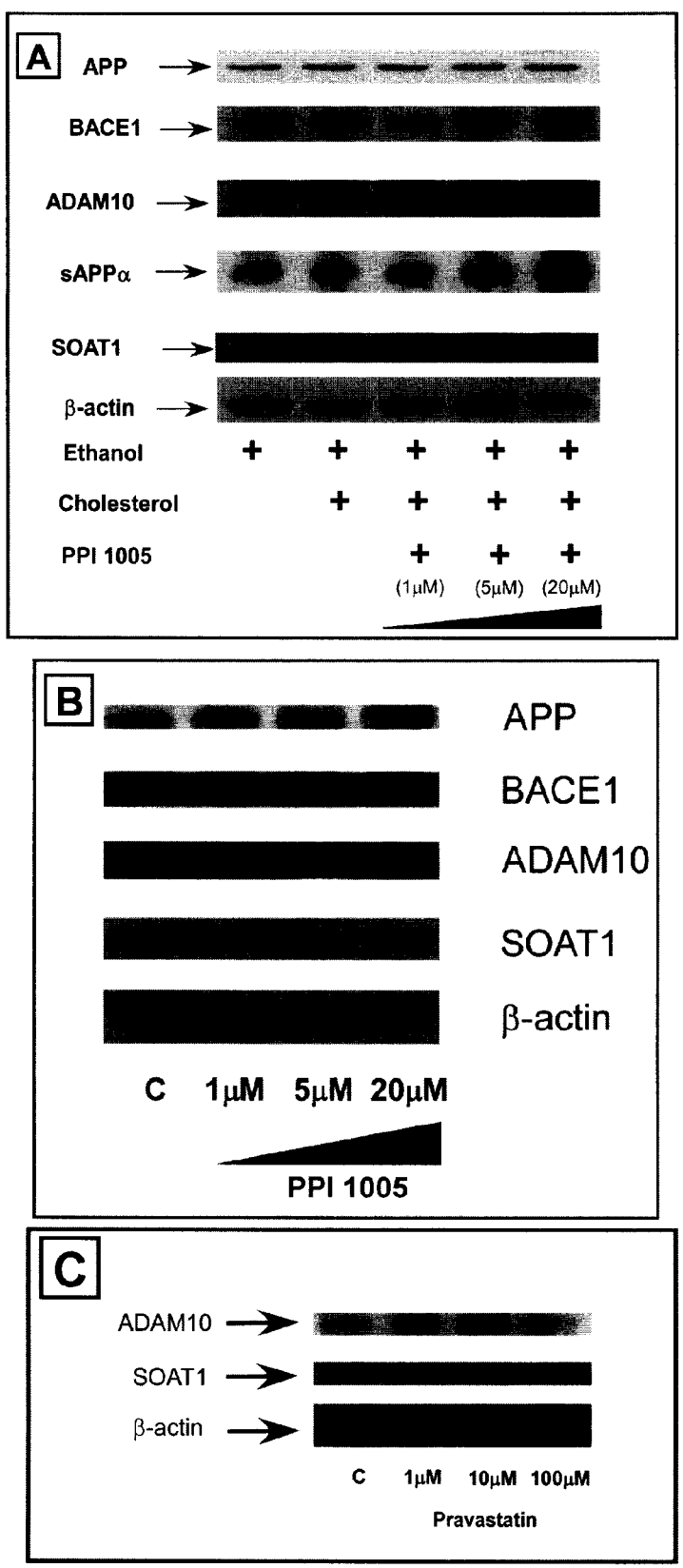

FIG. 18 shows (A) effects of increasing PPI-1005 concentration on membrane resident proteins in cholesterol loaded HEK293 cells, (B) effects of PPI-1005 on membrane resident proteins in wild-type HEK293 cells, and (C) effects of pravastatin on membrane-resident proteins ADAM10 and SOAT1. β-actin was used as a loading control.

DETAILED DESCRIPTION

Described herein are compounds according to structure of formula I:

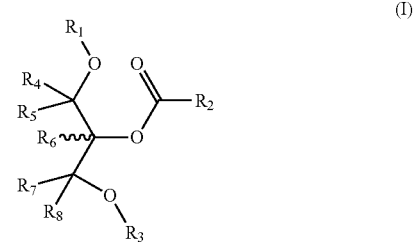

wherein:
$R_1$ and $R_2$ are the same or different and selected from an alkyl or alkenyl hydrocarbon chain selected from the group consisting of: CH3(CH2)3-, CH3(CH2)5-, CH3(CH2)7-, CH3(CH2)9-, CH3(CH2)11-, CH3(CH2)13-, CH3(CH2)15-, CH3(CH2)17-, CH3(CH2)19-, CH3(CH2)21-, CH3(CH2)23-, CH3(CH2)3CH═CH(CH2)7-, CH3(CH2)5CH═CH(CH2)7-, CH3(CH2)7CH═CH(CH2)7-, CH3(CH2)4CH═CHCH2CH═CH(CH2)7-, CH3CH2CH═CHCH2CH═CHCH2CH═CH(CH2)7-, CH3CH2(CH═CH)—, CH3(CH2)3(CH═CH)—, CH3(CH2)5(CH═CH)—, CH3(CH2)7(CH═CH)—, CH3(CH2)9(CH═CH)—, CH3(CH2)11(CH═CH)—, CH3(CH2)13(CH═CH)—, CH3(CH2)15(CH═CH)—, CH3(CH2)17(CH═CH)—, CH3(CH2)19(CH═CH)—, CH3(CH2)21(CH═CH)—, CH3(CH2)3CH═CH(CH2)5(CH═CH)—, CH3(CH2)

5CH=CH(CH2)5(CH=CH)—, CH3(CH2)7CH=CH(CH2)5(CH=CH)—, CH3(CH2)4CH=CHCH2CH=CH(CH2)5(CH=CH), CH3CH2CH=CHCH2CH=CHCH2CH=CH(CH2)5(CH=CH)—, $CH_3(CH_2)_3CH=CH(CH_2)_7$—, $CH_3(CH_2)_5CH=CH(CH_2)_7$—, $CH_3(CH_2)_7CH=CH(CH_2)_7$—, $CH_3(CH_2)_4(CH=CHCH_2)_2(CH_2)_6$—, $CH_3CH_2(CH=CHCH_2)_3(CH_2)_6$—, $CH_3(CH_2)_4(CH=CHCH_2)_4(CH_2)_2$—, $CH_3CH_2(CH=CHCH_2)_5(CH_2)_2$—, $CH_3(CH_2)_7CH=CH(CH_2)_{11}$, and $CH_3CH_2(CH=CHCH_2)_6CH_2$—;

—$R_3$ is a group selected from fatty acids, carnitine, acetyl-D/L-carnitine, thiocarnitine, acetyl-D/L-thiocarnitine, creatine, norcarnitine, phosphocholine, lipoic acid, dihydrolipoic acid, phosphoethanolamine, phosphoserine, N-acetylcysteine, substituted or unsubstituted amino acids and groups of the structures shown below:

1
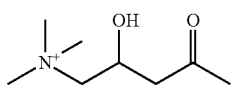

2
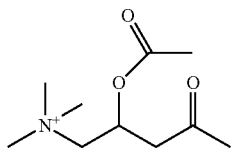

3
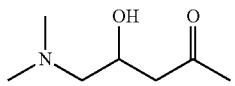

4
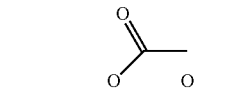

5
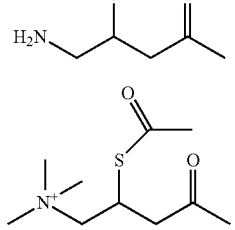

6
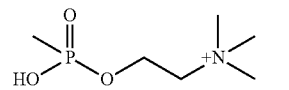

7
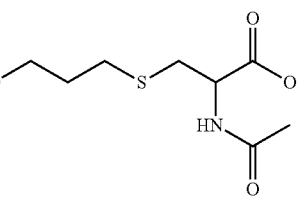

8
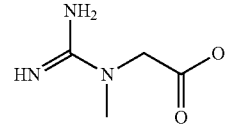

$R_4$ and $R_5$ are independently hydrogen or lower alkyl;
$R_6$ is hydrogen or lower alkyl; and $R_7$ and $R_8$ are independently hydrogen or lower alkyl, and including racemates or isolated stereoisomers and pharmaceutically acceptable salts or esters thereof.

Such compounds are useful for treating or preventing diseases of aging associated with increased membrane cholesterol, increased amyloid or decreased plasmalogen levels.

Such compounds are also useful for treating or preventing diseases of aging mediated by plasmalogen deficiency.

Such compounds can also be used to treat neurodegenerative diseases (including but not limited to Alzheimer's disease, Parkinson's disease and age-related macular degeneration), cognitive impairment, dementia, cancer (including but not limited to prostate, lung, breast, ovarian, and kidney cancers), osteoporosis, bipolar disorder and vascular diseases (including but not limited to atherosclerosis and hypercholesterolemia).

For the purposes of this invention, the hydroxy groups at the sn-1, sn-2, and sn-3 positions of the glycerol back-bone of the compounds of formula I are named using conventional plasmalogen nomenclature, i.e., the oxygen atom of the glycerol bonded to the carbonyl group —C=O(acetyl), —C (form ether bond) and —P (Phosphoryl) is designated in the formula I.

In certain non-limiting embodiments, compounds as described herein may contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the compounds of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Definitions

When describing the alkyl/acyl fatty acids (Table 1, Table 2) and biologically active compounds (Table 3), pharmaceutical compositions and methods of this invention, the following terms have the following meanings unless otherwise specified.

"Fatty acids" are aliphatic monocarboxylic acids, derived from, or contained in esterified form in an animal or vegetable fat, oil or wax. Natural fatty acids commonly have a chain of 4 to 28 carbons (usually unbranched and even numbered), which may be saturated or unsaturated. These are known as acyclic aliphatic carboxylic acids.

Within the meaning of saturated fatty acids, the term "saturated" refers to carbons (apart from the initial carboxylic [—COOH] group) containing as many hydrogens as possible. In other words, the omega (ω) end contains 3 hydrogen atoms ($CH_3$—), and carbon within the chain contains 2 hydrogen atoms.

Unsaturated fatty acids (including but not limited to the examples described in Table 2) are of similar form to saturated fatty acids, except that one or more alkenyl functional groups exist along the chain, with each alkene substituting a single bonded —CH2—CH2— part of the chain with a double-bonded —CH=CH— portion (that is a carbon double-bonded to another carbon). These are named as CIS/TRANS and C:D where C is known as number of carbon atoms and D known as double bond.

"Unsubstituted and substituted amino acids" refers to an optionally substituted amino acid moiety containing an amino group, a carboxylic acid group and a variable side chain, which side chain may include common amino acid side chains, i.e., those used in forming proteins, or others as are known in the art. Protein forming amino acid moieties are particularly preferred, and include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine amino acid groups. Substitutions on the amino acid moieties are also possible, including substitutions with functional groups including but not limited to lower alkyl, acetate, phosphate, lipids and carbohydrates.]

The term "lower alkyl" refers to a cyclic, branched or straight chain monovalent alkyl radical of one to seven carbon atoms ($C_1$-$C_7$), and in certain non-limiting embodiments from one to four carbon atoms ($C_1$-$C_4$). This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted, where a specific example of a substituted alkyl is 1,1-dimethyl heptyl.

"Hydroxyl" refers to —OH.

"Pharmaceutically-acceptable salt" refers to any salt of a compound of this invention which retains its biological properties and which is not biologically or otherwise undesirable. Such salts may be derived from a variety of organic and inorganic counter-ions well known in the art and include, by way of example, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically-acceptable cation" refers to a pharmaceutically acceptable cationic counter-ion of an acidic functional group. Such cations are exemplified by sodium, potassium, calcium, magnesium, ammonium, tetraalkylammonium cations, and the like.

"Pharmaceutically acceptable ester" refers to a conventionally esterified compound of Formula I having a carboxyl group, which esters retain the biological effectiveness and properties of the compounds of Formula I and are cleaved in vivo (in the organism) to the corresponding active carboxylic acid. Information concerning esters and the use of esters for the delivery of pharmaceutical compounds is available in Design of Prodrugs. Bundgaard H ed. (Elsevier 1985). See also, H. Ansel et. al., Pharmaceutical Dosage Forms and Drug Delivery Systems (6th Ed. 1995) at pp. 108-109; Krogsgaard-Larsen, et. al. Textbook of Drug Design and Development (2d Ed. 1996) at pp. 152-191.

A "pharmaceutical agent" or "drug" refers to a chemical compound or composition capable of inducing a desired therapeutic or prophylactic effect when properly administered to a subject.

The term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All chemical compounds include both the (+) and (−) stereoisomers, as well as either the (+) or (−) stereoisomer.

Other chemistry terms herein are used according to conventional usage in the art, as exemplified by The McGraw-Hill Dictionary of Chemical Terms (1985) and The Condensed Chemical Dictionary (1981).

Figure 1:
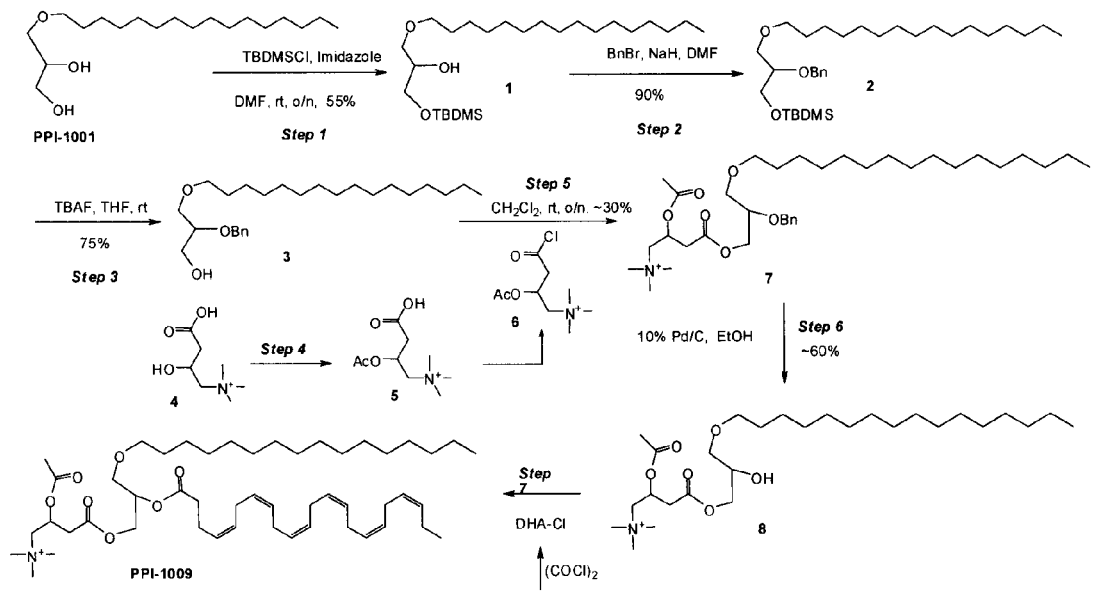
FIG. 1 shows the general experimental procedure for preparation of PPI-1009: 2-acetoxy-4-(2-((4Z,7Z,10Z,13Z,16Z,19Z)-docosa-4,7,10,13,16,19-hexaenoyloxy)-3-(hexadecyloxy)propoxy)-N,N,N-trimethyl-4-oxobutan-1-aminium, in accordance with an embodiment of the present invention.

The compounds described herein, which include plasmalogen precursors derived from a glycerol back-bone with substitution at sn-1 and sn-2 with fatty acids, and sn-3 with fatty acids or endogenous metabolic intermediate compounds, can be prepared from readily available starting materials using the following general methods and procedures shown in FIG. 1. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and de-protection are well known in the art. For example, numerous protecting groups, and their introduction and removal, are described in T. W. Greene and G. M. Wuts, Protecting Groups in Organic Synthesis, Second Edition, Wiley, New York, 1991, and references cited therein.

In a preferred method of synthesis of the compounds described herein, which include glycerol substitutions at sn-1 and sn-2 with fatty acids and sn-3 with fatty acids or endogenous metabolic intermediate compounds as described herein, are prepared by protection/deprotection of hydroxyl groups of the glycerol back-bone with suitable protecting groups, followed by O-alkylation and O-acylation of the compound; for example PPI-1009, PPI-1011 and PPI-1014.

When employed as pharmaceuticals, compounds as described herein are typically administered in the form of a pharmaceutical composition. Such compositions can be prepared using procedures well known in the pharmaceutical art and comprise at least one active compound.

Generally the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The compounds and compositions described herein can be administered to a subject, preferably a mammal, more preferably a human, to treat and/or prevent disease by any suitable routes including, by way of illustration, oral, topical, rectal, transdermal, subcutaneous, intravenous, intramuscular, intranasal, and the like. Depending on the intended route of delivery, the compounds of this invention are preferably formulated as either oral, topical or injectable compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions.

Liquid forms suitable for oral administration may include a suitable aqueous or non aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Topical compositions are typically formulated as a topical ointment or cream containing the active ingredient(s), generally in an amount ranging from about 0.01 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example, an oil-in-water cream base. Such topical formulations are well-known in the art and generally include additional ingredients to enhance the dermal penetration or stability of the active ingredients or the formulation. All such known topical formulations and ingredients are included within the scope of this invention.

The compounds of this invention can also be administered by a transdermal device. Accordingly, topical administration can be accomplished using a patch either of the reservoir or porous membrane type or of a solid matrix variety.

Injectable compositions are typically based upon injectable sterile saline or phosphate-buffered saline or other injectable carriers known in the art. As before, the alkyl nitrone compound in such compositions is typically a minor component, often being from about 0.05 to 10% by weight with the remainder being the injectable carrier and the like.

The above-described components for orally and topically administrable or injectable compositions are merely representative. Other materials as well as processing techniques and the like are set forth in Part 8 of *Remington's Pharmaceutical Sciences*, 18th edition, 1990, Mack Publishing Company, Easton, Pa., 18042, which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The pharmaceutical compositions of this invention can be formulated into tablets, capsules, liquid, injection formulation, or an ointment. The present invention, however, is not limited to the following pharmaceutical compositions. For example, yet without wishing to be limiting in any way, the compound of formula I can be dissolved in a buffered sterile saline injectable aqueous medium to a appropriate concentration of approximately 5 mg/mL.

The invention also encompasses kits that can simplify the administration of a pharmaceutically active agent to an animal. A typical kit of the invention comprises a unit dosage form of a pharmaceutical composition according to the invention. In one embodiment, the unit dosage form is a container (such as a vial, a pouch, a tube, a syringe, or the like), which can advantageously be sterile, containing a pharmaceutical composition of the invention. The kit can further comprise a label or printed instructions instructing the use of the pharmaceutically active agent to treat or prevent a condition. In another embodiment, the kit comprises a unit dosage form of a pharmaceutical composition of the invention and a dropper, syringe, or other applicator for administering the pharmaceutical composition. Typically, the components of the kit, for example, the unit dosage form and instructions, are contained within a suitable packaging material.

Herein it is shown that bioavailable plasmalogen precursors with docosahexaenoic acid (22:6) substitution at sn-2 decreased membrane cholesterol levels. In contrast, stearic acid (18:0), oleic acid (18:1), linoeic acid (18:2), arachidonic acid (20:4) or linolenic (18:3), at sn-2, were much less active and free DHA was inactive. The fatty acid substitution at sn-1 demonstrated an absolute requirement for an alkenyl linkage, with an acyl linkage completely eliminating cholesterol-lowering activity. The alkenyl linkage can be generated in the endoplasmic reticulum from the alkyl precursor (e.g. PPI-1009); however, the synthetic alkenyl form could also be a potential therapeutic molecule. The pharmaceutical properties of these targeted plasmalogen precursors can also be improved with the addition of a polar substituent to sn-3. This substitution provides improved pharmaceutical properties including: i) stabilization of the sn-2 substitution from migration to sn-3[27-28] ii) the ability to generate a pharmaceutically-acceptable salt to improve formulation and drug dissolution and absorption; and iii) the ability of sn-3 substituents to be readily removed by lipases[29] such that the precursor can be converted to the corresponding endogenous plasmalogen.

Accordingly, administering compounds of the present invention to mammalian biological systems results in increased cellular concentrations of specific sn-2 substituted ethanolamine plasmalogens independent of the ether lipid synthesis capacity of the system. The elevated levels of these specific sn-2 substituted species give rise to lowering of membrane cholesterol levels and lowering of amyloid secretion, therefore making these compounds useful for the treatment or prevention of diseases of aging associated with increased membrane cholesterol, increased amyloid, and decreased plasmalogen levels.

Without wishing to be bound by theory, it is believed that the compounds described herein are capable of bypassing peroxisomal ether lipid biosynthesis pathways enabling both the restoration of plasmalogen levels in plasmalogen deficient subjects, as well as the delivery of pharmaceutically effective cholesterol lowering levels of specific cholesterol lowering plasmalogens. Accordingly, these molecules can be used to treat or prevent diseases associated with either decreased levels of plasmalogens, increased levels of membrane cholesterol or increased amyloid levels. These factors are believed to be causal in a wide variety of human diseases such as neurodegeneration (including without limitation Alzheimer's disease, Parkinson's disease and age-related macular degeneration), cognitive impairment, dementia, cancer (including without limitation prostate, lung, breast, ovarian, and kidney cancer), osteoporosis, bipolar disorder and vascular diseases (including but not limited to atherosclerosis and hypercholesterolemia). Accordingly, the present invention relates to the treatment of these diseases using the described plasmalogen precursors. Furthermore, these derivatives have utility in the treatment of disorders resulting from abnormal genetic expression of cholesterol transport proteins such as apolipoprotein E.

It is also shown herein that the administration of 1-alkyl-2-alkyl glycerols result in the stereoselective elevation of PlsEtn levels in both PlsEtn normal and PlsEtn deficient systems. These data also demonstrate for the first time that 1-alkyl, 2-acylglycerols reduce membrane cholesterol levels and amyloid levels and that these effects require specific fatty acid substitutions at the sn-2 position.

The inventors also demonstrate herein that:
1) the ether bond at sn-1 is stable and is further processed by a desaturase (endoplasmic reticulum) to generate the essential alkenyl bond at sn-1 characteristic of plasmalogens but that this desaturation occurs after the addition of phosphoethanolamine by CDP-ethanolamine transferase (endoplasmic reticulum);
2) the charged substitution at sn-3 stabilizes the fatty acid substitution at sn-2 from migrating[27-28] to sn-3;
3) the charged substitution at sn-3 is readily cleaved by cellular lipases and provides the free hydroxyl group for the addition of phosphoethanolamine by CDP-ethanolamine transferase (endoplasmic reticulum);
4) the fatty acid substituent at sn-2 is able to undergo deacylation and reacylation by other fatty acids in cells;
5) DHA substitution at sn-2 is optimal for lowering membrane cholesterol, and
6) the charged substitution at sn-3 improves the pharmaceutical properties (stability, bioavailability and formulation as a salt) of the novel presented plasmalogen precursors.

The compounds of the present invention are effectively converted to PlsEtn species in cells with impaired plasmalogen biosynthesis capacity and in cells with unimpaired plasmalogen biosynthesis capacity. These results are in direct contrast to the prior art regarding other plasmalogen precursors. 1-alkyl, 2-hydroxy glycerols (chimyl, batyl, salachyl alcohols) have been shown to increase PlsEtn levels in PlsEtn deficient systems to control levels but not to above control levels in either PlsEtn deficient or PlsEtn sufficient systems. Therefore, the compounds of the present invention can be useful in the prevention of diseases of the aging mediated by plasmalogen deficiency, but increasing PlsEtn levels to above control levels in either PlsEtn deficient or PlsEtn sufficient systems.

As discussed above, the compounds described herein are suitable for use in a variety of drug delivery systems; however, without wishing to be limiting, the compounds are especially useful for oral delivery in a capsule or tablet. In such embodiments the maximum total dose is not expected to exceed 2g/day for a 40 to 80 kg human patient.

In the following examples the following abbreviations have the following meanings. Abbreviations not defined below have their generally accepted meaning.
bd=broad doublet
bs=broad singlet
d=doublet
dd=doublet of doublets
dec=decomposed
dH$_2$O=distilled water
ELISA=enzyme-linked immuno-sorbent assay
EtOAc=ethyl acetate
EtOH=ethanol
g=grams
h=hours
Hz=hertz
ip=intraperitoneal
L=liter
m=multiplet
min=minutes
M=molar
MeOH=methanol
mg=milligram
MHz=megahertz
mL=milliliter
mmol=millimole
m.p.=melting point
N=normal
po=per os, oral
q=quartet
quint.=quintet
s=singlet
t=triplet
THF=tetrahydrofuran
tlc=thin layer chromatography
µg=microgram
µL=microliter
UV=ultraviolet In the examples below, all temperatures are in degrees Celsius unless otherwise indicated.

The following synthetic and biological examples are offered to illustrate this invention and are not to be construed in any way as limiting the scope of this invention.

EXAMPLES

Example 1

Chemical Synthesis

PPI-1009: 2-acetoxy-4-(2-((4Z,7Z,10Z,13Z,16Z,19Z)-docosa-4,7,10,13,16,19-hexaenoyloxy)-3-(hexadecyloxy) propoxy)-N,N,N-trimethyl-4-oxobutan-1-aminium was prepared according to the following general experimental procedure.

Step-1

At 0° C., to a solution of unlabelled PPI-1001 (50 g, 158 mmol) in dry DMF (20 mL), was added imidazole (21.5 g, 316 mmol), the resulting mixture stirred for 10 min. A solution of TBDMS-Cl (26.2 g, 174 mmol) in DMF (50 mL) was added drop wise and the resulting solution was stirred at rt for 4 h. The reaction mixture was diluted with water (50 ml), extracted with EtOAc (2×250 mL). The organic layer washed with ice water (2×100 mL), brine (50 mL), dried (Na$_2$SO$_4$) and evaporated to obtain crude compound 4 that was purified by column chromatography (neutral alumina, EtOAc-Pet ether (0.5:9.5) to obtain compound 3 (45g, 66%). R$_f$=0.65 (EtOAc-Pet ether (1-9))

Step-2

At 0° C., to a solution of compound 3 (75 g, 174 mmol) in DMF (750 mL) NaH (60% dispersion in oil, 5g, 209 mmol) was added portion wise, stirred for 30 min, benzyl bromide (44.8 g, 262 mmol) added drop wise over a period of 1 h, slowly allowed to rt and stirred overnight until complete consumption of compound 3 as evidenced by tlc analysis. The reaction mixture was cooled to 0° C., methanol (5 mL), ice cold water (50 mL) added, extracted with Et$_2$O (2×250 mL), organic layer washed with water (2×50 mL), brine (50 mL), dried (Na$_2$SO$_4$) and evaporated to obtain crude compound 4 (90g) as yellow oil (R$_f$=0.7; EtOAc-Pet ether [5-95]), that was used as such for the next step without further purification.

Step-3

At −15° C., to a solution of compound 4 (1.7 g, 3.26 mmol) in dry THF (15 mL), a solution of TBAF (1.7 g, 6.53 mmol) in dry THF (5 mL) added and the reaction mixture slowly warmed to rt and stirred overnight until complete consumption of compound 4 as evidenced by tlc analysis. The reaction mixture was quenched with water (10 mL), extracted with EtOAc (2×50 mL), organic layer washed with brine (20 mL), dried (Na$_2$SO$_4$) and evaporated to obtain crude compound 6 that was purified by flash column chromatography (100-200 mesh silica gel, EtOAc-Pet ether(3:7) to obtain compound 5 (850 mg, 65%) as a light yellow oil. R$_f$=0.54 (EtOAc-Pet ether (3:7).

Step-4

At 0° C., to a solution of compound 7 (8 g, 39 mmol) in dry CH$_2$Cl$_2$(50 mL)-DMF (3 drops) oxalyl chloride (4.2 mL, 40 mmol) was added and resulting mixture slowly warmed to rt stirred for 5 h. Excess oxalyl chloride was evaporated and residue dissolved in toluene and solvent evaporated to obtain compound 6. A solution of compound 6 in dry $CH_2Cl_2$ (25 mL) was added dropwise to a solution of compound 5 (11 g, 20 mmol) in dry $CH_2Cl_2$ (50 mL) and the resulting solution purged with Argon gas till complete consumption of compound 5 as evidenced by tlc analysis. The reaction mixture was concentrated to obtain crude compound 8 (14g) that was used as such for the next step without further purification. $R_f$=0.45 (MeOH—$CHCl_3$ (1:4)).

Step-5

A solution of compound 8 (14g crude) in EtOH (50 mL), was hydrogenated over 10% Pd/C at 40 psi, until complete consumption of compound 8 as indicated by TLC analysis. The reaction mixture was filtered and evaporated to obtain crude compound 9, which was purified by column chromatography over neutral alumina to give compound 9 (6g, 6g, 61% over two steps) as a light brown oil $R_f$=0.25 (MeOH—$CHCl_3$ (2:3)).

Step-6

At 0° C., to a solution of compound 9 (8.2 mg, 16 mmol) in THF (150 mL), catalytic amount of DMAP (1.9 g, 20 mmol), pyridine (7.6 mL, 90 mmol) were added and stirred at rt for an hour. To this solution, a solution of DHA-Cl (prepared by addition of a solution of oxalyl chloride (2.5 mL, 28 mmol) in dry $CH_2Cl_2$ at 0° C. to DHA-acid (7.7 g, 20 mmol), evaporating excess oxalyl chloride to give DHA-Cl) in $CH_2Cl_2$ (50 mL) was added drop wise to the reaction mixture at 0° C. and stirred for 0.5 h. The reaction mixture was slowly warmed to rt and stirred for 24 h. The reaction mixture was diluted with water (50 mL), extracted with EtOAc (2×200 mL), washed with brine (50 mL) dried ($Na_2SO_4$) and evaporated to obtain crude that was purified by column chromatography (neutral alumina MeOH—$CHCl_3$(5:95)) to obtain PPI-1009 (1.2 g, ~10%, HPLC purity 97% along with 1.7 g of impure material) as a light brown semisolid $R_f$=0.45 (MeOH—$CHCl_3$ (15:85)).

Example 2

Biological Testing

Chinese hamster ovary (CHO), N-Rel[30] (a mutant CHO cell line deficient in the peroxisomal enzyme dihydroxyacetonephosphate acyltransferase), and human embryonic kidney (HEK293) cells were grown in 10 cm² dishes in DMEM/Ham's F12 (1:1) containing 10% FBS. Cells were incubated with plasmalogen precursors dissolved in ethanol (final ethanol concentration of 0.1%) and harvested for plasmalogen analysis by LC-MS-MS[31], and cholesterol and cholesterol ester analyses utilizing a commercial colorimetric kit (BioVision #K613).

Figure 2:
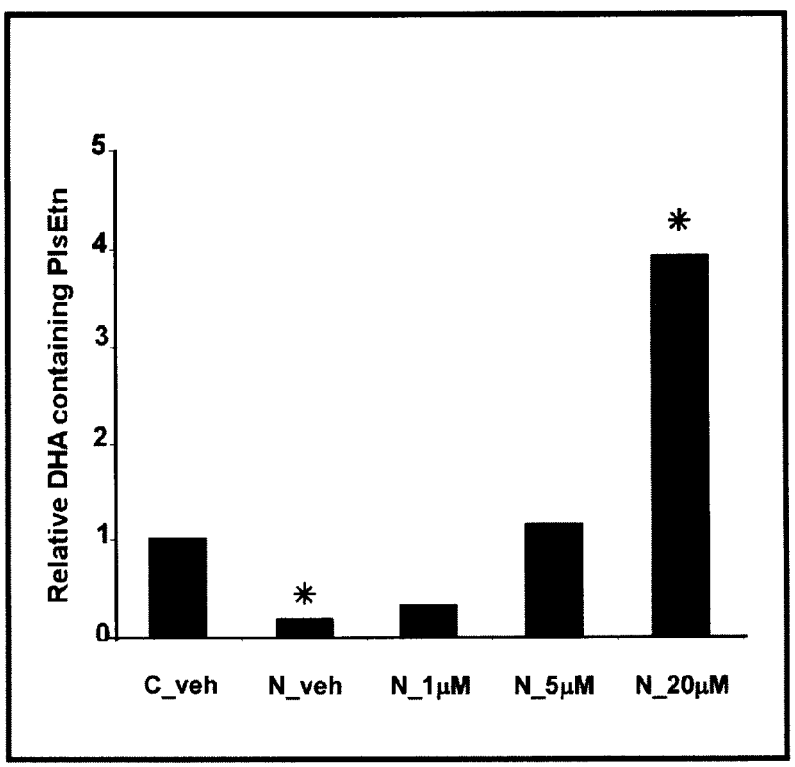
FIG. 2 shows decreased levels of total DHA plasmalogens in N-Rel cells, relative to control CHO cells, are restored in a concentration-dependent manner by PPI-1005 ($R_1$=16:0; $R_2$=DHA; $R_3$=OH). 72 hr incubation. * p<0/05 vs. vehicle (veh).
Figure 3:
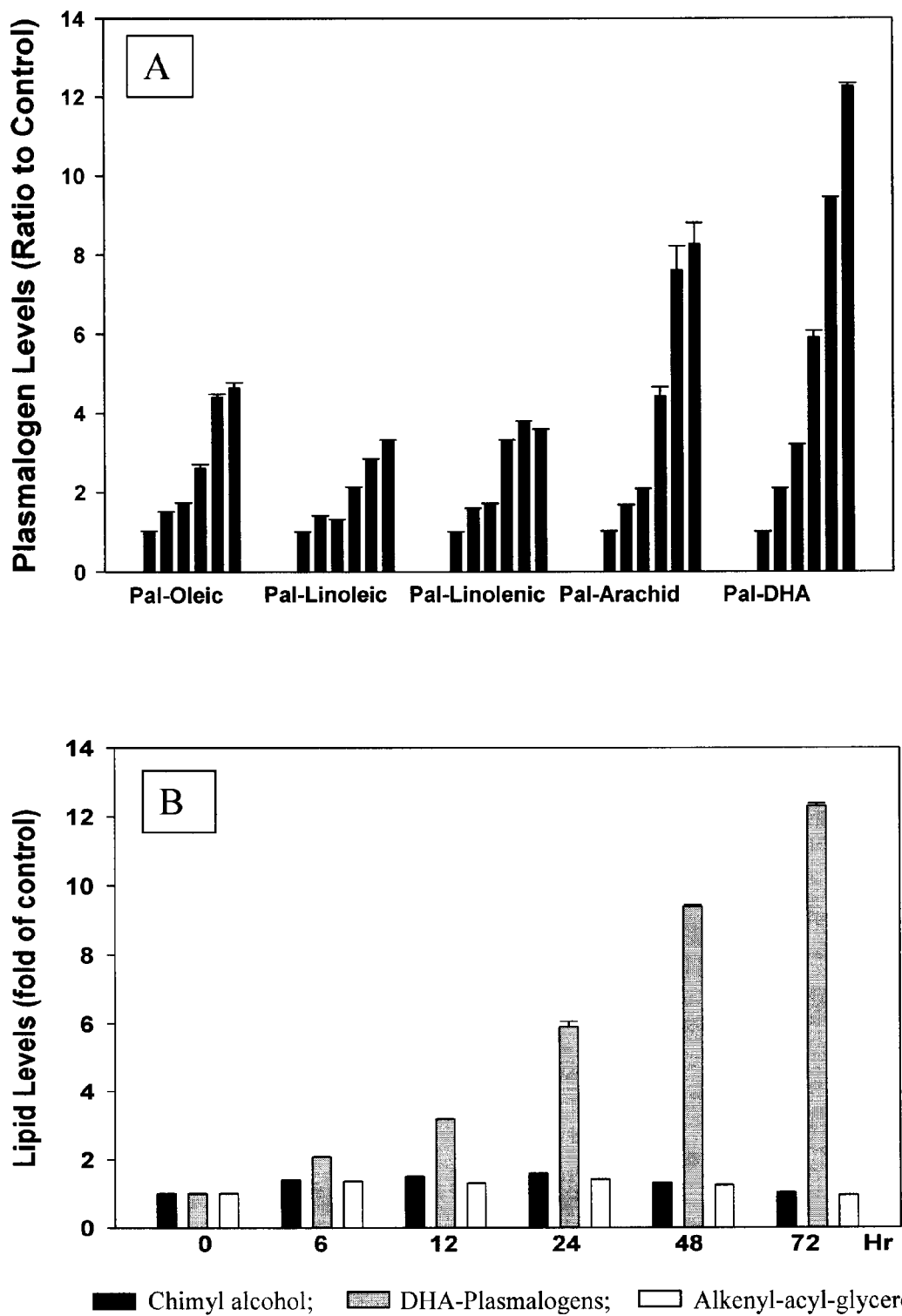
FIG. 3 shows (A) a time course of PPI-1009 (10 µM) incorporation into plasmalogens and lack of effect on cellular levels of chimyl alcohol or the associated alkenyl-acyl-glycerol (B) of N-Rel cells (0, 6, 12, 24, 48 and 72 hr). Cellular plasmalogens and docosahexaenoic (DHA) acid were quantitated by LC-MS/MS while chimyl alcohol was quantitated by GC-MS.
Figure 4:
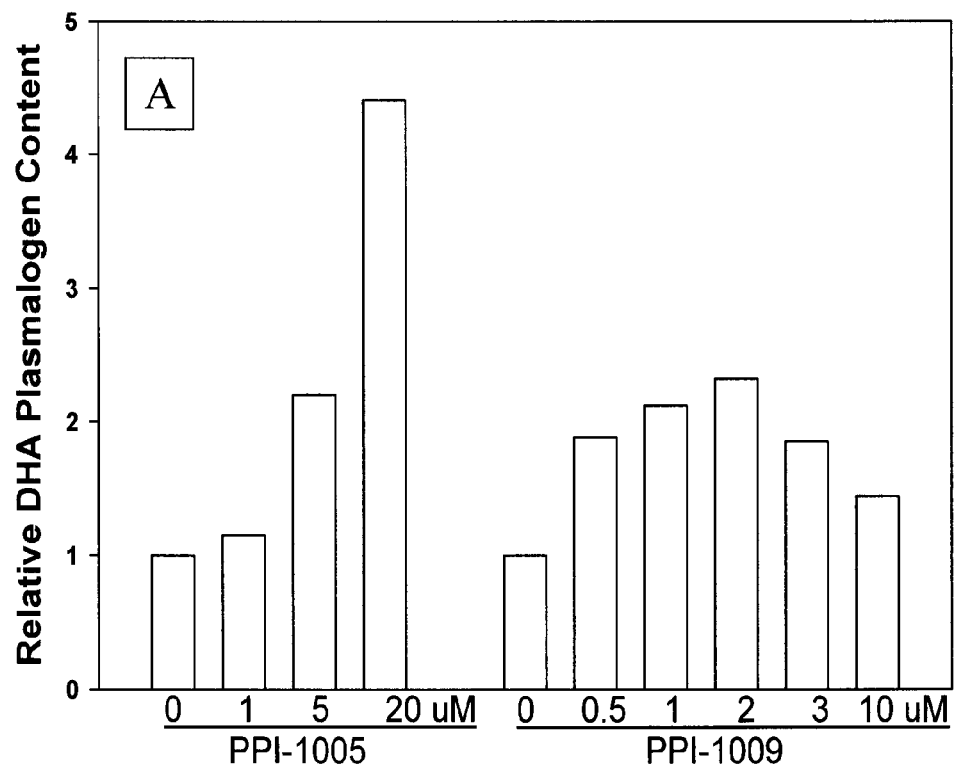
FIG. 4 shows (A) the concentration-dependent (72 hr) increase of DHA plasmalogens in CHO cells with PPI-1005 and PPI-1009. While chimyl alcohol increased DHA-plasmalogens in N-Rel cells there was no effect in CHO cells (B). Cellular plasmalogens were quantitated by LC-MS and expressed relative to CHO controls or N-Rel controls.
Figure 4:
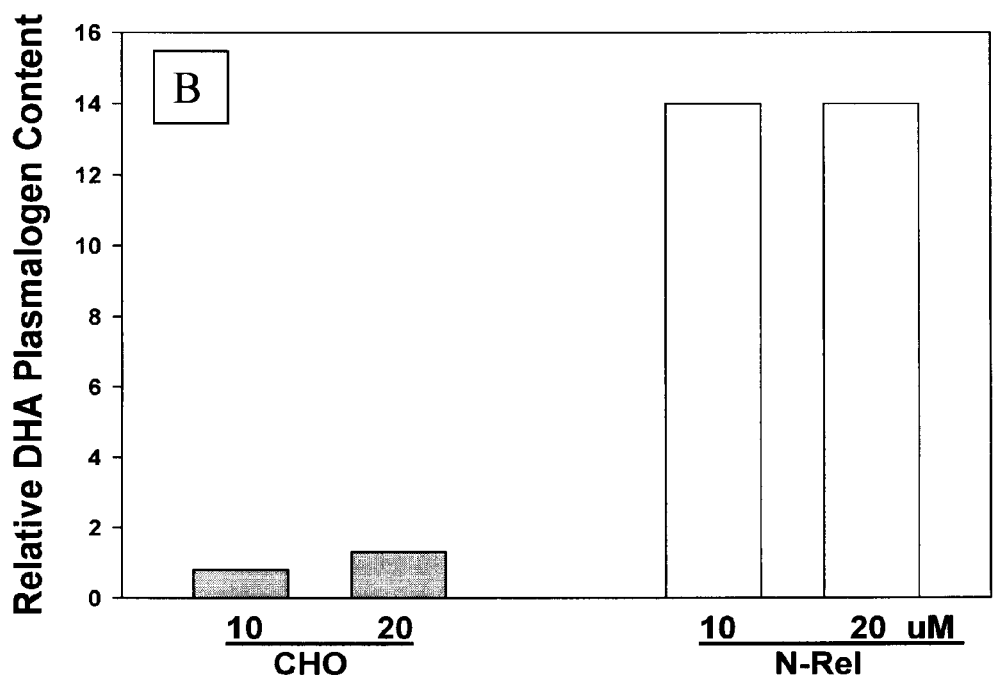

1-alkyl, 2-acyl glycerols with 16:0 at sn-1, DHA at sn-2 and either OH or acetyl-L-carnitine at sn-3, PPI-1005 or PPI-1009, respectively were effectively converted to PlsEtn species in cells with impaired plasmalogen biosynthesis capacity (N-Rel, FIGS. 2, 3A) and in cells with unimpaired plasmalogen biosynthesis capacity (CHO, FIG. 4A). These results are in direct contrast to the prior art regarding other plasmalogen precursors. 1-alkyl, 2-hydroxy glycerols (chimyl, batyl, salachyl alcohols) has been shown to increase PlsEtn levels in PlsEtn deficient systems to control levels but not to above control levels in either PlsEtn deficient or PlsEtn sufficient systems (FIG. 4B). In addition the bioconversion of the 1-alkyl, 2-acyl glycerols described in this invention did not result in increased levels of either chimyl alcohol or 1-alkenyl, 2-acyl glycerols (FIG. 3B) indicating that neither chimyl alcohol nor 1-alkenyl, 2-acyl glycerols are intermediates in the biotransformation pathway of the described molecules to PlsEtn.

The compound PPI-005 is described in applicant's co-pending application PCT/CA2007/001472, and is shown below:

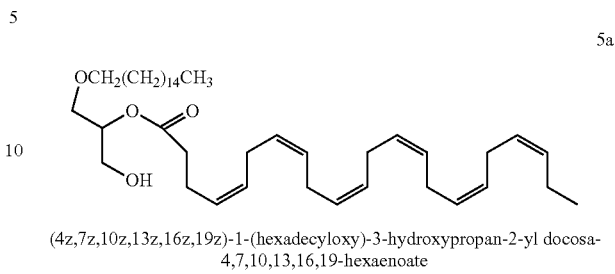

(4z,7z,10z,13z,16z,19z)-1-(hexadecyloxy)-3-hydroxypropan-2-yl docosa-4,7,10,13,16,19-hexaenoate Treatment of cells with 1-alkyl, 2-acyl glycerols with 16:0 at sn-1, DHA at sn-2 and either OH or acetyl-L-carnitine at sn-3 resulted in the structure-specific enrichment of PlsEtn with DHA at sn-2 (FIG. 6). This is the first description of the structure-specific enrichment of PlsEtn.

PPI-1009 is a plasmalogen precursor with improved pharmaceutical properties. This molecule exists at room temperatures as a salt and represents the first non-oil based plasmalogen precursor ever reported.

Figure 5:
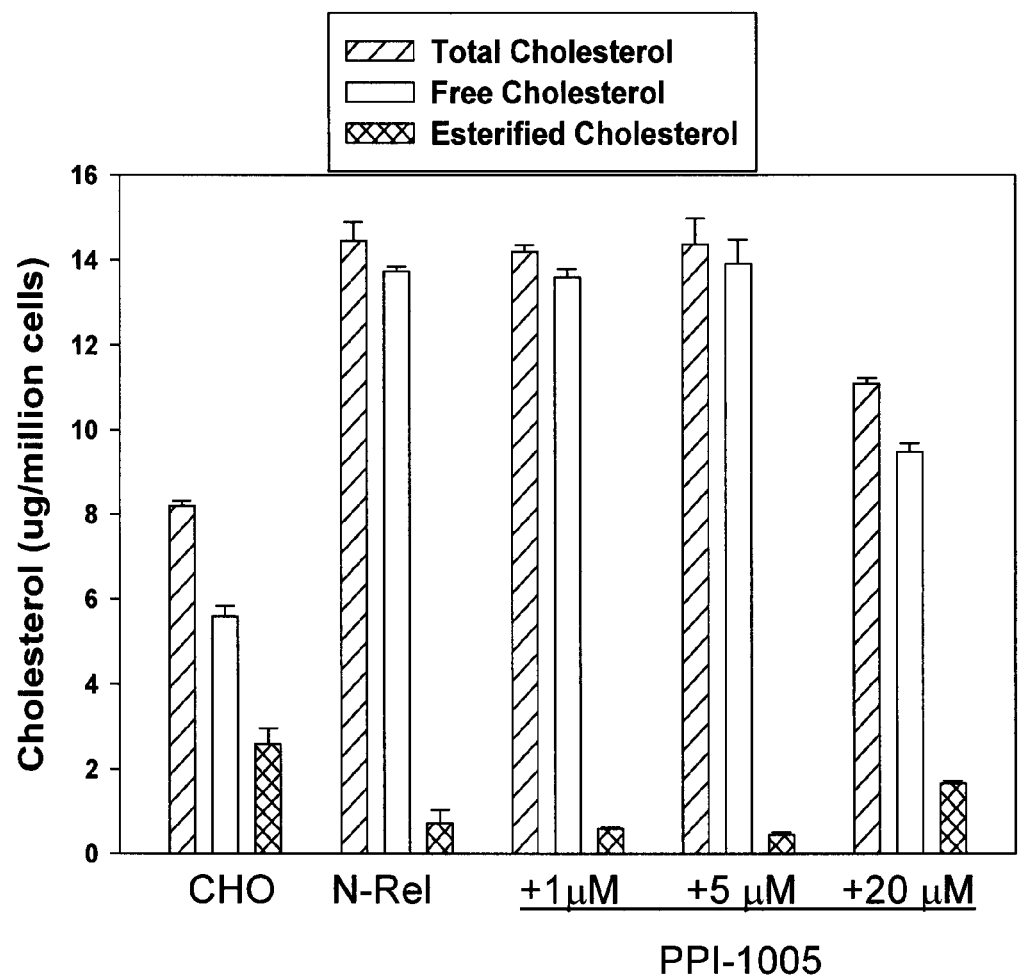
FIG. 5 shows the concentration response for the decrease in membrane cholesterol in N-Rel cells after a 48 hr incubation with 16:0(sn-1 alkyl)/DHA(sn-2 acyl) glycerol (PLM-05).

Biological systems with a pre-existing deficiency in plasmalogen synthesis and subsequent low plasmalogen levels (N-Rel vs. CHO) (FIG. 1) have elevated membrane cholesterol levels (FIG. 5). Elevation of DHA-PlsEtn to 80% of control values by PPI-1005 (FIG. 2) resulted in a significant reduction in membrane cholesterol (FIG. 5).

The cholesterol lowering effect of elevated PlsEtn levels was discovered to be dependent upon the sn-2 substituent (FIGS. 7 and 8). Only polyunsaturated fatty acids (DHA, 18:3) were observed to have cholesterol lowering activity in HEK293 cells whereas saturated, mono and diunsaturated fatty acids had no effect. Only the restoration of DHA-PlsEtn levels resulted in a robust attenuation of the elevated membrane cholesterol levels observed in N-Rel cells as a result of decreased plasmalogen levels (FIG. 7). These results indicate that poly-unsaturated fatty acid containing PlsEtn are selectively involved in membrane cholesterol homeostasis. PPI-1009 was also demonstrated to concentration-dependently decrease membrane cholesterol levels in NRel (FIG. 7) and HEK293 cells (FIG. 9). These results indicate that the membrane lowering effect of elevated PlsEtn levels requires the administration of plasmalogen precursor capable of selectively elevating PlsEtn levels with specific sn-2 substitutions.

The treatment of HEK293 cells with either PPI-1005 or PPI-1009 resulted in decreased levels of both AB-40 and AB-42 in both normal cells and cholesterol loaded cells (FIG. 10). These results further exemplify the functional utility of the plasmalogen precursors by their ability to positively modulate membrane protein function. In this regard, decreased membrane cholesterol levels are known to negatively modulate amyloid peptide production[15]. In addition to lowering membrane cholesterol in HEK293 cells, PPI-1005 and PPI-1009 were also observed to decrease the secretion of amyloid peptides (FIG. 10).

A structure-specific and concentration-dependent incorporation of PPI-1014 in N-Rel ethanolamine plasmalogens (PlsEtn) and phosphatidylethanolamines (PtdEtn) was also observed after 72 hours using 5, 10 and 20 μM concentrations of PPI-1014 (FIG. 17).

Example 3
Preparation of PPI-1011
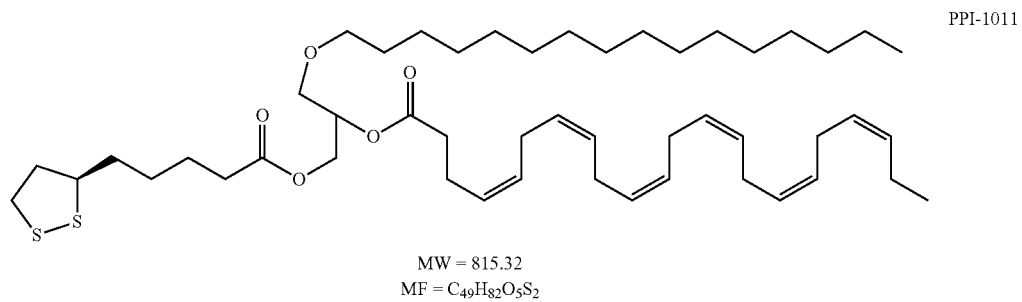 [SMILES: CC/C=C\C/C=C\C/C=C\C/C=C\C/C=C\C/C=C\CCC(=O)OC(COCCCCCCCCCCCCCCCC)COC(=O)CCCC[C@@H]1CCSS1]
MW = 815.32
MF = $C_{49}H_{82}O_5S_2$
Synthetic Scheme:
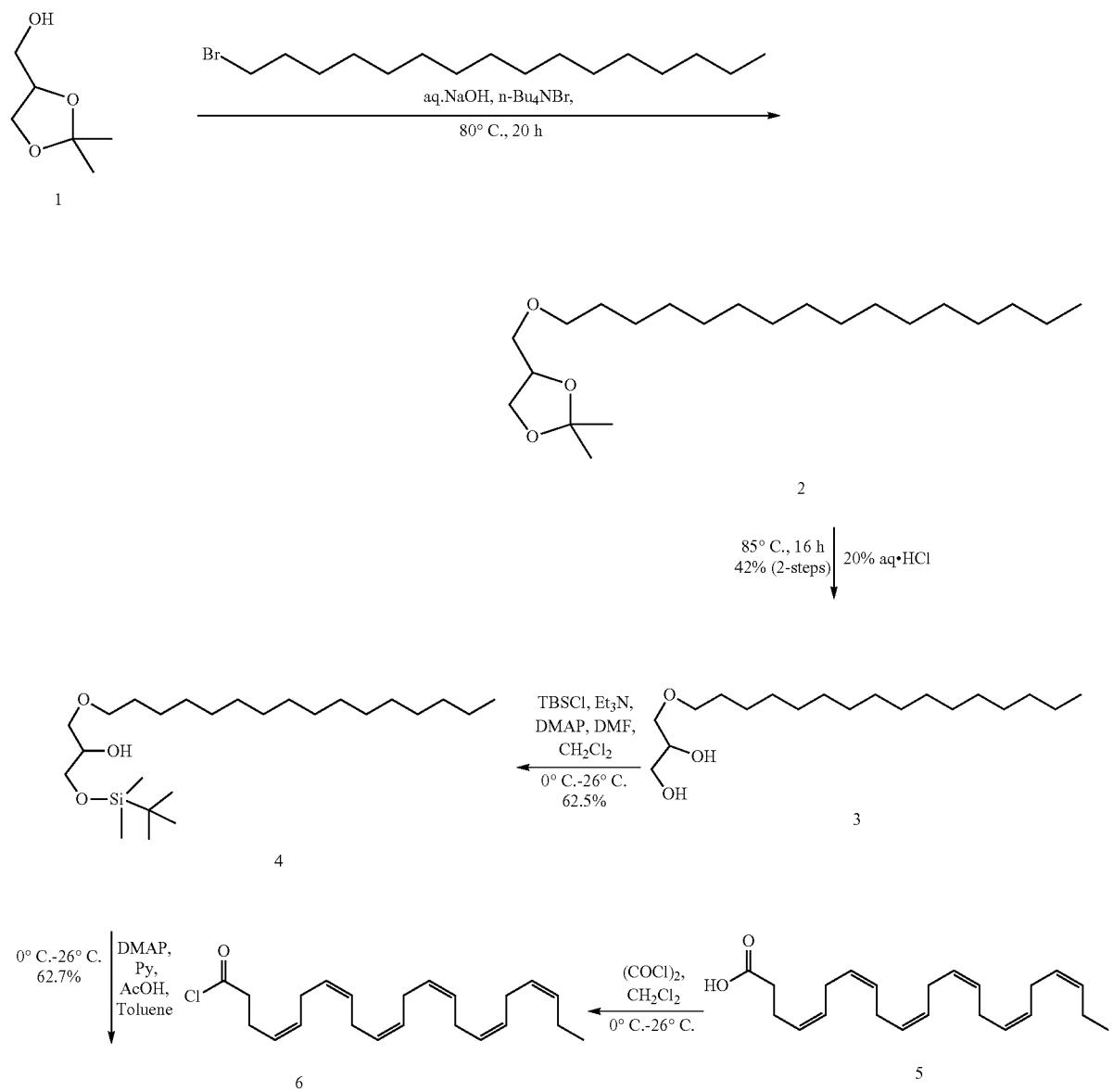

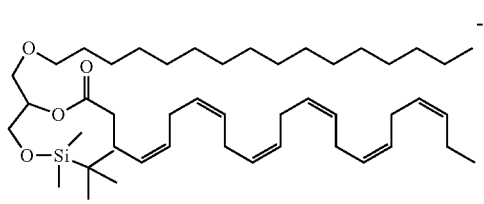
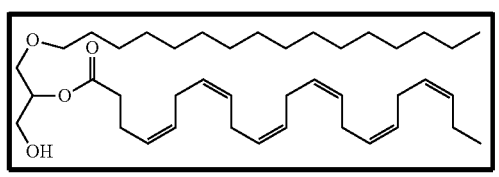
Synthetic Scheme for PPI-1011
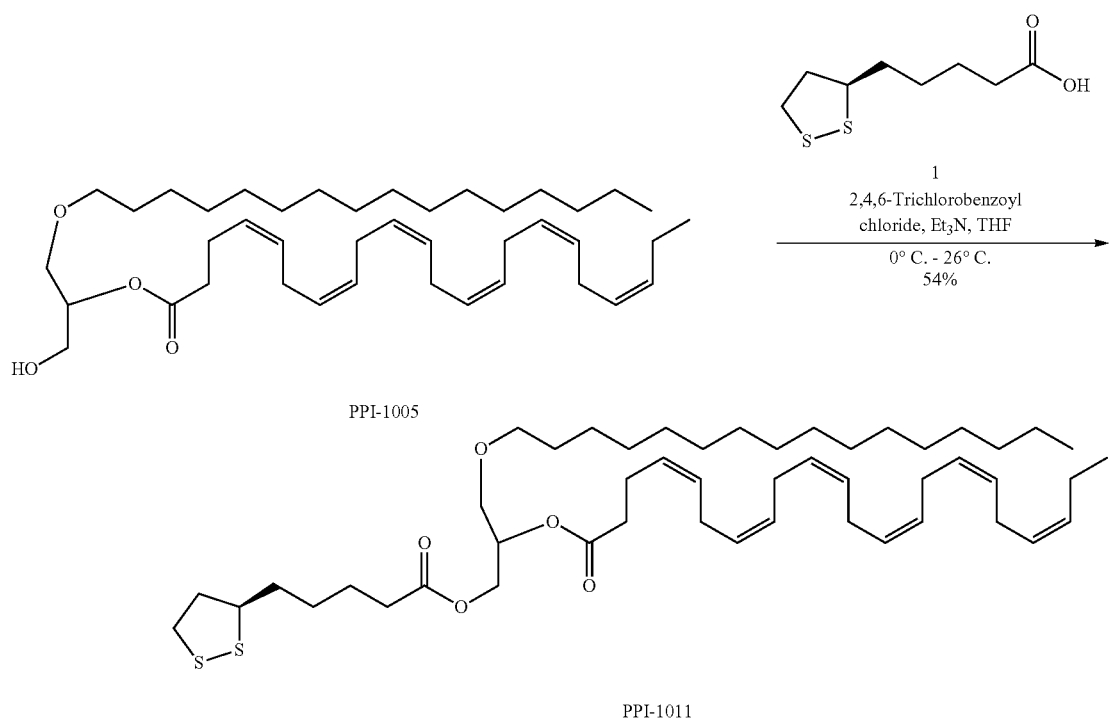
Reaction Step:
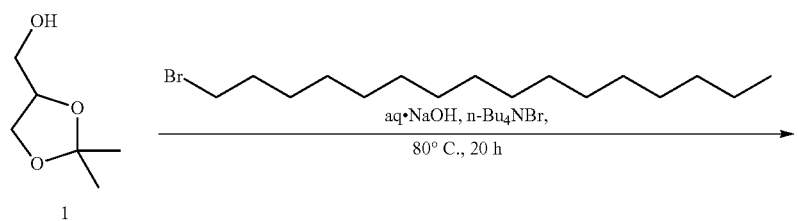
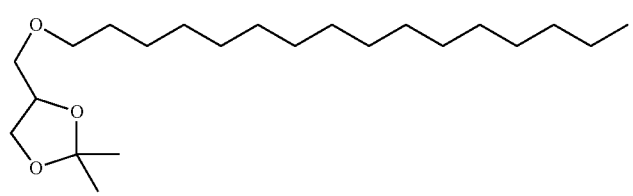

Brief procedure: A solution of compound 1 (2.0 Kg, 15.15 mol) in 10% NaOH solution (10.0 L) was stirred at 80° C. for 1 h, TBAB (992.0 g, 3.03 mol) added and stirred for 15 min. Cetyl bromide (5.5 kg, 18.18 mol) was added slowly and the reaction mixture was stirred at 80° C. for 20 h. (The reaction progress was monitored by diluting small aliquots with water, extracting with ethyl acetate and spotting over an analytical silica gel TLC plate (30% Ethyl acetate in pet-ether) and visualizing respective spots using Mo stain and $KMnO_4$ solution). The following are the Rfs of the components of the mixture: compound 1 (0.1), compound 2 (0.7).

Work up and purification: The reaction mixture was cooled to RT, extracted with $CH_2Cl_2$ (3×3.0 L). The combined $CH_2Cl_2$ layer was washed with $NaHCO_3$ solution (1.0 L), water (2×2.0 L), brine solution (1.0 L), dried over anhydrous $Na_2SO_4$ and concentrated to afford crude compound 2 (2.9 Kg, crude) as pale yellow liquid, which was used in next step.
Reaction Step:

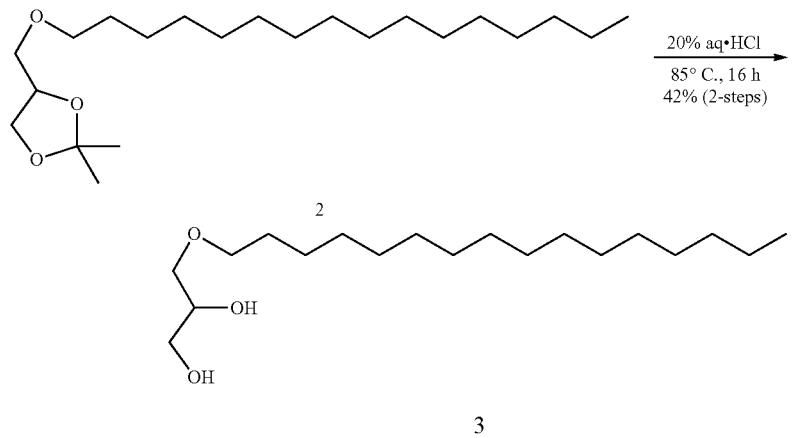

Brief procedure: A solution of compound 2 (2.9 Kg, 81.23 mol) in 20% aq HCl (14.5 L) was stirred at 85° C. for 16 h. (The reaction progress was monitored by diluting small aliquots with water, extracting with ethyl acetate and spotting over an analytical silica gel TLC plate (40% ethyl acetate in pet ether) and visualizing spots using Mo stain). The following are the Rfs of the components of the mixture: compound 2 (0.8), compound 3 (0.2).

Work up and purification: The reaction mixture was cooled to RT, extracted with $CH_2Cl_2$ (3×4.0 L). The combined organic layer was washed with $NaHCO_3$ solution (1.0 L), water (2×2.0 L), brine solution (1.0 L), dried over anhydrous $Na_2SO_4$ and concentrated to afford crude compound, which was triturated with 5% ethyl acetate in pet-ether (2×1.0 L) and dried to afford compound 3 (2.0 Kg, 42% from 2-steps) obtained as off white solid.
Reaction Step:

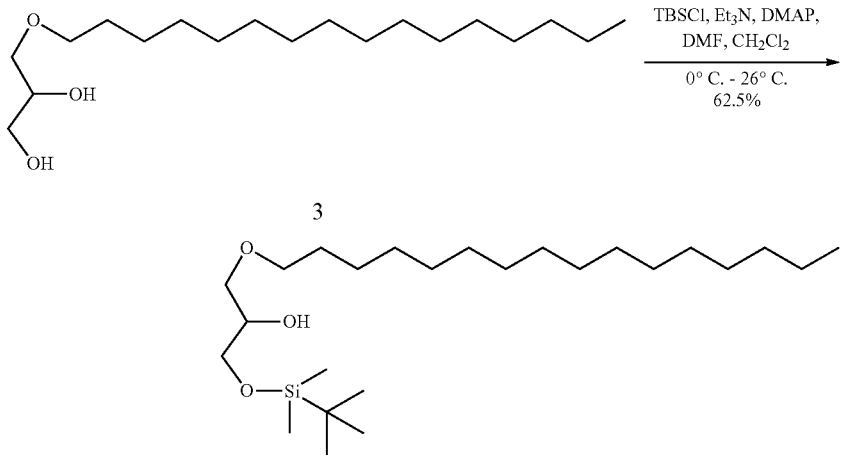

Brief procedure: To a cooled solution of compound 3 (1.0 Kg, 3.16 mol) in DMF (640.0 mL) and $CH_2Cl_2$ (400.0 mL) at 0° C., added DMAP (38.6 g, 0.32 mol) followed by triethylamine (735.0 g, 7.27 mol). After addition the reaction mixture was stirred at 0° C. for 30 min and added TBSCl (572.0 g, 3.79 mol) in equal portions (3 portions) for 1 h and the reaction mixture was stirred for 20 h at RT. (The reaction progress was monitored by quenching small aliquots with water, extracting with $CH_2Cl_2$ and spotting over an analytical silica gel TLC plate (20% Ethyl acetate in pet ether) and visualizing spots using Mo stain and $KMnO_4$). The following are the Rts of the components of the mixture: compound 3 (0.15), compound 4(0.7).

Work up and purification: The reaction mixture was diluted with $CH_2Cl_2$ (2.0 L), washed with water (3×3.0 L), brine solution (1.0 L), dried over anhydrous $Na_2SO_4$ and concentrated. The obtained crude compound was purified by column chromatography (silica gel 100-200 mesh) using 5% ethyl acetate in pet ether as eluent to afford compound 4 (850 g, 90%) obtained as pale yellow oil.

Reaction Step:

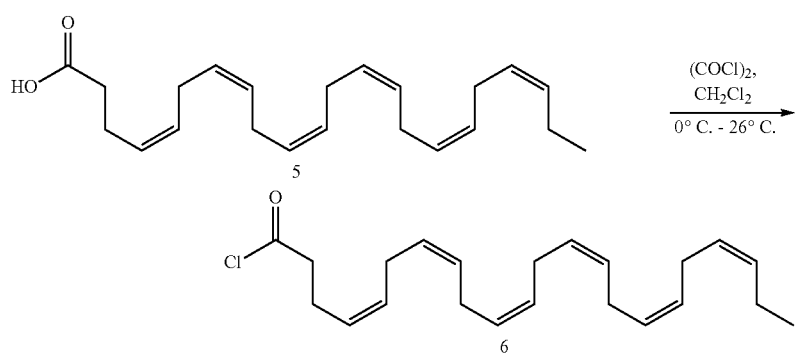

Brief procedure: To a cooled solution of compound 5 (160.0 g, 0.487 mol), DMF (1.0 mL) in $CH_2Cl_2$ (500.0 mL) at 0° C., Oxalyl chloride (105.0 g, 0.828 mol) was added slowly for 30 min. After addition the reaction mixture was stirred at 26° C. for 4 h. (The reaction progress was monitored by quenching small aliquots with MeOH and spotting over an analytical silica gel TLC plate (10% Ethyl acetate in pet ether) and visualizing spots using $KMnO_4$ solution). The following are the Rfs of the components of the mixture: compound 5 (0.3), compound 6 (0.8).

Work up and purification: The reaction mixture was concentrated under $N_2$ atmosphere to afford crude compound 6 (175 g, crude).

Reaction Step:

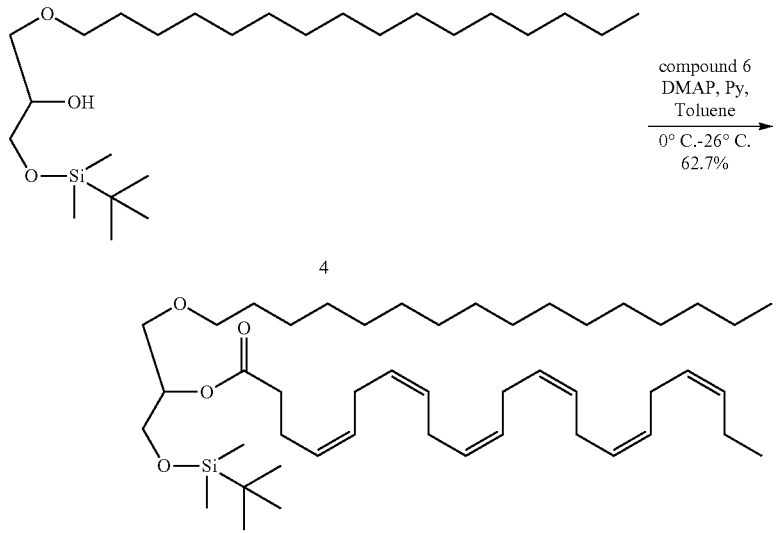

Brief procedure: To a cooled solution of compound 4 (150.0 g, 0.348 mol) in Toluene (1.25 L) at 0° C., pyridine (110.0 g, 1.39 mol) was added followed by DMAP (122.2 g, 0.348 mol) and stirred for 10 min. Added a solution of crude compound 6 (175.0 g, 0.504 mol) in Toluene (250.0 mL) for 15 min. After addition the reaction mixture was stirred at RT for 20 h. (The reaction progress was monitored by quenching small aliquots with water, extracting with EtOAc and spotting over an analytical silica gel TLC plate (5% Ethyl acetate in pet ether) and visualizing spots using KMnO₄ solution). The following are the Rts of the components of the mixture: compound 4 (0.2), compound 7 (0.5).

Work up and purification: The reaction mixture was diluted with ethyl acetate (3.0 L), washed with water (1.0 L), 0.05 N HCl (500.0 mL), water (2×1.0 L), brine solution (500.0 mL) dried over anhydrous Na₂SO₄ and concentrated to afford crude compound 7, which was purified by column chromatography (silica gel 100-200 mesh) using 2% ethyl acetate in pet ether as eluent to afford compound 7 (162 g, 62.7%) obtained as pale yellow oil.

Reaction Step:

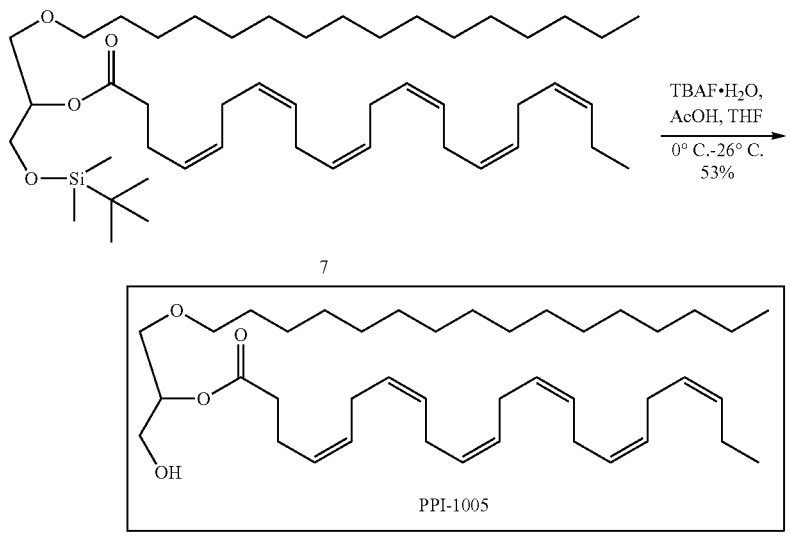

Brief procedure: To a cooled solution of compound 7 (160.0 g, 216.21 mmol) in THF (10.0 mL) and acetic acid (52.0 g) at 0° C., TBAF (226.0 g, 864.86 mmol) was added in equal portions for 30 min. After addition the reaction mixture was stirred at RT for 6 h. (The reaction progress was monitored by spotting over an analytical silica gel TLC plate (20% Ethyl acetate in pet ether) and visualizing spots using Mo stain and KMnO₄ solution). The following are the Rfs of the components of the mixture: compound 7 (0.9), compound PPI-1005 (0.4).

Work up and purification: The reaction mixture was diluted with ethyl acetate (3.0 L), washed with water (2×2.0 L), brine (500.0 mL), dried over anhydrous Na₂SO₄ and concentrated to afford crude compound, which was purified by column chromatography (silica gel 100-200 mesh) using 7% ethyl acetate in pet ether as eluent to afford compound PPI-1005 (72 g, 53%) obtained as pale yellow oil.

Reaction Step:

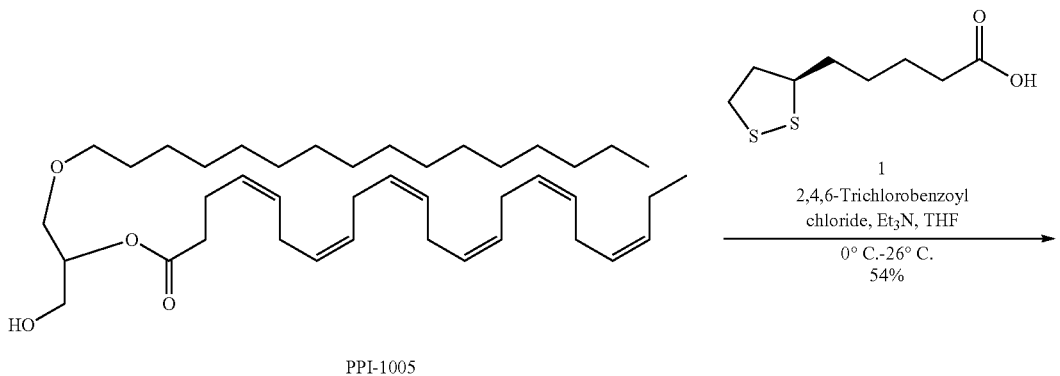

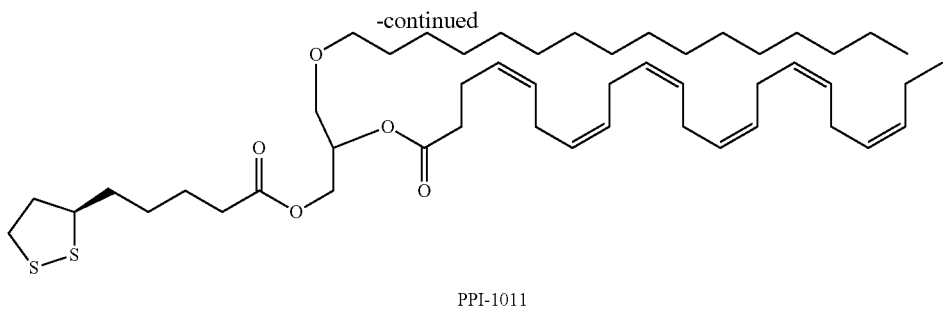

PPI-1011

Brief procedure: To a cooled solution of α-Lipoic acid 1 (12.0 g, 58.25 mmol) in THF (500.0 mL) at 0° C., triethylamine (8.1 mL, 58.25 mmol) was added slowly for 10 min, followed by 2,4,6-Trichlorobenzoyl chloride (14.2 g, 58.25 mmol). After addition the reaction mixture was allowed to RT and stirred for 18 h. (The reaction progress was monitored by spotting on an analytical silica gel TLC plate (20% EtOAc in pet-ether), and visualizing spots using 254 nm UV light and Hanessian's stain). The following are the Rfs of the components of the mixture: compound 1 (0.2), intermediate (0.6).

The reaction mixture was filtered off, the solid was washed with THF (25.0 mL), the combined filtrate was concentrated using reduced pressure under $N_2$ atmosphere to obtain the crude anhydride, which was dissolved in benzene (500.0 mL, cooled to 0° C. and added DMAP (7.1 g, 58.25 mmol), stirred for 10 min. To the reaction mixture added a solution of PPI-1005 (40.1 g, 64.07 mmol) in benzene (100.0 mL) slowly at 0° C. After addition the reaction mixture was allowed to RT and stirred for 24 h. (The reaction progress was monitored by quenching small aliquots with $H_2O$, extracting with ethyl acetate and spotting on an analytical silica gel TLC plate (15% THF in pet-ether), and visualizing spots using 254 nm UV light and Hanessian's stain). The following are the Rfs of the components of the mixture: PPI-1005 (0.3), PPI-1011 (0.5).

Work up and purification: The reaction mixture was diluted with ethyl acetate (2000 mL), washed with saturated NaHCO3 solution (1×400 mL), 0.05N HCl (1×400 mL), water (1×400 mL), brine (1×400 mL) and dried over anhydrous $Na_2SO_4$ and concentrated to obtain the crude compound, which was purified by column chromatography (neutral silica gel 100-200 mesh) using 2.5 to 5% THF in pet ether as eluent.

The title compound PPI-1011(28.0 g, 54%) was obtained as pale brown oil.

Example 4

Alternate Method for Preparation of PPI-1009

PPI-1009

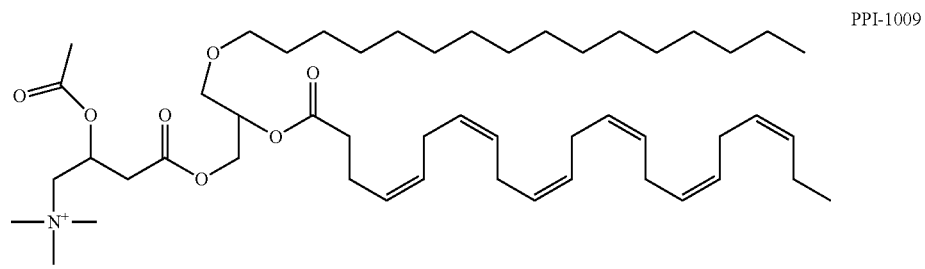

MW = 813.25
MF = $C_{50}H_{86}NO_7$

Synthetic Scheme:

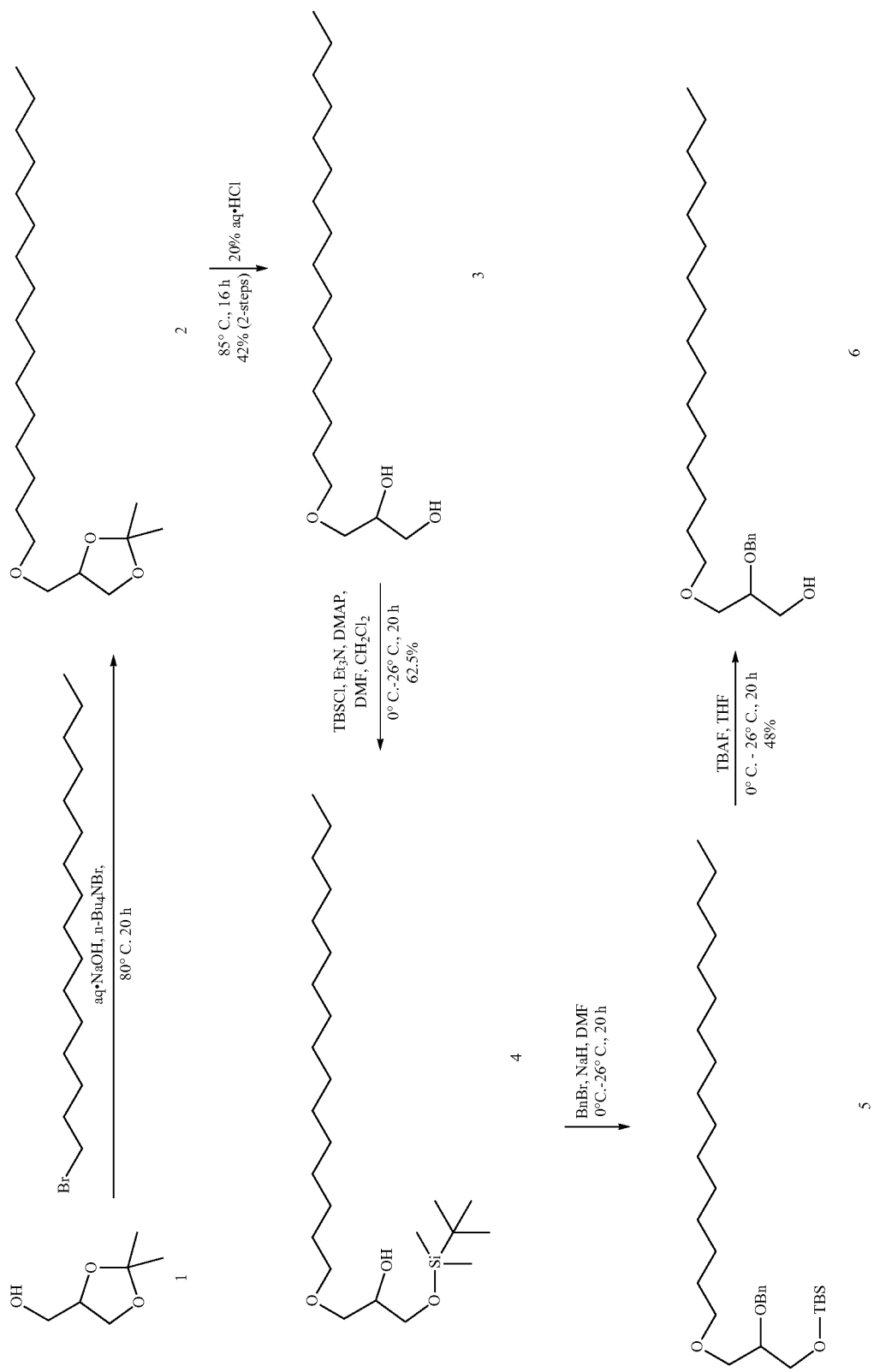

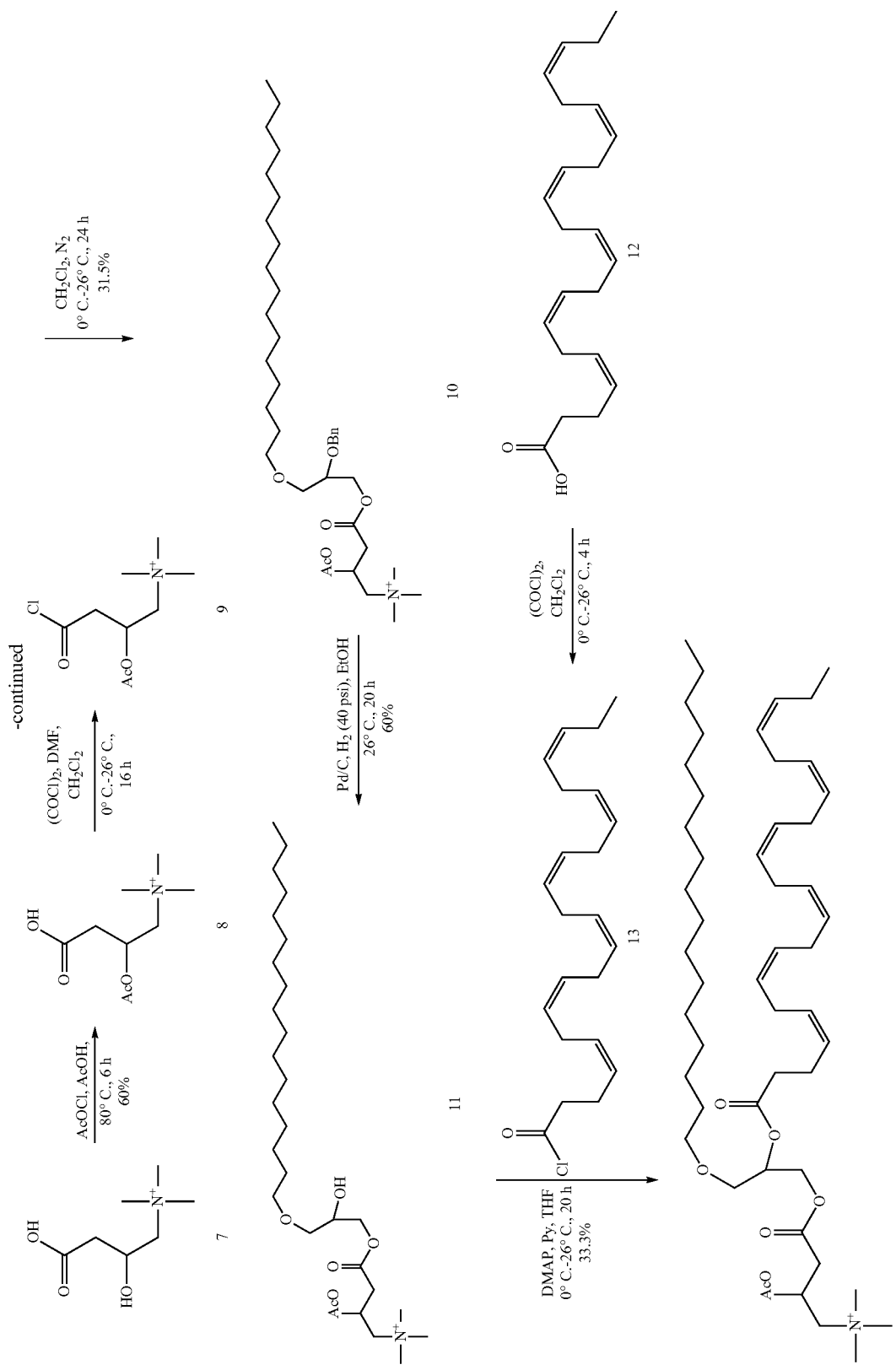

Reaction Step:

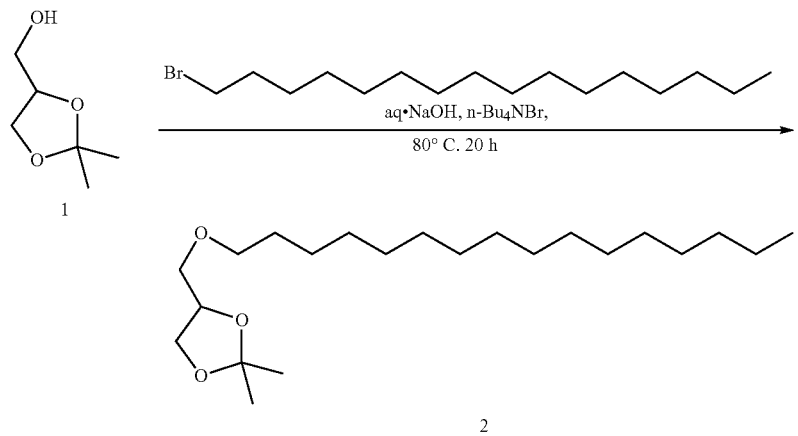

Procedure: A solution of compound 1 (2.0 Kg, 15.15 mol, Alfa Aesar) in 10% NaOH solution (10.0 L) was stirred at 80° C. for 1 h, added TBAB (992.0 g, 3.03 mol, Rajdhani scientific) and stirred for 15 min. Added cetyl bromide (5.5 kg, 18.18 mol, Alfa Aesar) slowly and the reaction mixture was stirred at 80° C. for 20 h. (The reaction progress was monitored by diluting small aliquots with water, extracting with ethyl acetate and spotting over an analytical silica gel TLC plate (30% Ethyl acetate in pet-ether) and visualizing respective spots using Mo stain and $KMnO_4$ solution). The following are the Rfs of the components of the mixture: compound 1 (0.1), compound 2 (0.7). The reaction mixture was cooled to RT, extracted with $CH_2Cl_2$ (3×3.0 L). The combined $CH_2Cl_2$ layer was washed with $NaHCO_3$ solution (1.0 L), water (2×2.0 L), brine solution (1.0 L), dried over anhydrous $Na_2SO_4$ and concentrated to afford crude compound 2 (2.9 Kg, crude) as pale yellow liquid, which was used in next step.

Reaction Step:

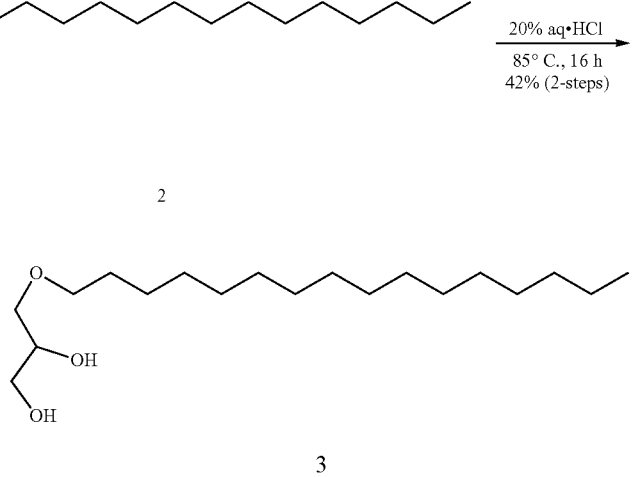

Procedure: A solution of compound 2 (2.9 Kg, 81.23 mol) in 20% aq HCl (14.5 L) was stirred at 85° C. for 16 h. (The reaction progress was monitored by diluting small aliquots with water, extracting with ethyl acetate and spotting over an analytical silica gel TLC plate (40% ethyl acetate in pet ether) and visualizing spots using Mo stain). The following are the Rfs of the components of the mixture: compound 2 (0.8), compound 3 (0.2). The reaction mixture was cooled to RT, extracted with $CH_2Cl_2$ (3×4.0 L). The combined organic layer was washed with $NaHCO_3$ solution (1.0 L), water (2×2.0 L), brine solution (1.0 L), dried over anhydrous $Na_2SO_4$ and concentrated to afford crude compound, which was triturated with 5% ethyl acetate in pet-ether (2×1.0 L) and dried to afford compound 3 (2.0 Kg, 42% from 2-steps) obtained as off white solid.

Reaction Step:

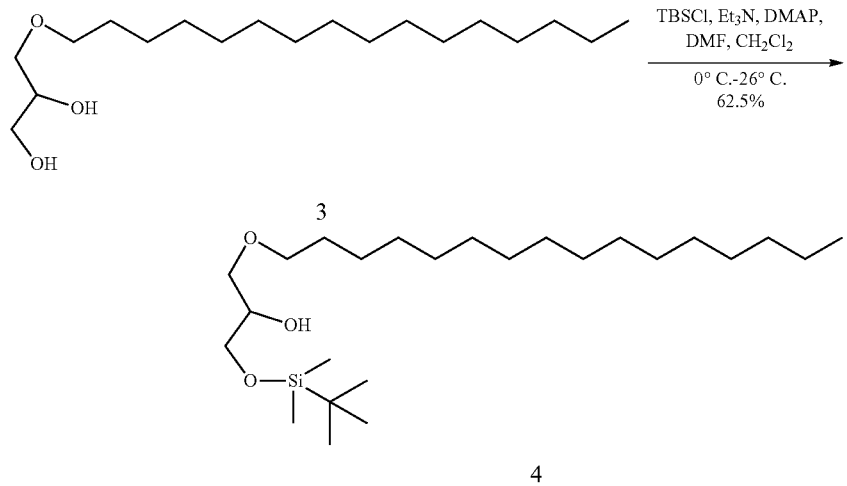

Procedure: To a cooled solution of compound 3 (1.0 Kg, 3.16 mol) in DMF (640.0 mL) and CH$_2$Cl$_2$ (400.0 mL) at 0° C., added DMAP (38.6 g, 0.32 mol) followed by triethylamine (735.0 g, 7.27 mol, Rankem). After addition the reaction mixture was stirred at 0° C. for 30 min and added TBSCl (572.0 g, 3.79 mol, Fluoro chem 3.0 kg) in equal portions (3 portions) for 1 h and the reaction mixture was stirred for 20 h at RT. (The reaction progress was monitored by quenching small aliquots with water, extracting with CH$_2$Cl$_2$ and spotting over an analytical silica gel TLC plate (20% Ethyl acetate in pet ether) and visualizing spots using Mo stain and KMnO$_4$). The following are the Rfs of the components of the mixture: compound 3 (0.15), compound 4(0.7). The reaction mixture was diluted with CH$_2$Cl$_2$ (2.0 L), washed with water (3×3.0 L), brine solution (1.0 L), dried over anhydrous Na$_2$SO$_4$ and concentrated. The obtained crude compound was purified by column chromatography (silica gel 100-200 mesh) using 5% ethyl acetate in pet ether as eluent to afford compound 4 (850 g, 90%) obtained as pale yellow oil.

Procedure: To a cooled solution of compound 4 (734 g, 1.706 mol) in DMF (2.5 L) at 0° C., added 60% NaH (204.0 g, 5.12 mol) in portions for 30 min. After addition the reaction mixture was stirred at 0° C. for further 30 min and added benzyl bromide (438.0 g, 2.56 mol, S.D fine chemicals) drop wise for 1 h. The reaction mixture allowed to RT was stirred for 20 h. (The reaction progress was monitored by quenching small aliquots with water, extracting with EtOAc and spotting over an analytical silica gel TLC plate (5% Ethyl acetate in pet ether) and visualizing spots using Mo stain and KMnO$_4$). The following are the Rfs of the components of the mixture: compound 4 (0.2), compound 5(0.5). The reaction mixture was quenched with methanol (250 mL), cold water (1500 mL) and extracted using ethyl acetate (2×2.0 L). The combined ethyl acetate layer was washed with water (3×1.0 L), brine solution (1.0 L), dried over anhydrous Na$_2$SO$_4$ and concentrated. The obtained crude compound 5 (887 g) was used in the next step without further purification.

Reaction Step:

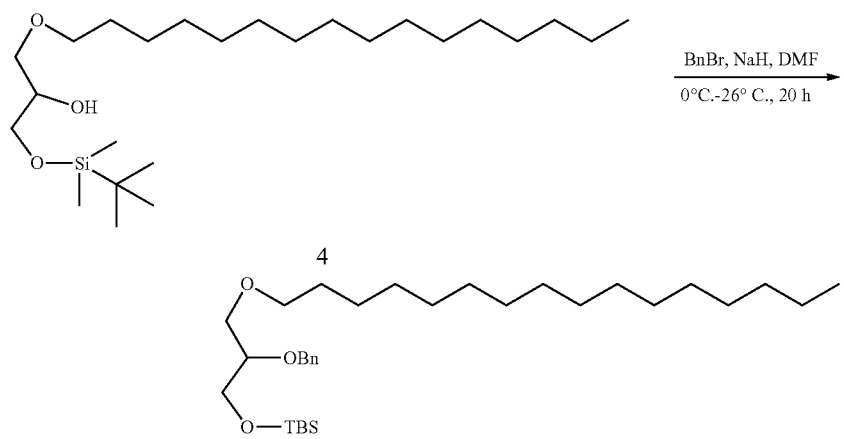

Reaction Step:

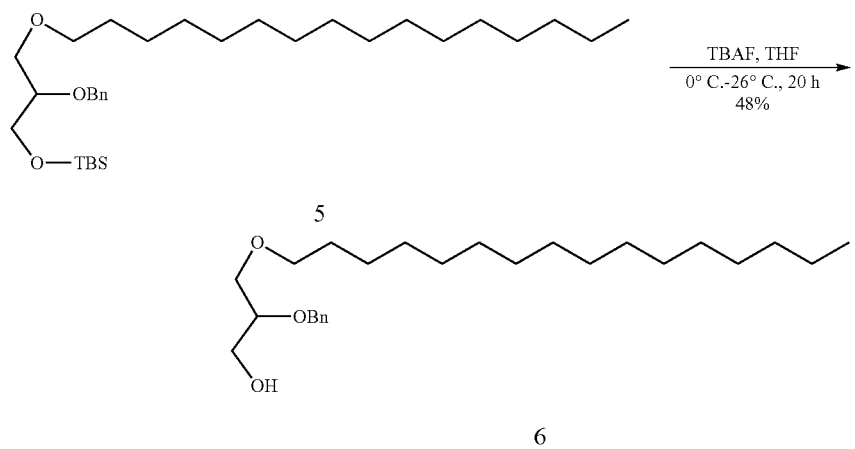

Procedure: To a cold solution of crude compound 5 (887.0 g, 1.702 mol) in THF (2.0 L) at 0° C., a solution of TBAF (1.3 Kg, 5.107 mol, Chemrich fine chemicals) in THF (1.0 L) was added slowly for 1 h. After addition the reaction mixture was stirred at RT for 16 h. (The reaction progress was monitored by quenching small aliquots with water, extracting with EtOAc spotting over an analytical silica gel TLC plate (30% Ethyl acetate in pet ether) and visualizing spots using Mo stain and $KMnO_4$ solution). The following are the Rfs of the components of the mixture: compound 5 (0.9), compound 6 (0.3). The reaction mixture was diluted with ethyl acetate (2.5 L), washed with water (2×1.0 L), brine (1.0 L), dried over anhydrous $Na_2SO_4$ and concentrated to afford crude compound, which was purified by column chromatography (silica gel 100-200 mesh) using 7% ethyl acetate in pet ether as eluent to afford compound 6 (330 g, 48% from 2 steps) obtained as pale yellow oil.

Reaction Step:

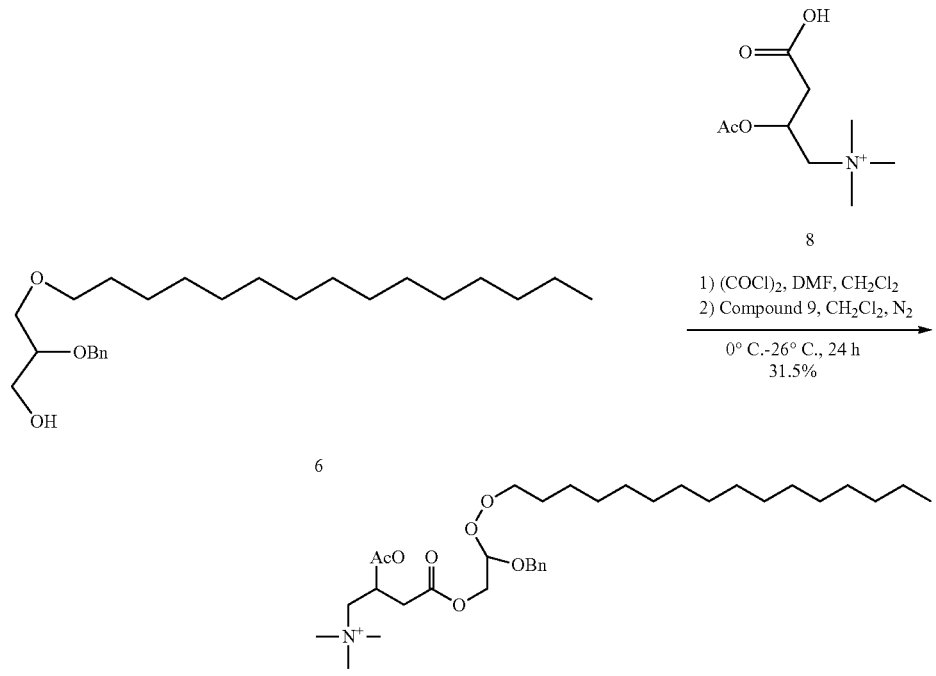

Procedure: To a cold solution of N-Acetyl carnitene 8 (239.0 g, 1.177 mol, Molecula life Sciences) in $CH_2Cl_2$ (500.0 mL) and DMF (5.0 mL) at 0° C., added oxalyl chloride (179.4 g, 1.412 mol) slowly for 30 min and stirred at RT for 4 h. The solvent from the reaction mixture was removed by distillation under reduced pressure and traces of oxalyl chloride by co-distilling with $CH_2Cl_2$. The obtained crude compound 9 (250 g) was dissolved in $CH_2Cl_2$ (500.0 mL) and added slowly to a cold solution of compound 6 (334.0 g, 0.823 mol) in CH$_2$Cl$_2$ (500.0 mL) at 0° C. with bubbling N$_2$ gas. After addition the reaction mixture was stirred for 20 h with continuous bubbling of N$_2$ at RT. (The reaction progress was monitored by quenching small aliquots with water, extracting with CH$_2$Cl$_2$ and spotting over an analytical silica gel TLC plate (25% MeOH in chloroform) and visualizing spots using Mo stain and KMnO$_4$). The following are the Rfs of the components of the mixture: compound 6 (0.8) and compound 10 (0.3). The reaction mixture was diluted with CH$_2$Cl$_2$ (2.0 L), washed with brine solution (250 mL), dried over anhydrous Na$_2$SO$_4$ and concentrated to obtain crude compound which was purified by column chromatography (silica gel 100-200 mesh) using 5% MeOH in chloroform as eluent to afford compound 10 (153.0 g, 31.5%) obtained as pale yellow oil.

Reaction Step:

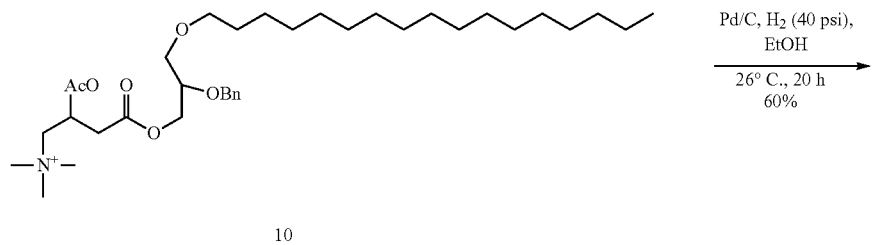

10

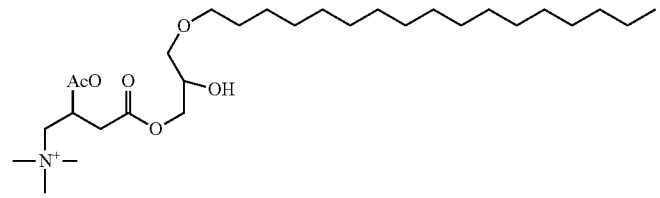

11

Brief procedure: To a suspension of 10% Pd/C (40.0 g, 25% w/w, AlfaAesar) in ethanol (1.2 L), compound 10 (150 g, 0.298 mol) was added and hydrogenated (H$_2$, 40 psi pressure) at RT for 20 h. (The reaction progress was monitored by spotting over an analytical silica gel TLC plate (25% MeOH in chloroform) and visualizing spots using Mo stain and Ninhydrin solution). The following are the Rfs of the components of the mixture: compound 10 (0.4), compound 11(0.2). The reaction mixture was filtered off through celite bed, washed the cake with ethanol (2×200 mL), the combined filtrate was concentrated to obtain crude compound, was purified by column chromatography (silica gel 100-200 mesh) using 10% Methanol in chloroform as eluent to afford compound 11 (75 g, 60%) obtained as pale yellow oil.

Reaction Step:

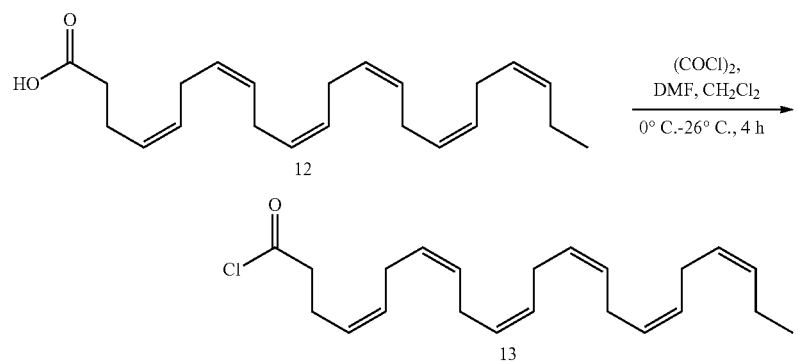

Brief procedure: To a cooled solution of compound 5 (48.0 g, 0.146 mol, Nu-Chek-Prep Inc), DMF (1.0 mL) in CH$_2$Cl$_2$ (300.0 mL) at 0° C., Oxalyl chloride (22.3 g, 0.175 mol, Molecula Lifesciences) was added slowly for 30 min. After addition the reaction mixture was stirred at 26° C. for 4 h. (The reaction progress was monitored by quenching small aliquots with MeOH and spotting over an analytical silica gel TLC plate (10% Ethyl acetate in pet ether) and visualizing spots using KMnO$_4$ solution). The following are the Rfs of the components of the mixture: compound 12 (0.3), compound 13 (0.8). The reaction mixture was concentrated under N$_2$ atmosphere to afford crude compound 6 (57 g, crude).

Reaction Step:

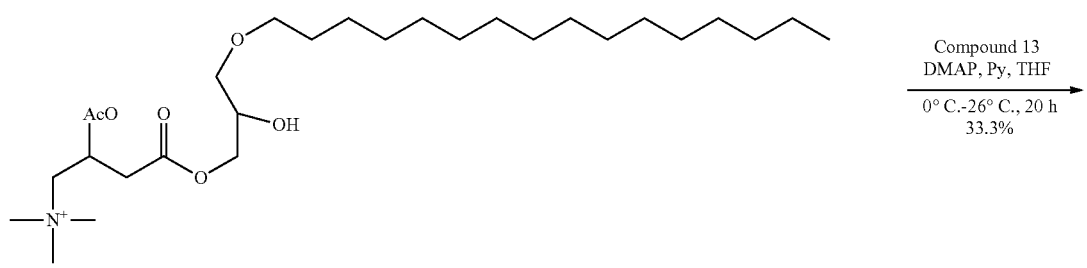

11

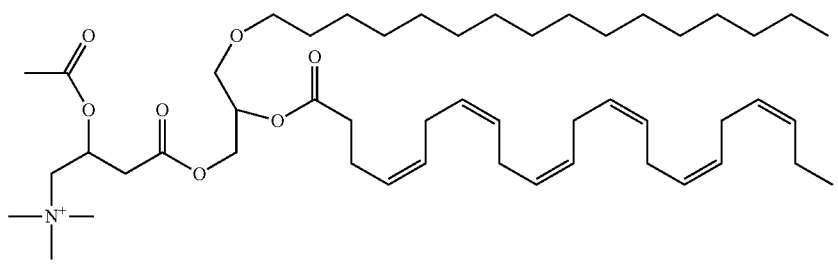

PPI-1009

Brief procedure: To a cooled solution of compound 11 (50.0 g, 0.102 mol) in THF (1.0 L) at 0° C., pyridine (32.3 g, 0.409 mol) was added followed by DMAP (12.5 g, 0.102 mol) and stirred for 10 min. Added a solution of crude compound 13 (57.0 g, 0.163 mol) in Toluene (1.0 mL) for 15 min. After addition the reaction mixture was stirred at RT for 20 h. (The reaction progress was monitored by quenching small aliquots with water, extracting with EtOAc and spotting over an analytical silica gel TLC plate (20% Methanol in chloroform) and visualizing spots using Mo stain and Ninhydrin solution). The following are the Rfs of the components of the mixture: compound 11 (0.2) and PPI-1009 (0.5). The reaction mixture was diluted with ethyl acetate (2.0 L), washed with 0.5N HCl (250 mL), brine solution (250.0 mL) dried over anhydrous Na$_2$SO$_4$ and concentrated to afford crude compound, which was purified by column chromatography (silica gel 100-200 mesh) using 20% Methanol in chloroform as eluent to afford compound PPI-1009 (27 g, 33.3%) obtained as pale yellow oil.

Example 5
Preparation of PPI-1014
Target Molecule
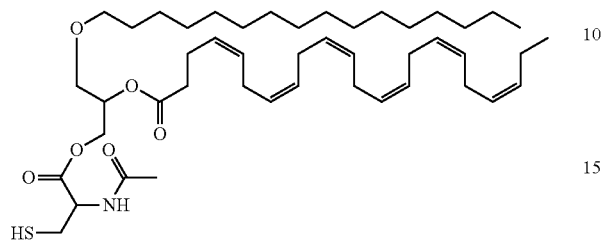
MW = 772.19
MF = $C_{46}H_{77}NO_6S$
Synthetic Scheme:
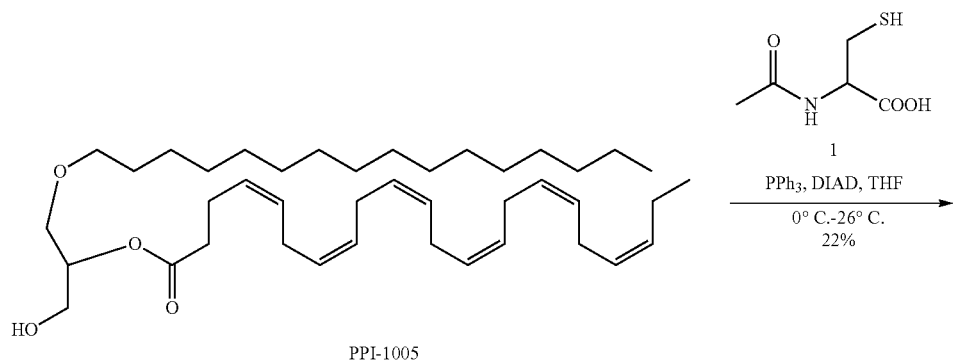
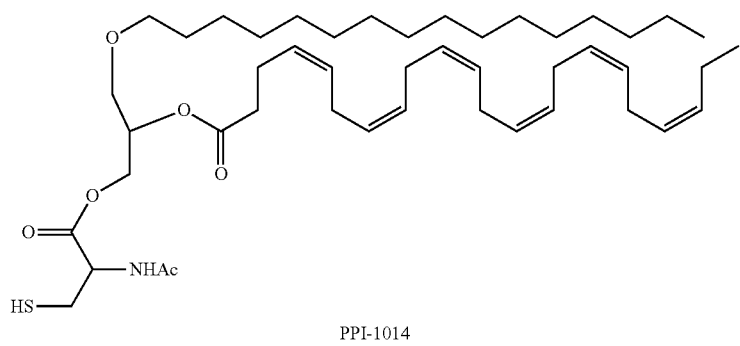

Reaction Step:

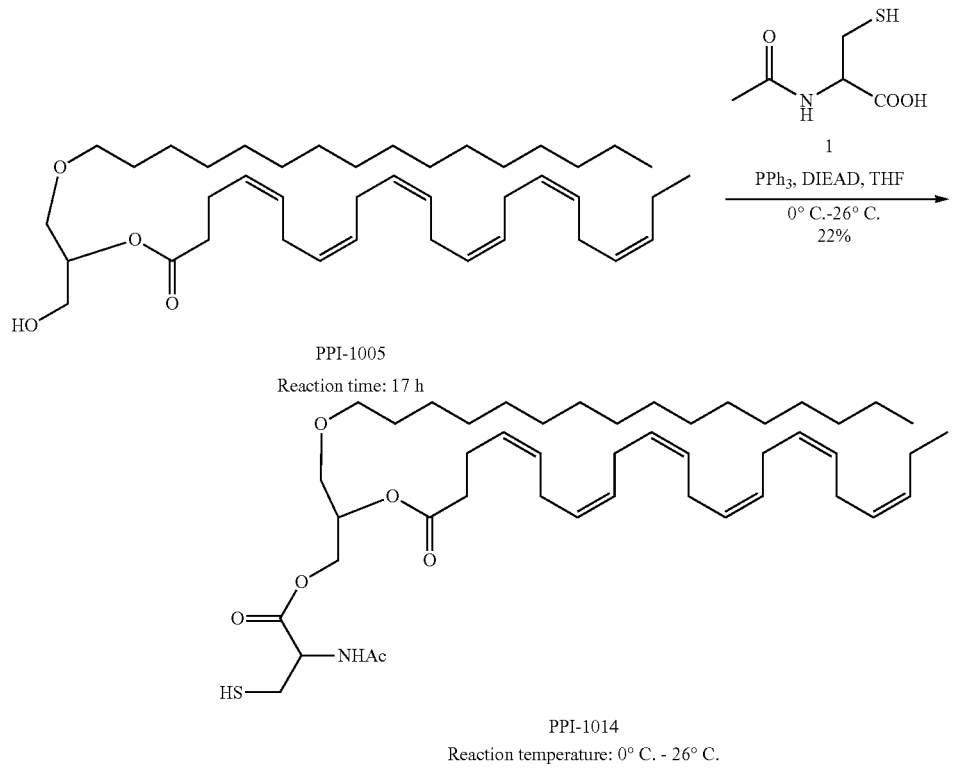

PPI-1005
Reaction time: 17 h

PPI-1014
Reaction temperature: 0° C. - 26° C.

Brief procedure: To a cooled solution of PPI-1005 (12.0 g, 19.16 mmol) in THF (600 mL), added Triphenyl phosphene (7.5 g, 28.75 mmol) and stirred at 0° C. for 10 min, followed by slow addition of DIEAD (5.8 g, 28.75 mmol). After stirring at 0° C. for 30 min the reaction mixture was added N-Acetyl cystine (4.6 g, 28.75 mmol) and allowed to stir at RT for 16 h. (The reaction progress was monitored by extracting with ethyl acetate and spotting on an analytical silica gel TLC plate (30% Ethyl acetate in pet-ether), and visualizing spots using Mo stain). The following are the Rfs of the components of the mixture: PPI-1005 (0.8), PPI-1014 (0.4).

Work up and purification: The reaction mixture was diluted with water (75 mL) and extracted using ethyl acetate (3×200 mL). The combined ethyl acetate layer was washed with brine (50 mL), dried over anhydrous $Na_2SO_4$ and concentrated to afford the crude compound, which was purified by column chromatography (100-200 mesh silica gel) using 0 to 13% ethyl acetate in pet ether as eluent.

The title compound PPI-1014 (3.2 g, 22%) was obtained as pale yellow oil exhibited the following properties. $^1$H NMR (300 MHz, $CDCl_3$): δ 6.35 (bs, 1H), 5.39-5.22 (m, 13H), 4.92-4.88 (m, 1H), 4.55-4.22 (m, 3H), 3.55-3.41 (m, 5H), 3.02-2.97 (m, 2H), 2.85-2.77 (m, 10H), 2.40 (s, 5H), 2.11-2.04 (m, 5H), 1.57-1.52 (m, 2H), 1.36-1.25 (m, 30H), 0.97 (t, J=7.66 Hz; 3H), 0.88 (t, J=6.63 Hz; 3H). Mass (M+H): 772.3, HPLC purity-93.68%.

Example 6

Animal Studies

Male New Zealand rabbits (1.8-2.5 kg) were orally dosed with PPI-1011, neat in hard gelatin capsules (size 3). For time course studies, rabbits were dosed with 200 mg/kg of PPI-1011 and animals sacrificed via euthenol overdose at 1, 3, 6, 12, 18, 24 and 48 hr. Blood was collected by cardiac puncture and plasma frozen at −70° C. for later analysis. Kidney and liver also were harvested and stored at −70° C. for later analysis. These studies were conducted as 2 experiments with overlapping groups at 12 hrs (Exp. 1: 1, 3, 6, and 12 hrs; Exp. 2: 12, 18, 24 and 48 hrs). Controls were harvested at each timepoint. Plasmalogens and lipids were extracted and analyzed by LC-MS/MS as previously reported (Goodenowe et al., 2007).

As seen in FIG. 11, using an oral dose of 200 mg/kg the plasmalogen precursor PPI-1011 was incorporated into circulating plasmalogens. Deacylation at sn-2, releasing docosahexaenoic acid (DHA), also was observed. The greatest incorporation was into the 16:0/22:6, 18:0/22:6 and 18:1/22:6 ethanolamine plasmalogens and phosphatidylethanolamines. No change in the reference phosphatidylethanolamine 16:0/18:0 was observed.

Further examination of the timecourse (FIG. 12) of incorporation in plasma revealed that maximum incorporation was at 12 hours and that this level of incorporation was maintained over the remaining observation period (48 hr). This was the case for both the phosphatidylethanolamines and the ethanolamine plasmalogens. In contrast, circulating DHA levels peaked at 6 hours and fell to a lesser steady-state by 18 hours.

Studies of dose-dependent incorporation (FIG. 13) of PPI-1011 into plasma plasmalogens and phosphatidylethanolamines demonstrated that a new steady-state level in these circulating phospholipids was attained in a dose-dependent manner from 10 to 200 mg/kg. However, further increases in dose did not increase the steady-state levels of plasmalogens and phosphatidylethanolamines above that obtained with 200 mg/kg. In contrast, the highest steady-state levels of circulating DHA were obtained at 500 mg/kg and did not further increase at a dose of 1000 mg/kg.

Augmentation of tissue plasmalogens and DHA was also observed in kidney (FIGS. 4 and 5) and liver (FIG. 6) tissues.

These results indicate that PPI-1011 is orally bioavailable in the rabbit and is converted to DHA-containing ethanolamine plasmalogens and phosphatidylethanolamines via deacylation/re-acylation reactions. In addition, the results suggest that endogenous metabolic systems may limit the maximal increase that that can be pharmacologically augmented.

Example 7

Modulating Membrane Protein Abundance in Vitro with Plasmalogen Precursors

The following studies demonstrate the effectiveness of a plasmalogen precursor (1-alkyl-2 acyl glycerol) in altering the abundance of membrane-resident proteins. The cellular effects of the compound are demonstrated in wild-type cells, as well as in conditions of artificially elevated membrane cholesterol.

In wild-type cells, an elevation of amyloid precursor protein (APP) modulating enzyme ADAM10 and cholesterol esterification protein SOAT1 was observed with an increase in plasmalogen precursor concentration. Similar effects were observed in a cholesterol-loaded model. Additionally, a different APP processing enzyme, BACE1, showed a decrease in abundance only in cholesterol loaded cells. Without wishing to be bound by theory, this evidence supports a method of reducing the amyloid load in the context of Alzheimer's disease and simultaneously re-equilibrating the membrane cholesterol content of the system, thereby offering potential benefits in the treatment of diseases like atherosclerosis and hypercholesterolemia, in addition to Alzheimer's disease.

APP is predominantly processed by a canonical pathway comprised of sequential cleavage by γ-secretases (encoded by presenilin1/2 genes) and α-secretase (encoded by ADAM10). This non-pathological processing of APP results in the formation of a neutotrophic peptide (sAPPα) which exhibits protection against glutamate toxicity and hypoglycemia (Araki et al., 1991; Mattson et al., 1993; Postina et al., 2004; Fahrenholz, 2007). An alternate APP processing pathway manifests itself in Alzheimer's disease, wherein APP is cleaved by γ- and β-secretases in cholesterol-rich lipid rafts. This "non-canonical" pathway results in the formation of Aβ peptides 38-43 amino acids long which tend to aggregate into plaques in the extracellular matrix, a hallmark of AD (Selkoe, 2002; Walsh et al., 2002; Selkoe, 2003; Meyer-Luehmann et al., 2008). While early-onset familial AD is explained by genetic lesions in APP or APP processing enzymes (PSEN1/2, BACE, ADAM), the underlying cause of late-onset sporadic AD (switch from non-pathogenic to pathogenic APP processing) remains unclear.

The importance of cholesterol homeostasis in the etiology of AD has been investigated in humans (Corder et al., 1993; Saunders et al., 1993; Blacker et al., 1997; Hofman et al., 1997) and in animal models (Joyce et al., 2002; Singaraja et al., 2002; Van Eck et al., 2006; Wahrle et al., 2008). Altering the cholesterol content of the plasma membrane has been shown to affect the function of membrane resident proteins (Scanlon et al., 2001; Lange et al., 2004). Elevated brain cholesterol was shown in subjects with AD (Mori et al., 2001), while rabbits fed on a cholesterol-rich diet have been shown to develop plaques in the brain (Ghribi et al., 2006). In vitro data showed that plasmalogen deficient cells possess elevated free-cholesterol in the membrane, while in humans, serum-plasmalogen deficiency has been shown to correlate with a decline in cognition status (Goodenowe et al., 2007). Based on these observations, we investigated the interplay between cholesterol and plasmalogens, and identify how the balance between the two affects the pathological manifestations of AD, measured in terms of secreted Aβ.

Proposed Mode of Action: A Shift in App Processing Via Membrane Lipid Modulation Human embryonic kidney (HEK293) cells express APP and the membrane-bound machinery required to process APP, making it a good model to study APP processing. The present in vitro investigation corroborated previous studies in that modulating membrane fluidity via cholesterol loading and/or plasmalogen precursor supplementation altered the extracellular Aβ42 content. Cholesterol loading of HEK293 cells increases the amount of free cholesterol by 17% (compared with Control) in the cells following a 48 hour incubation period. This elevation is accompanied with a parallel and significant increase ($p<0.05$) in the Aβ42 content in the conditioned medium compared with control. The 65% increase in amyloid is primarily due to 22% increase in β-secretase concentration (FIG. 18A, lane 2); the basal APP levels remain unchanged with cholesterol loading. Treatment of the cholesterol loaded HEK293 system with plasmalogen precursor PPI-1005 significantly reduced the free cholesterol content of the cell membrane ($p<0.05$). The Aβ42 content in the conditioned medium dropped 70% below cholesterol-loaded levels at the 20 µM concentration ($p=0.0001$), while the sAPPα content in the conditioned medium was elevated. The effects on APP processing do not appear to be due to a change in APP expression, rather it appears to be due to a shift in the APP processing pathway by virtue of changes in the abundance of APP processing enzymes. While β-secretase was restored to normal levels at 20 µM concentration of PPI-1005, a 73% increase in sAPPa species was detected in the conditioned medium. This elevation was explained by 63% increase in ADAM10 (FIG. 18A, lane 3), the enzyme responsible for sAPPα formation.

The change in cholesterol profile of the cells following plasmalogen supplementation can be explained by the observation that SOAT1, the enzyme responsible for esterification of free cholesterol is approximately 25% upregulated (compared with the cholesterol loaded condition) with increasing plasmalogen concentration (FIG. 18A, lane 5).

In a separate study, the effects of PPI-1005 were investigated in wild-type HEK293 cells, not loaded with cholesterol. FIG. 18B shows a concentration-dependent increase in abundance of ADAM10 (35%) and SOAT1 (50%); No change in BACE I or APP abundance was observed. Although when HEK293 cells were depleted of cholesterol by HMGCoA reductase inhibition by pravastatin, ADAM10 and SOAT1 protein levels remained constant (FIG. 18C). While plasmalogen and pravastatin treatments both significantly reduce the fraction of free cholesterol in the cells, it is the plasmalogen treatment alone that alters ADAM10 and SOAT levels in the cell. This suggests that the effects on ADAM10 and SOAT1 abundance is an effect of membrane plasmalogen content rather than membrane cholesterol content.

Accordingly, the abundance of membrane-resident proteins can be altered in vitro by modulating the cellular plasmalogen content, which is achieved by treating cells with plasmalogen precursors as described herein.

Materials and Methods

Cholesterol Loading

HEK 293 cells, cultured in DMEM, 10% FBS at 37° C., 5% $CO_2$, were seeded the day before the treatment. The following day, cells membranes were loaded with exogenous cholesterol at a concentration of 10 µg/ml media using methyl-β-cyclodextrin as the carrier to deliver cholesterol as described (Rong et al., 2003).

Cholesterol Assay

Cells were treated with the plasmalogen precursor PPI-1005 or with ethanol as the control. Cells were harvested after 48 hours using Versene: TryPLe express cocktail, washed with PBS. Lipids were extracted with chloroform containing 1% Triton X-100. The organic fraction was recovered and dried under a stream of nitrogen. The dried lipids were resuspended in cholesterol reaction buffer (Biovision, Mountain View, Calif.), and the total, free and esterified fractions of cholesterol were quantified using the cholesterol quantification kit (Biovision, Mountain View, Calif.) as per the manufacturer's recommendations. Cholesterol was initially calculated as µg/million cells, and reported as a percentage of control conditions for each experiment.

Amyloid Assay

HEK293 cells were loaded with exogenous cholesterol as described, and treated with a PPI 1005 or with ethanol as a control. Conditioned media from the treated cells was collected at the end of the 48 hour incubation period. For assaying $A\beta_{1-42}$ content, the conditioned media was enriched using Amicon ultracentrifugal filter devices (Millipore, Billerica, Mass.) prior to loading into the microplate. ELISA was carried out as per the manufacturer's recommendations (Covance Labs, Princeton, N.J.). The reactions were quenched 25 minutes after addition of the substrate, and the absorbance was read at 495 nm. The experiment was carried out in triplicate. Values were calculated as pg/ml of conditioned media, and were normalized to the amount of $A\beta$ detected in the conditioned media from untreated, cholesterol loaded control HEK293 cells.

Immunoblotting and Immunoprecipitation

HEK293 cells were treated as described in the amyloid assay. The cell pellet was washed in PBS and lysed in a RIPA buffer containing a protease inhibitor cocktail (Sigma, St. Louis, Mich.). Protein in the cell lysate was quantified using the Bio-Rad Protein Assay (Bio-Rad, Hercules, Calif.). The following antibodies were used for western analyses: APP (Calbiochem, Darmstadt, Germany), BACE1 and ADAM10 (Millipore, Temecula, Calif.), sAPPα (IBL, Gunma, Japan), SOAT1 (Santa Cruz Biotechnology Inc., CA), and β-actin (Sigma, St. Louis, Mich.). Immunoprecipitation was carried out to estimate sAPPα in the conditioned medium. Briefly, antibody to sAPPα was added to conditioned media and incubated for 16 hours at 4° C. IP was carried out by incubating with protein A/G agarose beads for 6 hours at 4° C. Beads were washed with PBS and the eluted proteins were detected by immunoblotting with anti-sAPPα antibody. Band intensities were quantified using Image Processing and Analysis in Java (ImageJ) software (National Institutes of Health, Bethesda, Md.)

Statistical Analysis

Statistical Analysis of the data was performed using Microsoft™ Office Excel 2007 and JMP version 8. Multiple comparison Dunnett's tests were applied to analyze the differences between the treatments and the control.

It will be apparent to persons skilled in the art that a number of variations and modifications can be made without departing from the scope of the invention as defined in the claims.

The following references, as well as those references provided above, are hereby incorporated by reference.

REFERENCES

1. Calderini G, Bonetti A C, Battistella A, Crews F T, Toffano G (1983) Biochemical changes of rat brain membranes with aging. Neurochem Res. 8:483-92.
2. Hashimoto M, Hossain S, Masumura S (1999) Effect of aging on plasma membrane fluidity of rat aortic endothelial cells. Exp Gerontol. 34:687-98.
3. Kessler A R, Kessler B, Yehuda S (1985) Changes in the cholesterol level, cholesterol-to-phospholipid mole ratio, and membrane lipid microviscosity in rat brain induced by age and a plant oil mixture. Biochem Pharmacol. 34:1120-1.
4. Lewin M B, Timiras P S (1984) Lipid changes with aging in cardiac mitochondrial membranes. Mech Ageing Dev. 24:343-51.
5. Modi H R, Katyare S S, Patel M A (2008) Ageing-induced alterations in lipid/phospholipid profiles of rat brain and liver mitochondria: implications for mitochondrial energy-linked functions. J Membr Biol. 221:51-60.
6. Wu C C, Su M J, Chi J F, Wu M H, Lee Y T (1997) Comparison of aging and hypercholesterolemic effects on the sodium inward currents in cardiac myocytes. Life Sci. 61:1539-51.
7. Guo J, Chi S, Xu H, Jin G, Qi Z (2008) Effects of cholesterol levels on the excitability of rat hippocampal neurons. Mol Membr Biol. 25:216-23.
8. Santiago J, Guzman G R, Rojas L V, Marti R, Asmar-Rovira G A, Santana L F, McNamee M, Lasalde-Dominicci J A (2001) Probing the effects of membrane cholesterol in the Torpedo californica acetylcholine receptor and the novel lipid-exposed mutation alpha C418W in Xenopus oocytes. J Biol. Chem. 276:46523-32.
9. Hashimoto M, Hossain S, Tanabe Y, Shido O (2005) Effects of aging on the relation of adenyl purine release with plasma membrane fluidity of arterial endothelial cells. Prostoglandins Leukot. Essent. Fatty Acids. 73:475-83.
10. Xiu J, Nordberg A, Qi X, Guan Z Z (2006) Influence of cholesterol and lovastatin on alpha-form of secreted amyloid precursor protein and expression of alpha7 nicotinic receptor on astrocytes. Neurochem Int. 49:459-65.
11. Miersch S, Espey M G, Chaube R, Akarca A, Tweten R, Ananvoranich S, Mutus B (2008) Plasma membrane cholesterol content affects nitric oxide diffusion dynamics and signaling. J Biol. Chem. 283:18513-21.
12. Cultler R G, Kelly J, Storie K, Pedersen W A, Tammara A, Hatanpaa K, Troncoso J C, Mattson M P (2004) Involvement of oxidative stress-induced abnormalities in ceramide and cholesterol metabolism in brain aging and Alzheimer's disease. Proc Natl Acad Sci U S A. 101:2070-5.
13. Corrigan F M, Horrobin D F, Skinner E R, Besson J A, Cooper M B (1998) Abnormal content of n-6 and n-3 long-chain unsaturated fatty acids in the phosphoglycerides and cholesterol esters of parahippocampal cortex from Alzheimer's disease patients and its relationship to acetyl CoA content. Int J Biochem Cell Biol. 30:197-207.
14. Distl R, Meske V, Ohm T G (2001) Tangle-bearing neurons contain more free cholesterol than adjacent tangle-free neurons. Acta Neuropathol. 101:547-54.
15. Grimm M O, Grimm H S, Tomic I, Beyreuther K, Hartmann T, Bergmann C (2008) Independent inhibition of Alzheimer disease beta- and gamma-secretase cleavage by lowered cholesterol levels. J Biol. Chem. 283:11302-11.
16. Simons M, Keller P, De Strooper B, Beyreuther K, Dotti C G, Simons K (1998) Cholesterol depletion inhibits the generation of beta-amyloid in hippocampal neurons. Proc Natl Acad Sci USA. 95:6460-4.
17. Beel A J, Mobley C K, Kim H J, Tian F, Hadziselimovic A, Jap B, Prestegard J H, Sanders C R (2008) Structural studies of the transmembrane C-terminal domain of the amyloid precursor protein (APP): does APP function as a cholesterol sensor? Biochemistry. 47:9428-46.

18. Sigle J P, Zander J, Ehret A, Honegger J, Jackisch R, Feuerstein T J (2003) High potassium-induced activation of choline-acetyltransferase in human neocortex: implications and species differences. Brain Res Bull. 60:255-62.
19. Wolozin B, Wang S W, Li N C, Lee A, Lee T A, Kazis L E (2007) Simvastatin is associated with a reduced incidence of dementia and Parkinson's disease. BMC Med. 5:20.
20. Li C M, Clark M E, Rudolf M, Curcio C A (2007) Distribution and composition of esterified and unesterified cholesterol in extra-macular drusen. Exp Eye Res. 85:192-201.
21. Hager M H, Solomon K R, Freeman M R (2006) The role of cholesterol in prostate cancer. Curr Opin Clin Nutr Metab Care.; 9:379-85.
22. Campbell A M, Chan S H (2008) Mitochondrial membrane cholesterol, the voltage dependent anion channel (VDAC), and the Warburg effect. J Bioenerg Biomembr.
23. Vejux A, Malvitte L, Lizard G (2008) Side effects of oxysterols: cytotoxicity, oxidation, inflammation, and phospholipidosis. Braz J Med Biol Res. 41:545-56.
24. Streit W J, Sparks D L (1997) Activation of microglia in the brains of humans with heart disease and hypercholesterolemic rabbits. J Mol. Med. 75:130-8.
25. Diestel A, Aktas O, Hackel D, Hake I, Meier S, Raine C S, Nitsch R, Zipp F, Ullrich O (2003) Activation of microglial poly(ADP-ribose)-polymerase-1 by cholesterol breakdown products during neuroinflammation: a link between demyelination and neuronal damage. J Exp Med. 198: 1729-40.
26. Thirumangalakudi L, Prakasam A, Zhang R, Bimonte-Nelson H, Sambamurti K, Kindy M S, Bhat N R (2008) High cholesterol-induced neuroinflammation and amyloid precursor protein processing correlate with loss of working memory in mice. J. Neurochem. 106:475-85.
27. Shin J, Thompson D H (2003) Direct synthesis of plasmenylcholine from allyl-substituted glycerols. J Org. Chem. 68:6760-6.
28. Gupta C M, Radhakrishnan R, Khorana H G (1977) Glycerophospholipid synthesis: improved general method and new analogs containing photoactivable groups. Proc Natl Acad Sci USA. 74:4315-9.
29. Watt M J, Steinberg G R (2008) Regulation and function of triacylglycerol lipases in cellular metabolism. Biochem J. 414:313-25.
30. Nagan N, Hajra A K, Larkins L K, Lazarow P, Purdue P E, Rizzo W B, Zoeller R A. (1998) Isolation of a Chinese hamster fibroblast variant defective in dihydroxyacetone-phosphate acyltransferase activity and plasmalogen biosynthesis: use of a novel two-step selection protocol. Biochem J. 332:273-9.
31. Goodenowe D B, Cook L L, Liu J, Lu Y, Jayasinghe D A, Ahiahonu P W, Heath D, Yamazaki Y, Flax J, Krenitsky K F, Sparks D L, Lerner A, Friedland R P, Kudo T, Kamino K, Morihara T, Takeda M, Wood P L (2007) Peripheral ethanolamine plasmalogen deficiency: a logical causative factor in Alzheimer's disease and dementia. J Lipid Res. 48:2485-98.
32. Araki W, Kitaguchi N, Tokushima Y, Ishii K, Aratake H, Shimohama S, Nakamura S and Kimura J (1991) Trophic effect of beta-amyloid precursor protein on cerebral cortical neurons in culture. Biochem Biophys Res Commun 181:265-271.
33. Blacker D, Haines J L, Rodes L, Terwedow H, Go R C, Harrell L E, Perry R T, Bassett S S, Chase G, Meyers D, Albert M S and Tanzi R (1997) ApoE-4 and age at onset of Alzheimer's disease: the NIMH genetics initiative. Neurology 48:139-147.
34. Corder E H, Saunders A M, Strittmatter W J, Schmechel D E, Gaskell P C, Small G W, Roses A D, Haines J L and Pericak-Vance M A (1993) Gene dose of apolipoprotein E type 4 allele and the risk of Alzheimer's disease in late onset families. Science 261:921-923.
35. Fahrenholz F (2007) Alpha-secretase as a therapeutic target. Curr Alzheimer Res 4:412-417.
36. Ghribi O, Larsen B, Schrag M and Herman M M (2006) High cholesterol content in neurons increases BACE, beta-amyloid, and phosphorylated tau levels in rabbit hippocampus. Exp Neurol 200:460-467.
37. Hofman A, Ott A, Breteler M M, Bots M L, Slooter A J, van Harskamp F, van Duijn C N, Van Broeckhoven C and Grobbee D E (1997) Atherosclerosis, apolipoprotein E, and prevalence of dementia and Alzheimer's disease in the Rotterdam Study. Lancet 349:151-154.
38. Joyce C W, Amar M J, Lambert G, Vaisman B L, Paigen B, Najib-Fruchart J, Hoyt R F, Jr., Neufeld E D, Remaley A T, Fredrickson D S, Brewer H B, Jr. and Santamarina-Fojo S (2002) The ATP binding cassette transporter A1 (ABCA1) modulates the development of aortic atherosclerosis in C57BL/6 and apoE-knockout mice. Proc Natl Acad Sci USA 99:407-412.
39. Lange Y, Ye J and Steck T L (2004) How cholesterol homeostasis is regulated by plasma membrane cholesterol in excess of phospholipids. Proc Natl Acad Sci USA 101: 11664-11667.
40. Mattson M P, Cheng B, Culwell A R, Esch F S, Lieberburg I and Rydel R E (1993) Evidence for excitoprotective and intraneuronal calcium-regulating roles for secreted forms of the beta-amyloid precursor protein. Neuron 10:243-254.
41. Meyer-Luehmann M, Spires-Jones T L, Prada C, Garcia-Alloza M, de Calignon A, Rozkalne A, Koenigsknecht-Talboo J, Holtzman D M, Bacskai B J and Hyman B T (2008) Rapid appearance and local toxicity of amyloid-beta plaques in a mouse model of Alzheimer's disease. Nature 451:720-724.
42. Mori T, Paris D, Town T, Rojiani A M, Sparks D L, Delledonne A, Crawford F, Abdullah L I, Humphrey J A, Dickson D W and Mullan M J (2001) Cholesterol accumulates in senile plaques of Alzheimer disease patients and in transgenic APP(SW) mice. J Neuropathol Exp Neurol 60:778-785.
43. Postina R, Schroeder A, Dewachter I, Bohl J, Schmitt U, Kojro E, Prinzen C, Endres K, Hiemke C, Blessing M, Flamez P, Dequenne A, Godaux E, van Leuven F and Fahrenholz F (2004) A disintegrin-metalloproteinase prevents amyloid plaque formation and hippocampal defects in an Alzheimer disease mouse model. J Clin Invest 113: 1456-1464.
44. Rong J X, Shapiro M, Trogan E and Fisher E A (2003) Transdifferentiation of mouse aortic smooth muscle cells to a macrophage-like state after cholesterol loading. Proc Natl Acad Sci USA 100:13531-13536.
45. Saunders A M, Strittmatter W J, Schmechel D, George-Hyslop P H, Pericak-Vance M A, Joo S H, Rosi B L, Gusella J F, Crapper-MacLachlan D R, Alberts M J and et al. (1993) Association of apolipoprotein E allele epsilon 4 with late-onset familial and sporadic Alzheimer's disease. Neurology 43:1467-1472.
46. Scanlon S M, Williams D C and Schloss P (2001) Membrane cholesterol modulates serotonin transporter activity. Biochemistry 40:10507-10513.
47. Selkoe D J (2002) Alzheimer's disease is a synaptic failure. Science 298:789-791.
48. Selkoe D J (2003) Folding proteins in fatal ways. Nature 426:900-904.

49. Singaraja R R, Fievet C, Castro G, James E R, Hennuyer N, Clee S M, Bissada N, Choy J C, Fruchart J C, McManus B M, Staels B and Hayden M R (2002) Increased ABCA1 activity protects against atherosclerosis. *J Clin Invest* 110: 35-42.
50. Van Eck M, Singaraja R R, Ye D, Hildebrand R B, James E R, Hayden M R and Van Berkel T J (2006) Macrophage ATP-binding cassette transporter A1 overexpression inhibits atherosclerotic lesion progression in low-density lipoprotein receptor knockout mice. *Arterioscler Thromb Vasc Biol* 26:929-934.
51. Wahrle S E, Jiang H, Parsadanian M, Kim J, Li A, Knoten A, Jain S, Hirsch-Reinshagen V, Wellington C L, Bales K R, Paul S M and Holtzman D M (2008) Overexpression of ABCA1 reduces amyloid deposition in the PDAPP mouse model of Alzheimer disease. J Clin Invest 118:671-682.
52. Walsh D M, Klyubin I, Fadeeva J V, Cullen W K, Anwyl R, Wolfe M S, Rowan M J and Selkoe D J (2002) Naturally secreted oligomers of amyloid beta protein potently inhibit hippocampal long-term potentiation in vivo. Nature 416: 535-539.

What is claimed is:

1. A compound of formula I:

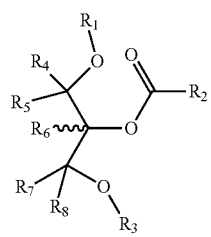

(I)

wherein:
R$_1$ and R$_2$ are the same or different and selected from an alkyl or alkenyl hydrocarbon chain selected from the group consisting of: CH$_3$(CH$_2$)$_3$—, CH$_3$(CH$_2$)$_5$—, CH$_3$(CH$_2$)$_7$—, CH$_3$(CH$_2$)$_9$—, CH$_3$(CH$_2$)$_{11}$—, CH$_3$(CH$_2$)$_{13}$—, CH$_3$(CH$_2$)$_{15}$—, CH$_3$(CH$_2$)$_{17}$—, CH$_3$(CH$_2$)$_{19}$—, CH$_3$(CH$_2$)$_{21}$—, CH$_3$(CH$_2$)$_{23}$—, CH$_3$(CH$_2$)$_3$CH=CH (CH$_2$)$_7$—, CH$_3$(CH$_2$)$_5$CH=CH (CH$_2$)$_7$—, CH$_3$(CH$_2$)$_7$CH=CH(CH$_2$)$_7$—, CH$_3$(CH$_2$)$_4$CH=CHCH$_2$CH=CH(CH$_2$)$_7$—, CH$_3$CH$_2$CH=CHCH$_2$CH=CHCH$_2$CH=CH (CH$_2$)$_7$—, CH$_3$CH$_2$(CH=CH)—, CH$_3$(CH$_2$)$_3$(CH=CH)—, CH$_3$(CH$_2$)$_5$(CH=CH)—, CH$_3$(CH$_2$)$_7$(CH=CH)—, CH$_3$(CH$_2$)$_9$(CH=CH)—, CH$_3$(CH$_2$)$_{11}$(CH=CH)—, CH$_3$(CH$_2$)$_{13}$(CH=CH)—, CH$_3$(CH$_2$)$_{15}$(CH=CH)—, CH$_3$(CH$_2$)$_{17}$(CH=CH)—, CH$_3$(CH$_2$)$_{19}$(CH=CH)—, CH$_3$(CH$_2$)$_{21}$(CH=CH)—, CH$_3$(CH$_2$)$_3$CH=CH(CH$_2$)$_5$ (CH=CH)—, CH$_3$(CH$_2$)$_5$CH=CH (CH$_2$)$_5$(CH=CH)—, CH$_3$(CH$_2$)$_7$CH=CH(CH$_2$)$_5$ (CH=CH)—, CH$_3$(CH$_2$)$_4$CH=CHCH$_2$CH=CH (CH$_2$)$_5$(CH=CH), CH$_3$CH$_2$CH=CHCH$_2$CH=CHCH$_2$CH=CH(CH$_2$)$_5$ (CH=CH)—, CH$_3$(CH$_2$)$_3$CH=CH(CH$_2$)$_7$—, CH$_3$(CH$_2$)$_5$CH=CH(CH$_2$)$_7$—, CH$_3$(CH$_2$)$_7$CH=CH (CH$_2$)$_7$—, CH$_3$(CH$_2$)$_4$(CH=CHCH$_2$)$_2$(CH$_2$)$_6$—, CH$_3$CH$_2$(CH=CHCH$_2$)$_3$(CH$_2$)$_6$—, CH$_3$(CH$_2$)$_4$ (CH=CHCH$_2$)$_4$(CH$_2$)$_2$—, CH$_3$CH$_2$(CH=CHCH$_2$)$_5$ (CH$_2$)$_2$—, CH$_3$(CH$_2$)$_7$CH=CH(CH$_2$)$_{11}$, and CH$_3$CH$_2$(CH=CHCH$_2$)$_6$CH$_2$—;

R$_3$ is selected from the group consisting of carnitine, acetyl-DL-carnitine, thiocarnitine, acetyl-DL-thiocarnitine, creatine, norcarnitine, lipoic acid, dihydrolipoic acid, N-acetylcysteine, substituted or unsubstituted amino acid groups and groups of the structures shown below:

R$_4$ and R$_5$ are independently hydrogen or lower alkyl;
R$_6$ is hydrogen or lower alkyl; and
R$_7$ and R$_8$ are independently hydrogen or lower alkyl,
including racemates or isolated stereoisomers and pharmaceutically acceptable salts or esters thereof.

2. The compound of claim 1, wherein R$_2$ is CH$_3$CH$_2$ (CH=CHCH$_2$)$_6$CH$_2$—.

3. The compound of claim 1, wherein said compound is selected from the group consisting of 2-acetoxy-4-(2-((4Z, 7Z,10Z,13Z,16Z,19Z)-docosa-4,7,10,13,16,19-hexaenoyloxy)-3-(hexadecyloxy)propoxy)-N,N,N-trimethyl-4-oxobutan-1-aminium (PPI-1009), (4Z, 7Z, 10Z, 13Z, 16Z, 19Z)-1-(5-((R)-1,2-dithiolan-3-yl)pentanoyloxy)-3-(hexadecyloxy)propan-2-yl docosa-4, 7, 10, 13, 16, 19-hexaenoate (PPI-1011) and (4Z, 7Z, 10Z, 13Z, 16Z, 19Z)-1-(2-acetamido-3-mercaptopropanoyloxy)-3-(hexadecyloxy)propan-2-yl docosa-4, 7, 10, 13, 16, 19-hexaenoate (PPI-1014).

4. A pharmaceutical composition comprising a pharmaceutically acceptable carrier and a compound as defined in claim 1.

5. The pharmaceutical composition of claim 4, wherein $R_2$ is $CH_3CH_2(CH=CHCH_2)_6CH_2$—.

6. The pharmaceutical composition of claim 4, wherein the compound is selected from the group consisting of 2-acetoxy-4-(2-((4Z,7Z,10Z,13Z,16Z,19Z)-docsa-4, 7,10, 13, 16, 19-hex aenoyloxy)-3-(hex adecyloxy)propoxy)-N,N,N-trimethyl-4-oxobutan-1-aminium (PPI-1009), (4Z, 7Z, 10Z, 13Z, 16Z, 19Z)-1-(5(R)-1,2-dithiolan-3-yl)pentanoyloxy)-3-(hexadecyloxy)propan-2-yl docosa-4, 7, 10, 13, 16, 19-hexaenoate (PPI-1011) and (4Z, 7Z, 10Z, 13Z, 16Z, 19Z)-1-(2-acetamido-3-mercaptoprop anoyloxy)-3-(hex adecyloxy)propan-2-yl docosa-4, 7, 10, 13, 16, 19-hexaenoate (PPI-1014).

\* \* \* \* \*